United States Patent
Downes et al.

(10) Patent No.: US 10,188,627 B2
(45) Date of Patent: Jan. 29, 2019

(54) PPAR AGONISTS, COMPOUNDS, PHARMACEUTICAL COMPOSITIONS, AND METHODS OF USE THEREOF

(71) Applicants: Mitobridge, Inc., Cambridge, MA (US); SALK INSTITUTE FOR BIOLOGICAL STUDIES, La Jolla, CA (US)

(72) Inventors: Michael Downes, La Jolla, CA (US); Ronald Evans, La Jolla, CA (US); Arthur Kluge, Lincoln, MA (US); Bharat Lagu, Acton, MA (US); Masanori Miura, Tsukuba (JP); Sunil Kumar Panigrahi, Hyderabad (IN); Michael Patane, Andover, MA (US); Susanta Samajdar, Hyderabad (IN); Ramesh Senaiar, Hyderabad (IN); Taisuke Takahashi, Tsukuba (JP)

(73) Assignees: Mitobridge, Inc., Cambridge, MA (US); Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 15/517,893

(22) PCT Filed: Oct. 7, 2015

(86) PCT No.: PCT/US2015/054477
§ 371 (c)(1),
(2) Date: Apr. 7, 2017

(87) PCT Pub. No.: WO2016/057660
PCT Pub. Date: Apr. 14, 2016

(65) Prior Publication Data
US 2017/0304255 A1    Oct. 26, 2017

Related U.S. Application Data

(60) Provisional application No. 62/061,430, filed on Oct. 8, 2014.

(51) Int. Cl.
| | |
|---|---|
| A61K 31/341 | (2006.01) |
| C07D 307/54 | (2006.01) |
| C07D 307/79 | (2006.01) |
| A61K 31/166 | (2006.01) |
| C07C 233/11 | (2006.01) |
| C07D 235/20 | (2006.01) |
| C07D 307/38 | (2006.01) |
| C07D 403/14 | (2006.01) |
| C07D 417/14 | (2006.01) |

(52) U.S. Cl.
CPC .......... *A61K 31/341* (2013.01); *A61K 31/166* (2013.01); *C07C 233/11* (2013.01); *C07D 235/20* (2013.01); *C07D 307/38* (2013.01); *C07D 307/54* (2013.01); *C07D 307/79* (2013.01); *C07D 403/14* (2013.01); *C07D 417/14* (2013.01)

(58) Field of Classification Search
CPC .................................................... A61K 31/341
USPC ........................................................ 549/491
See application file for complete search history.

(56) References Cited

U.S. PATENT DOCUMENTS

| | | |
|---|---|---|
| 7,655,641 B2 | 2/2010 | Conner et al. |
| 2004/0214888 A1 | 10/2004 | Matsuura et al. |
| 2005/0075378 A1 | 4/2005 | Gossett et al. |
| 2006/0116410 A1 | 6/2006 | Banner et al. |
| 2007/0082907 A1 | 4/2007 | Canada et al. |

FOREIGN PATENT DOCUMENTS

WO    2014165827 A1    10/2014

OTHER PUBLICATIONS

King, Med. Chem., Principle and Practice (1994), pp. 206-208.*
Lamers et al., Therapeutic modulators of peroxisome proliferator-activated receptors (PPAR): a patent review (2008-present). Expert Opin Ther Pat. Jul. 2012;22(7):803-41.
Mitachi et al., Synthesis and structure-activity relationship of disubstituted benzamides as a novel class of antimalarial agents. Bioorg Med Chem Lett. Jul. 15, 2012;22(14):4536-9.
Warshawsky et al., Synthesis and evaluation of aminomethyl dihydrocinnamates as a new class of PPAR ligands. Bioorg Med Chem Lett. Dec. 15, 2006;16(24):6328-33.
International Search Report for Application No. PCT/US2015/054477, dated Nov. 26, 2015. 6 pages.
International Preliminary Report on Patentability for Application No. PCT/US2015/054477, dated Apr. 20, 2017. 10 pages.

* cited by examiner

*Primary Examiner* — Taofiq A Solola
(74) *Attorney, Agent, or Firm* — McCarter & English, LLP; Steven G. Davis; Wei Song

(57) ABSTRACT

Provided herein are compounds of formula (I) useful for the treatment of PPAR-delta related diseases (e.g. mitochondrial diseases, muscular diseases, vascular diseases, demyelinating diseases and metabolic diseases).

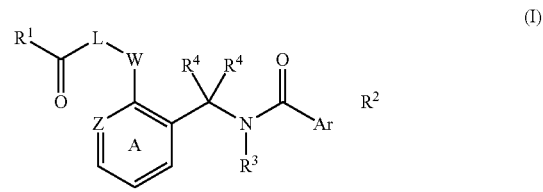

(I)

28 Claims, 12 Drawing Sheets

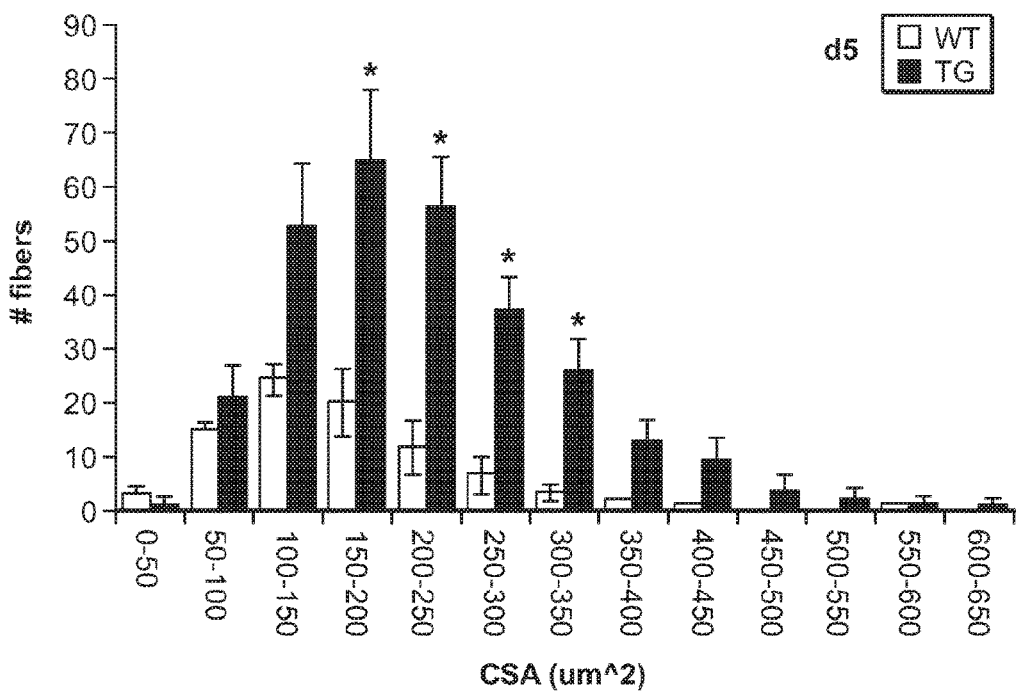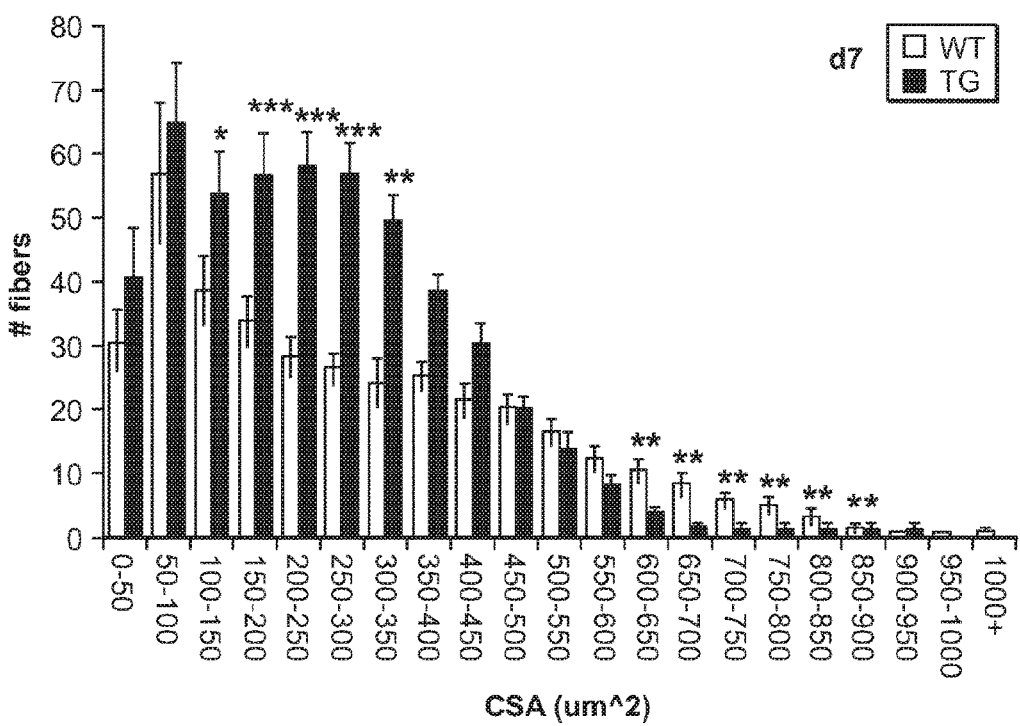

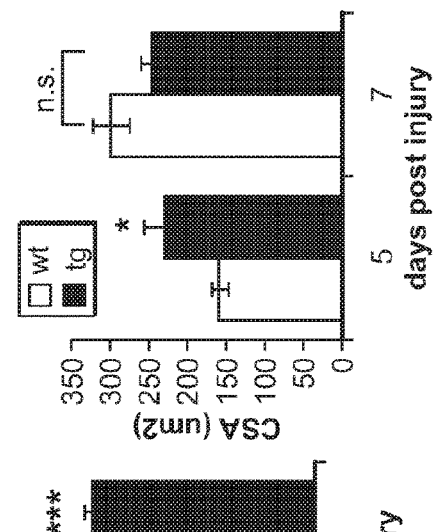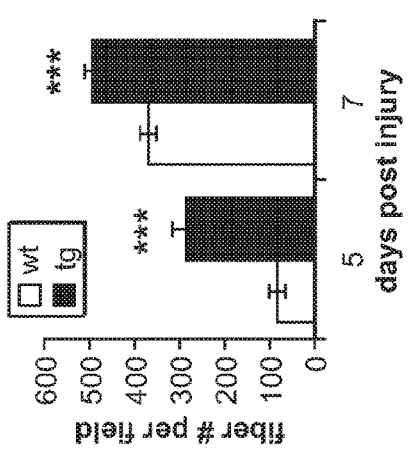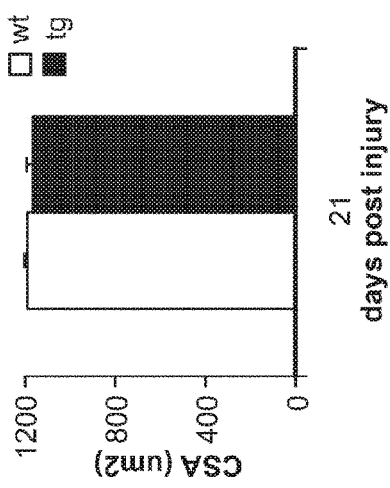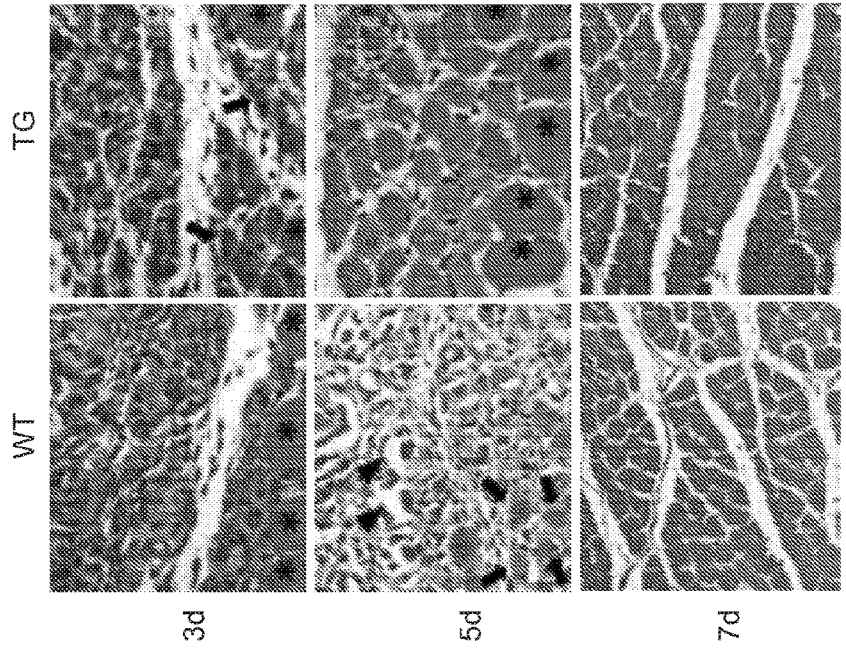

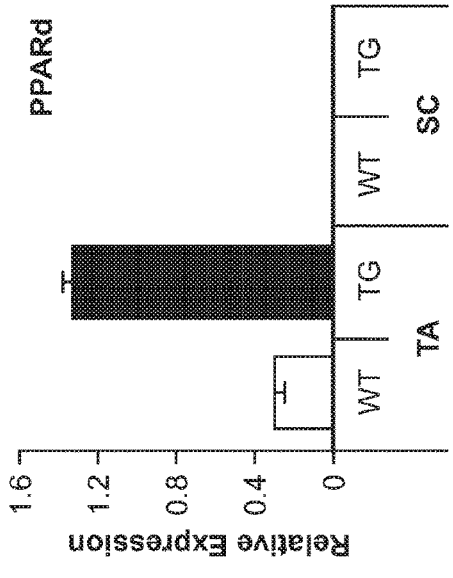
FIG. 4D  FIG. 4E
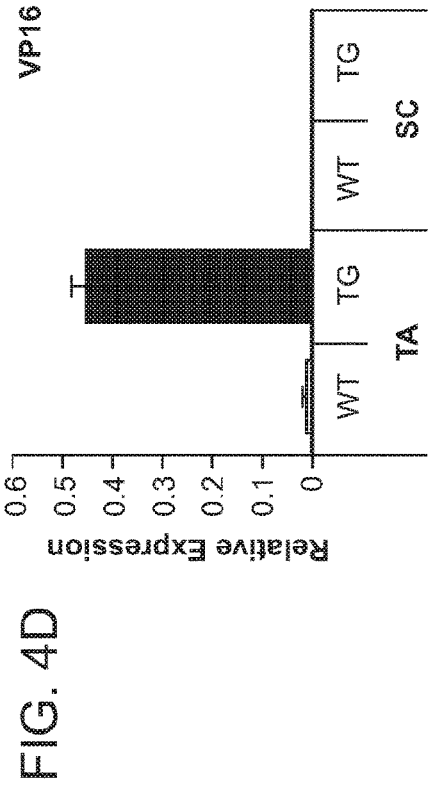
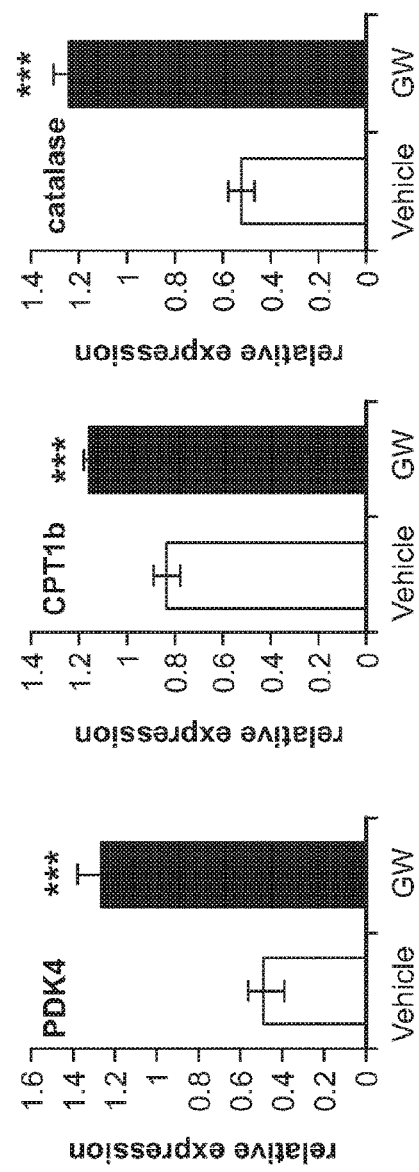
FIG. 5A

FIG. 5B
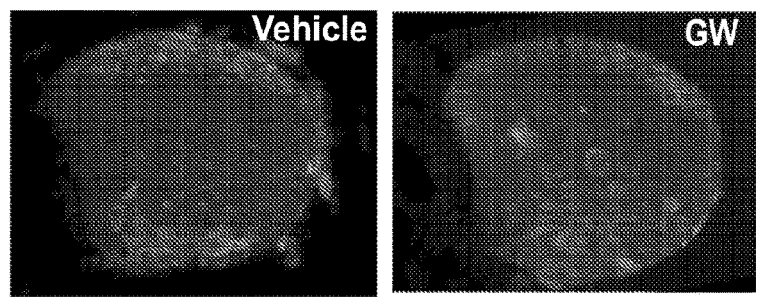
FIG. 5C
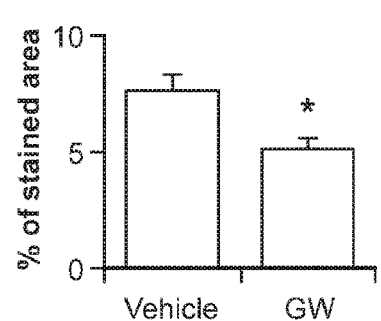
FIG. 5D
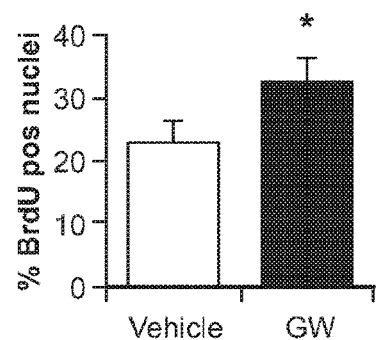
FIG. 5E
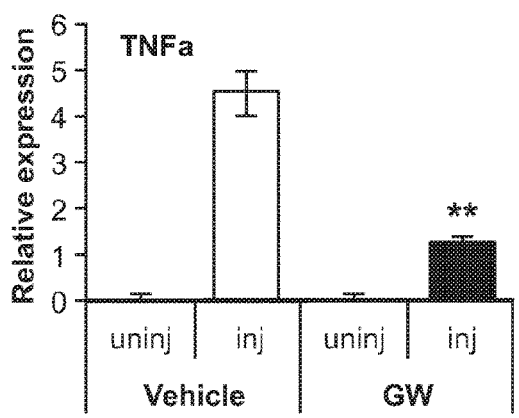
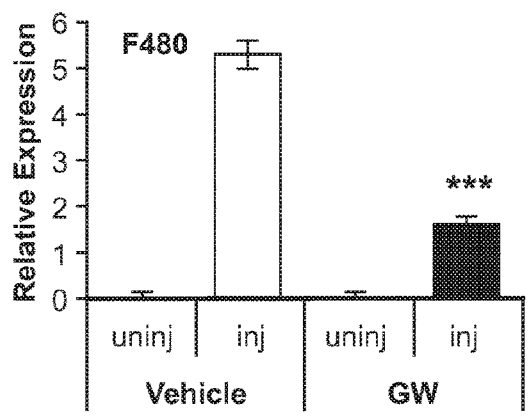

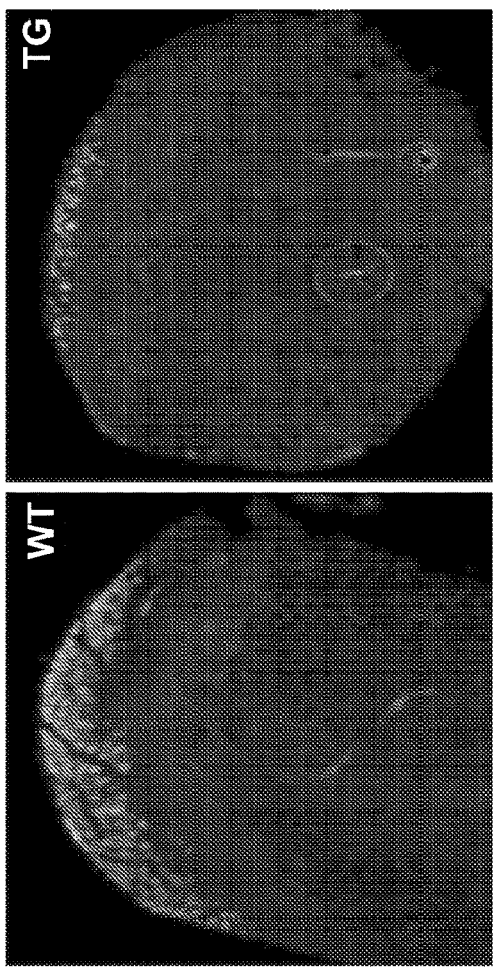
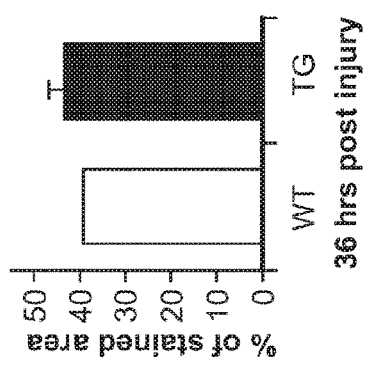
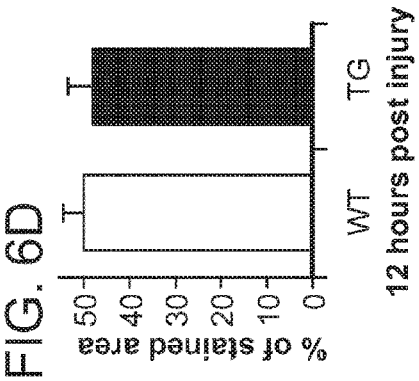
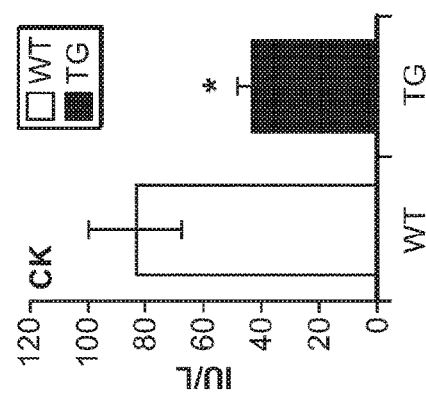
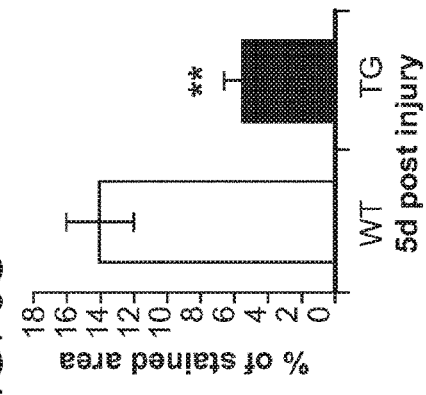

FIG. 7A
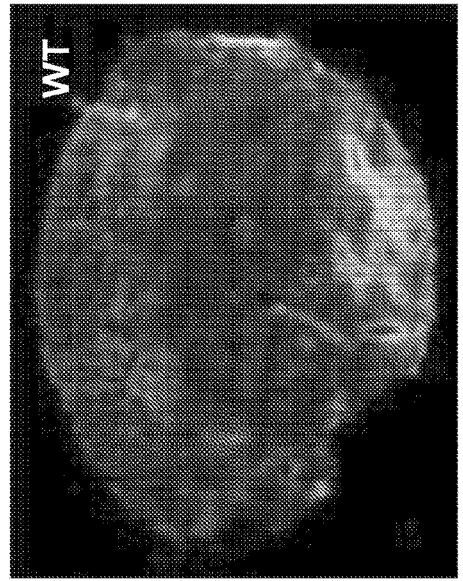
FIG. 7B
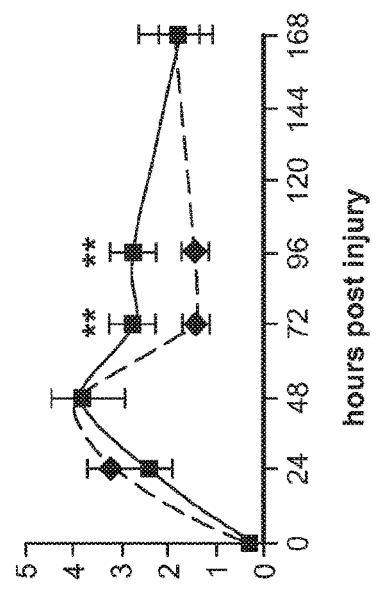
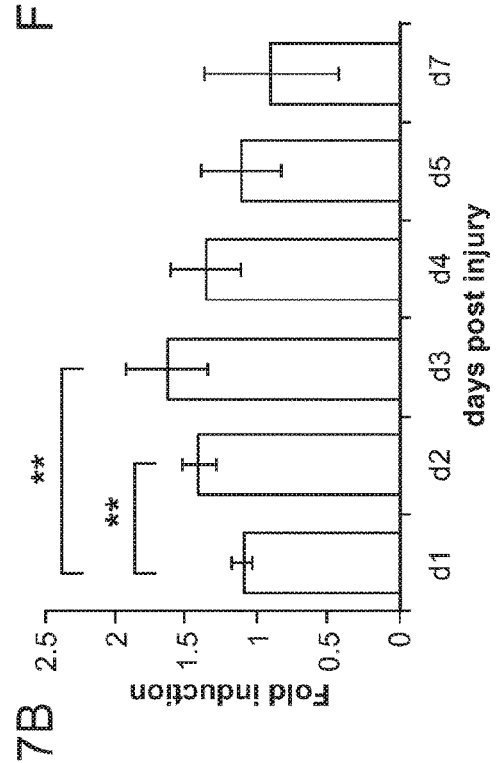
FIG. 7C

PPAR AGONISTS, COMPOUNDS, PHARMACEUTICAL COMPOSITIONS, AND METHODS OF USE THEREOF

RELATED APPLICATIONS

This application is a 35 U.S.C. § 371 national stage filing of International Application No. PCT/US2015/054477, filed on Oct. 7, 2015, which claims priority to U.S. Provisional Application No. 62/061,430, filed on Oct. 8, 2014. The entire contents of each of the foregoing applications are incorporated herein by reference.

ACKNOWLEDGMENT OF GOVERNMENT SUPPORT

This invention was made with government support under DK057978-32 awarded by the National Institutes of Health. The United States government has certain rights in the invention.

FIELD

This application concerns agonists of peroxisome proliferator-activated receptors (PPAR), particularly PPAR delta (PPARδ), and methods for their use, such as to treat or prevent one or more PPARδ-related diseases.

BACKGROUND

Peroxisome proliferator-activated receptor delta (PPARδ) is a nuclear receptor that is capable of regulating mitochondria biosynthesis. As shown in PCT/US2014/033088 (incorporated herein by reference), modulating the activity of PPARδ is useful for the treatment of diseases, developmental delays, and symptoms related to mitochondrial dysfunction, such as Alpers's Disease, MERRF-Myoclonic epilepsy and ragged-red fiber disease, Pearson Syndrome, and the like. Modulation PPARδ activity is effective in the treatment of other conditions, such as muscular diseases, demyelinating diseases, vascular diseases, and metabolic diseases. Indeed, PPARδ is an important biological target for compounds used to help treat and prevent mitochondrial diseases, muscle-related diseases and disorders, and other related conditions.

Accordingly, there remains a need in the art for novel compounds capable of effectively and reliably activating PPARδ in vitro and in vivo. There is also a need for PPARδ activating compounds with improved pharmacokinetic properties and improved metabolic stability. The present invention addresses these and other such needs.

SUMMARY

Provided herein, inter alia, are compounds and compositions comprising such compounds that are useful for increasing PPARδ activity. In particular, disclosed herein are methods modulating the activity of PPARδ for the treatment of diseases, developmental delays, and symptoms related to mitochondrial dysfunction (see, e.g., Examples 1-7). For example, the disclosed compounds and compositions are useful in the treatment of mitochondrial diseases, such as Alpers's Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, and retinitis pigmentosa, and Pearson Syndrome. Alternatively, the disclosed compounds and compositions are useful in the treatment of other PPARδ-related diseases, such as muscular diseases, demyelinating diseases, vascular diseases, and metabolic diseases.

In one embodiment, provided herein is a compound of Formula (I):

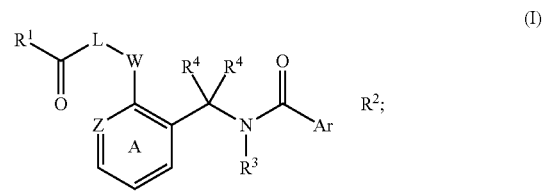

or a pharmaceutically acceptable salt thereof,
wherein:
Z is CH, N, or

Ring A is optionally substituted (e.g., with halogen, $C_1$-$C_4$-alkyl, $C_1$-$C_4$-haloalkyl, CN, $C_1$-$C_4$-alkoxy, $C_1$-$C_4$-haloalkoxy, or $C_3$-$C_6$-cycloalkyl) phenylene when Z is CH, optionally substituted (e.g., with halogen, $C_1$-$C_4$-alkyl, $C_1$-$C_4$-haloalkyl, CN, $C_1$-$C_4$-alkoxy, $C_1$-$C_4$-haloalkoxy, or $C_3$-$C_6$-cycloalkyl) pyridinylene when Z is N, or optionally substituted (e.g., with halogen, $C_1$-$C_4$-alkyl, $C_1$-$C_4$-haloalkyl, CN, $C_1$-$C_4$-alkoxy, $C_1$-$C_4$-haloalkoxy, or $C_3$-$C_6$-cycloalkyl) N-oxide pyridinylene when Z is

Ar is optionally substituted (e.g., with halogen, $C_1$-$C_4$-alkyl, $C_1$-$C_4$-haloalkyl, CN, $C_1$-$C_4$-alkoxy, $C_1$-$C_4$-haloalkoxy, or $C_3$-$C_6$-cycloalkyl) 5 or 6-membered monocyclic arylene or heteroarylene, provided that when Ar is 5-membered heteroarylene, $R^2$ and —C(O)NR$^3$— are oriented 1, 3 to each other on the ring, wherein position 1 is the point of attachment of Ar to the —C(O)NR$^3$—; or
Ar is optionally substituted 9- or 10-membered fused bicyclic heteroarylene;
$R^1$ is —OR$^{1A}$ or —NR$^{1A}$R$^{1B}$;
$R^{1A}$, $R^{1B}$ are each independently hydrogen or $C_1$-$C_4$-alkyl;
W is O, and L is —(CH$_2$)$_n$—, wherein n is an integer between 1 and 6, and one or more (CH$_2$) is replaced with —CH$_2$—CH(CH$_3$)—, —CH(CH$_3$)—CH$_2$—, —CH$_2$—C(CH$_3$)$_2$—, —C(CH$_3$)$_2$—CH$_2$—, —HC=C(CH$_3$)—, —(CH$_3$)C=CH—,

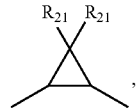

—CH$_2$—O—CH$_2$—, —CH$_2$—S—CH$_2$—, —CH$_2$—CH(F)—, —CH(F)—CH$_2$—, —CH$_2$—CF$_2$—, —CF$_2$—CH$_2$—, —CH$_2$—C(O)—, —C(O)—CH$_2$—, optionally substituted arylene (e.g., with halogen, C$_1$-C$_4$-alkyl, C$_1$-C$_4$-haloalkyl, CN, C$_1$-C$_4$-alkoxy, C$_1$-C$_4$-haloalkoxy, or C$_3$-C$_6$-cycloalkyl), optionally substituted arylene ether (e.g., with halogen, C$_1$-C$_4$-alkyl, C$_1$-C$_4$-haloalkyl, CN, C$_1$-C$_4$-alkoxy, C$_1$-C$_4$-haloalkoxy, or C$_3$-C$_6$-cycloalkyl), or optionally substituted heteroarylene (e.g., with halogen, C$_1$-C$_4$-alkyl, C$_1$-C$_4$-haloalkyl, CN, C$_1$-C$_4$-alkoxy, C$_1$-C$_4$-haloalkoxy, or C$_3$-C$_6$-cycloalkyl); or W is CH$_2$, CH=CH, or C≡C, and L is —(CH$_2$)$_n$—, wherein n is an integer between 1 and 6, and one or more (CH$_2$) is optionally replaced with —CH$_2$—CH(CH$_3$)—, —CH(CH$_3$)—CH$_2$—, —CH$_2$—C(CH$_3$)$_2$—, —C(CH$_3$)$_2$—CH$_2$—, —HC=C(CH$_3$)—, —(CH$_3$)C=CH—,

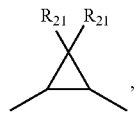

—CH$_2$—O—CH$_2$—, —CH$_2$—S—CH$_2$—, —CH$_2$—CH(F)—, —CH(F)—CH$_2$—, —CH$_2$—CF$_2$—, —CF$_2$—CH$_2$—, —CH$_2$—C(O)—, or —C(O)—CH$_2$—;

each R$^{21}$ is independently hydrogen, halogen, or C$_1$-C$_4$-alkyl;

R$^2$ is halogen, C$_1$-C$_4$-alkyl, C$_3$-C$_6$-cycloalkyl, CN, C$_1$-C$_4$-alkoxy, C$_1$-C$_4$-haloalkoxy, SO$_2$(C$_1$-C$_4$-alkyl), 5- or 6-membered heterocycloalkyl, =R$^{2A}$, —O(CH$_2$)$_m$R$^{2B}$, NH(C$_1$-C$_4$-alkyl), N(C$_1$-C$_4$-alkyl)$_2$, C(O)(C$_1$-C$_4$-alkyl), optionally substituted aryl, or optionally substituted 5-membered heteroaryl;

m is an integer having an a value of 0, 1, 2, or 3;

R$^{2A}$ and R$^{2B}$ are each independently C$_1$-C$_4$-alkyl, C$_3$-C$_6$-cycloalkyl, or C$_1$-C$_4$ haloalkyl;

R$^3$ is C$_1$-C$_4$-alkyl,

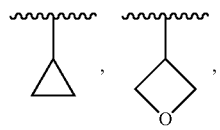

or C$_1$-C$_4$-haloalkyl; and each R$^4$ is independently H, D, or F;

with the proviso that the compound is not selected from the group consisting of:

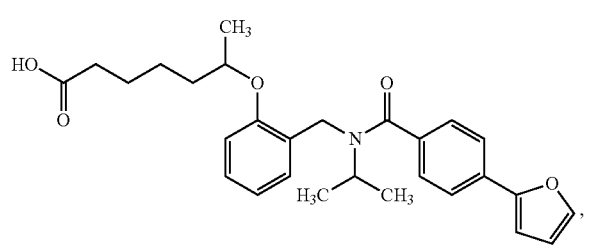

-continued

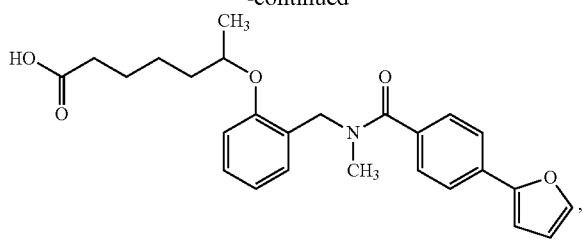

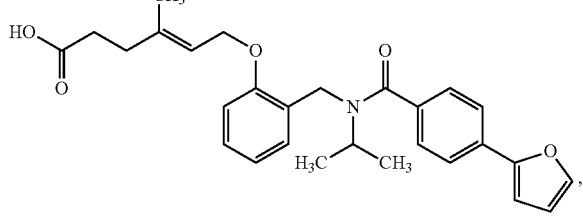

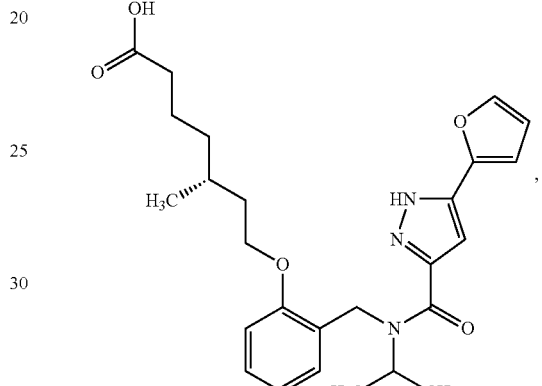

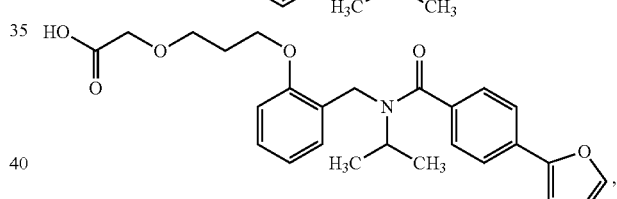

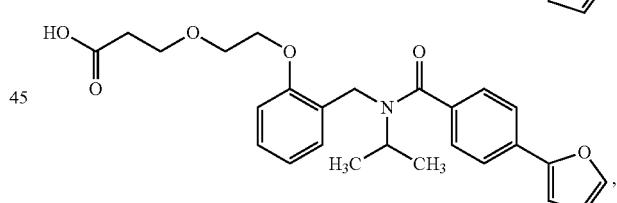

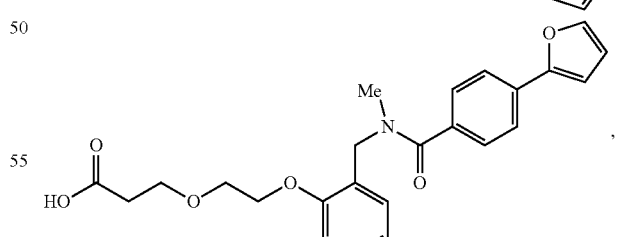

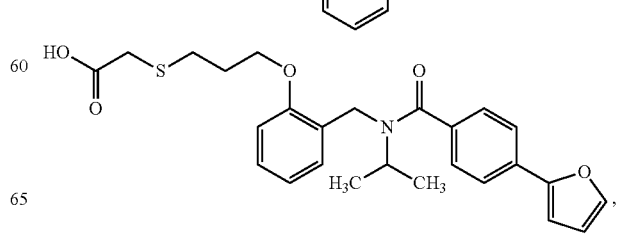

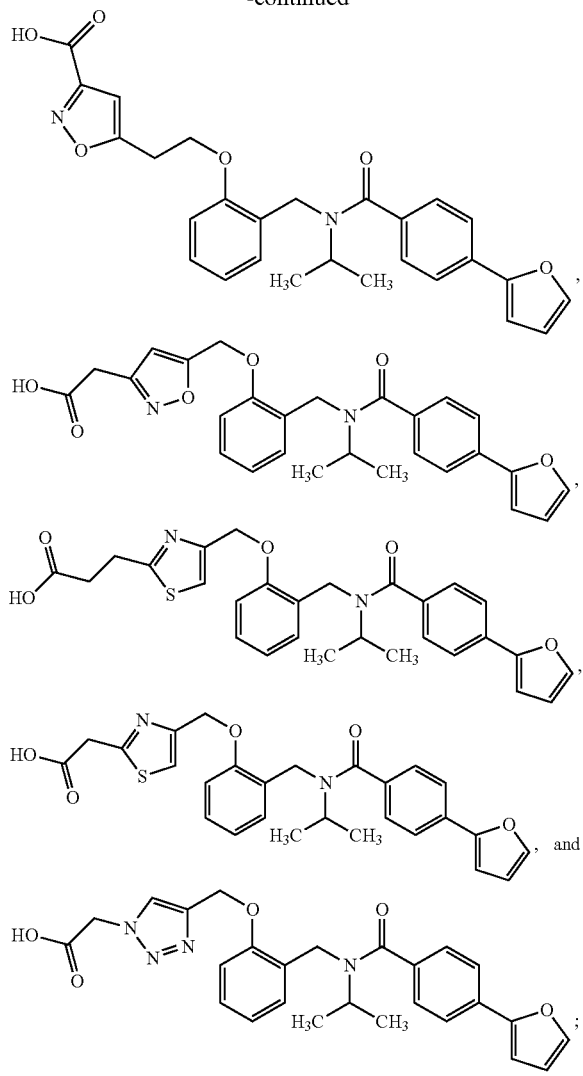

or a pharmaceutically acceptable salt thereof.

Exemplary substituents for Ar and Ring A are independently selected from halogen, $C_1$-$C_4$-alkyl, $C_1$-$C_4$-haloalkyl, CN, $C_1$-$C_4$-alkoxy, $C_1$-$C_4$-haloalkoxy, and $C_3$-$C_6$-cycloalkyl.

Pharmaceutical compositions of compounds of Formula (I) also are disclosed herein. Particular embodiments comprise a pharmaceutically acceptable excipient and one or more of the disclosed compounds, or a pharmaceutically acceptable salt thereof. The pharmaceutical compositions of the invention can be used in therapy, e.g., for treating a PPARδ-related disease or condition in a subject.

Another embodiment comprises treating a PPARδ-related disease or condition in a subject by administering to the subject a therapeutically effective amount of one or more disclosed compounds, or a pharmaceutically acceptable salt thereof, or a pharmaceutical composition comprising the compound(s).

Also provided herein is the use of one or more of the disclosed compounds, or a pharmaceutically acceptable salt thereof, or a pharmaceutical composition comprising one or more of the disclosed compounds, for the preparation of a medicament for the treatment of a PPARδ-related disease or condition.

In another embodiment, provided herein the disclosed compounds, or a pharmaceutically acceptable salt thereof, or a pharmaceutical composition comprising one or more of the disclosed compounds for use in treating a PPARδ-related disease or condition.

BRIEF DESCRIPTION OF THE DRAWINGS

FIGS. 1A and 1B are bar graphs showing recovery of damaged muscle fibers after injury.

FIG. 1C provides two images of transverse sections of TA of WT and TG animals, with damaged fibers stained by Evans Blue dye 5 days after the injury. FIG. 1D provides the proportion of stained area over the total cross-sectional area (CSA) of TA (n=5; **P<0.01). FIG. 1E provides quantification of Evans Blue stain at 12 hours after injury (n=3). FIG. 1F provides quantification of Evans Blue stain at 36 hours after injury (n=3).

FIGS. 1G-1J illustrate VP16-PPARδ transgenic animals that exhibit accelerated muscle regeneration after acute injury. All error bars are SEM. *P<0.05; P<0.01; *P<0.001; n.s.=not significant. FIG. 1G provides H&E stained transverse sections of injured transversus abdominis muscle (TVA) from wildtype (WT) and transgenic (TG) animals. Representative images are from 3, 5 and 7 days after injury. Arrows=regenerating fibers with centralized nuclei. Arrowheads=hollowed remains of basal lamina. Asterisks=uninjured fibers. FIG. 1H illustrates the average number of regenerating fibers per field. FIG. 1I illustrates the average CSA of regenerating myofiber (n=5 for day 5; n=1 for day 7). FIG. 1J illustrates the average CSA of regenerating myofiber, 21 days after injury (n=5).

FIG. 2A provides a GO classification of injury specific upregulated genes in TG (n=3). FIG. 2B shows the relative expression of regeneration markers in TG. FIG. 2C is a graph of relative expression versus days post injury, illustrating post injury temporal gene expression profiles of inflammatory marker CD68, measured by QPCR (n=5). FIG. 2D is a graph of relative expression versus days post injury, illustrating post injury temporal gene expression profiles of a myogenic marker MyoD by Q-PCR (n=5). FIG. 2E is a bar graph showing the Myh8 mRNA level 5 days post injury (n≥5).

FIG. 3A provides immunofluorescence staining for CD31 on transverse sections of uninjured TA from WT and TG animals. FIG. 3B provides quantification of CD31 positive capillary number (n=4). FIG. 3C illustrates the FGF1a mRNA level in TA of WT and TG by QPCR (n=5). FIG. 3D provides a Western blot for FGF1. FIG. 3E provides immunofluorescence staining for CD31 positive capillaries on transverse sections of TA, 5 days after the injury (n=3). FIG. 3F provides quantification for CD31 positive capillaries on transverse sections of TA, 5 days after the injury (n=3). FIG. 3G provides luciferase reporter assays of FGF1a promoter co-transfected with PPARδ with or without the ligand, GW501516.

FIGS. 4A-4E illustrate that the skeletal muscle specific activation of PPARδ increases the quiescent satellite cell pool. All error bars are SEM. *P<0.05; **P<0.01. FIG. 4A provides digital images of isolated myofibers from lateral gastrocnemius of 8-week-old nestin reporter mice with or without VP16-PPARδ transgene. FIG. 4B is a bar graph showing quantification of GFP+ satellite cells per unit length of myofiber (n=3). FIG. 4C is a bar graph showing the proportion of BrdU positive nuclei at 0.5, 1 and 2 days after injury (n=5). FIG. 4D is a bar graph showing VP16 mRNA levels in whole TA or satellite cells (SC) from WT and TG. FIG. 4E is a bar graph showing PPARδ mRNA levels in whole TA or satellite cells (SC) from WT and TG.

FIGS. 5A-5E illustrate that acute pharmacological activation of PPARδ confers regenerative advantage. *P<0.05; P<0.01; *P<0.001. All error bars are SEM. FIG. 5A is a series of bar graphs showing PPARδ target gene expression in TA after 9 day treatment with either vehicle or GW501516 (n=6). FIG. 5B provides digital images of transverse TA sections showing Evans Blue dye uptake 5 days after the injury. FIG. 5C is a bar graph showing the proportions of stained area (n=5) in the images of FIG. 5B. FIG. 5D is a bar graph showing the percentage of BrdU positive nuclei 2 days after injury (n=4). FIG. 5E is a series of bar graphs showing TNFα and F480 levels 3 days after injury measured by QPCR (n=6).

FIGS. 6A-6E show VP16-PPARδ transgenic animals exhibit accelerated muscle regeneration after the acute injury. All error bars are SEM. FIG. 6A shows werum creatine kinase levels in wildtype and VP16-PPARδ transgenic animals. FIG. 6B shows transverse sections of TA of WT and TG animals. Staining of damaged fibers by Evans Blue dye 5 days after the injury. FIG. 6C shows proportion of stained area over the total CSA of TA (n=5; **P<0.01). FIGS. 6D and 6E show quantification of Evans Blue stain at 12 and 36 hours after injury (n=3).

FIG. 7A shows transverse sections of TA of WT and TG animals. Staining of damaged fibers by Evans Blue 3 days after the injury.

FIG. 7B shows Injury dependent induction of PPARδ by QPCR (n=5).

FIG. 7C shows post injury temporal gene expression profiles of inflammatory markers TNFα.

DETAILED DESCRIPTION

Figure 1C:
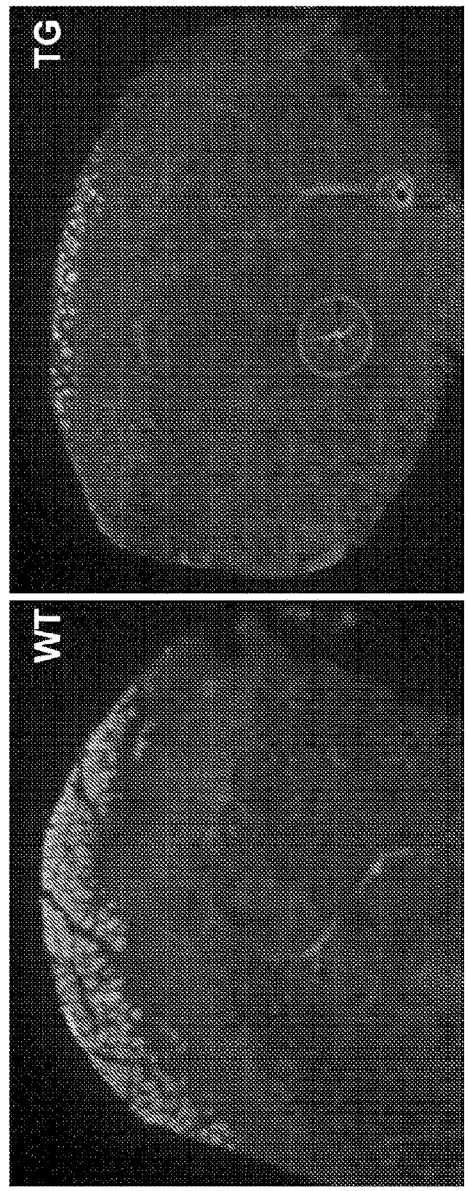
FIGS. 1C-1F show VP16-PPARδ transgenic animals exhibit accelerated muscle regeneration after acute injury. All error bars are SEM.

"Peroxisome proliferator-activated receptor delta" or "PPAR-δ", also known as peroxisome proliferator-activated receptor beta (PPAR-β) or as NR1C2 (nuclear receptor subfamily 1, group C, member 2), refers to a nuclear receptor protein that function as a transcription factor regulating the expression of genes. Ligands of PPARδ can promote myoblast proliferation after injury, such as injury to skeletal muscle. PPARδ (OMIM 600409) sequences are publically available, for example from GenBank® sequence database (e.g., accession numbers NP_001165289.1 (human, protein) NP_035275 (mouse, protein), NM_001171818 (human, nucleic acid) and NM_011145 (mouse, nucleic acid)).

Herein, the phrase "PPARδ agonist" refers to substances that increase the activity of PPARδ. Substances can be tested for their PPARδ agonist activity by contacting the substance with cells expressing PPARδ, detecting their binding with PPARδ and then detecting signals that serve as the indicator of the activation of PPARδ.

Definitions

The term "alkyl" used alone or as part of a larger moiety, such as "alkoxy", "haloalkyl", "cycloalkyl", "heterocycloalkyl", and the like, means saturated aliphatic straight-chain or branched monovalent hydrocarbon radical. Unless otherwise specified, an alkyl group typically has 1 to 4 carbon atoms, i.e., $C_1$-$C_4$-alkyl. As used herein, a "$C_1$-$C_4$-alkyl" group is means a radical having from 1 to 4 carbon atoms in a linear or branched arrangement.

"Alkoxy" means an alkyl radical attached through an oxygen linking atom, represented by —O-alkyl. For example, "$C_1$-$C_3$-alkoxy" includes methoxy, ethoxy, propoxy, and butoxy.

The terms "haloalkyl" and "haloalkoxy" mean alkyl or alkoxy, as the case may be, substituted with one or more halogen atoms.

The term "halogen" means fluorine or fluoro (F), chlorine or chloro (Cl), bromine or bromo (Br), or iodine or iodo (I).

The term "ring" used herein means a cyclic group, which includes cycloalkyl, heterocycloalkyl, aryl, and heteroaryl, each of which can be monocyclic, bicyclic (e.g., a bridged bicyclic ring) or polycyclic (e.g., tricyclic) for cycloalkyl and heterocycloalkyl, or fused for aryl and heteroaryl.

The term "aryl group" means an aromatic hydrocarbon ring system having six to fourteen carbon ring atoms. The term "aryl" may be used interchangeably with the terms "aryl ring", "aromatic ring", "aryl group", and "aromatic group". An aryl group typically has six to fourteen ring atoms. An "aryl group" also includes an aromatic ring fused to a non-aromatic carbocyclic ring. Examples of aryl groups include phenyl, naphthyl, anthracenyl, 1,2-dihydronaphthyl, 1,2,3,4-tetrahydronaphthyl, fluorenyl, indanyl, indenyl and the like. A "substituted aryl group" is substituted at any one or more substitutable ring atom, which is a ring carbon atom bonded to a hydrogen. "Arylene" is a bivalent aryl group, i.e., having two point of attachment to the remainder of the molecule.

"Cycloalkyl" means a 3-12 membered saturated aliphatic cyclic hydrocarbon radical. It can be monocyclic, bicyclic (e.g., a bridged bicyclic ring), polycyclic (e.g., tricyclic), or fused. For example, monocyclic $C_3$-$C_6$-cycloalkyl means a radical having from 3 to 6 carbon atoms arranged in a monocyclic ring. A $C_3$-$C_6$-cycloalkyl includes, but is not limited to, cyclopropyl, cyclobutyl, cyclopentyl, and cyclohexyl.

"Heterocycloalkyl" means a saturated or unsaturated non-aromatic 3 to 12 membered ring radical optionally containing one or more double bonds. It can be monocyclic, bicyclic (e.g., a bridged bicyclic ring), or polycyclic (e.g., tricyclic). The heterocycloalkyl contains 1 to 4 heteroatoms, which may be the same or different, selected from N, O or S. The heterocycloalkyl ring optionally contains one or more double bonds and/or is optionally fused with one or more non-aromatic carbocyclic rings, aromatic rings (e.g., phenyl ring) or heteroaryl rings. "5- or 6-membered monocyclic heterocycloalkyl" means a radical having from 5 or 6 ring atoms (including 1 to 3 ring heteroatoms) arranged in a monocyclic ring. Examples of heterocycloalkyl include, but are not limited to, morpholinyl, thiomorpholinyl, pyrrolidinonyl, pyrrolidinyl, piperidinyl, piperazinyl, hydantoinyl, valerolactamyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, and tetrahydrothiopyranyl.

The term "heteroaryl", "heteroaromatic", "heteroaryl ring", "heteroaryl group", "heteroaromatic ring", and "heteroaromatic group", are used interchangeably herein. "Heteroaryl" when used alone or as part of a larger moiety as in "heteroaralkyl" or "heteroarylalkoxy", refers to aromatic ring groups having five to fourteen ring atoms selected from carbon and at least one (typically 1 to 4, more typically 1 or 2) heteroatoms (e.g., oxygen, nitrogen or sulfur). "Heteroaryl" includes monocyclic rings and polycyclic rings in which a monocyclic heteroaromatic ring is fused to one or more other aromatic or heteroaromatic rings. "Heterorylene" is a bivalent heteroaryl group, i.e., having two point of attachment to the remainder of the molecule.

"Monocyclic 5- or 6-membered heteroaryl" means a monocyclic aromatic ring system having five or six ring atoms selected from carbon and at least one (typically 1 to 3, more typically 1 or 2) heteroatoms (e.g., oxygen, nitrogen or sulfur). Examples of monocyclic 5-6 membered heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), isothiazolyl, triazolyl (e.g., 2-triazolyl, 5-triazolyl), tetrazolyl (e.g., tetrazolyl), and thienyl (e.g., 2-thienyl, 3-thienyl). Examples of polycyclic aromatic heteroaryl groups include carbazolyl, benzimidazolyl, benzothienyl, benzofuranyl, isobenzofuranyl, indolyl, benzotriazolyl, benzothiazolyl, benzoxazolyl, quinolinyl, isoquinolinyl, indazolyl, isoindolyl, acridinyl, or benzisoxazolyl. A "substituted heteroaryl group" is substituted at any one or more substitutable ring atom, which is a ring carbon or ring nitrogen atom bonded to a hydrogen.

The term "fused" as used herein refers to any combination of two or more cycloalkyl, heterocycloalkyl, aryl, and/or heteroaryl rings that share two adjacent ring atoms.

The term "bridged" as used herein refers to two carbocyclic refers to any combination of two cycloalkyl or heterocycloalkyl rings that share three or more adjacent ring atoms.

If a group is described as being "substituted", a non-hydrogen substituent is in the place of a hydrogen substituent on a carbon, sulfur or nitrogen of the substituent. Thus, for example, a substituted alkyl is an alkyl wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent can be identical or different (unless otherwise stated).

If a group is described as being "optionally substituted", the substituent can be either (1) not substituted, or (2) substituted.

If a list of groups are collectively described as being optionally substituted by one or more of a list of substituents, the list can include: (1) unsubstitutable groups, (2) substitutable groups that are not substituted by the optional substituents, and/or (3) substitutable groups that are substituted by one or more of the optional substituents.

If a group is described as being optionally substituted with up to a particular number of non-hydrogen substituents, that group can be either (1) not substituted; or (2) substituted by up to that particular number of non-hydrogen substituents or by up to the maximum number of substitutable positions on the substituent, whichever is less. Thus, for example, if a group is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions.

Unless otherwise indicated, suitable substituents for substituted alkyl, cycloalkyl, heterocycloalkyl, aryl, and heteroaryl groups include the groups represented by halogen, —CN, —OR$^c$, —NR$^a$R$^b$, —C(=O)OR$^c$, —OC(=O)OR$^c$, —C(=O)NR$^e$R$^f$, —NR$^d$C(=O)R$^c$, —NR$^d$(C=O)OR$^c$, —O(C=O)NR$^e$R$^f$, —NR$^d$(C=O)NR$^e$R$^f$, —C(=O)R$^c$, (C$_1$-C$_6$)alkyl, cycloalkyl, cycloalkyl(C$_1$-C$_4$)alkyl, heterocycloalkyl, heterocycloalkyl(C$_1$-C$_4$)alkyl, aryl, aryl(C$_1$-C$_4$)alkyl, heteroaryl, and heteroaryl(C$_1$-C$_4$)alkyl, wherein R$^a$ and R$^b$ are each independently selected from —H and (C$_1$-C$_6$)alkyl, optionally substituted with 1 to 3 substituents independently selected from halogen, hydroxy, —NR$^g$R$^h$ and (C$_1$-C$_3$)alkoxy; R$^c$ is —H or (C$_1$-C$_6$)alkyl, optionally substituted with 1 to 3 substituents independently selected from halogen, —NR$^g$R$^h$, hydroxy and (C$_1$-C$_3$)alkoxy; R$^d$ is —H or (C$_1$-C$_6$)alkyl, optionally substituted with 1 to 3 substituents independently selected from halogen, —NR$^g$R$^h$, hydroxy and (C$_1$-C$_3$)alkoxy; and R$^e$ and R$^f$ are each independently selected from —H and (C$_1$-C$_6$)alkyl optionally substituted with 1 to 3 substituents independently selected from halogen, —NR$^g$R$^h$, hydroxy and (C$_1$-C$_3$) alkoxy; or R$^e$ and R$^f$, together with the nitrogen to which they are attached, form a 3-8 membered ring optionally substituted with 1 to 3 substituents independently selected from halogen, —NR$^g$R$^h$, —CN, (C$_1$-C$_6$)alkyl, halo(C$_1$-C$_6$) alkyl, (C$_1$-C$_3$)alkoxy, halo(C$_1$-C$_3$)alkoxy, and (C$_1$-C$_3$) alkoxy(C$_1$-C$_6$)alkyl. Each of the (C$_1$-C$_6$)alkyl, cycloalkyl, cycloalkyl(C$_1$-C$_3$)alkyl, heterocycloalkyl, heterocycloalkyl (C$_1$-C$_3$)alkyl, aryl, aryl(C$_1$-C$_3$)alkyl, heteroaryl and heteroaryl(C$_1$-C$_3$)alkyl substituents is optionally substituted with halogen, —NO$_2$, —CN, —NR$^d$C(=O)R$^c$, —NR$^g$R$^h$, (C$_1$-C$_4$)alkyl, (C$_1$-C$_4$)haloalkyl, (C$_1$-C$_4$)alkoxy(C$_1$-C$_4$) alkyl, (C$_1$-C$_4$)alkoxy, and (C$_1$-C$_4$)haloalkoxy, wherein R$^g$ and R$^h$ are each independently selected from —H, (C$_1$-C$_6$) alkyl, halo(C$_1$-C$_6$)alkyl, hydroxy(C$_1$-C$_6$)alkyl and (C$_1$-C$_3$) alkoxy(C$_1$-C$_6$)alkyl. Suitable substituents for a substituted alkyl, cycloalkyl, heterocycloalkyl can also include =O. Alternatively, suitable substituents for substituted alkyl, cycloalkyl, heterocycloalkyl, aryl, and heteroaryl groups include alkyl, haloalkyl, alkoxy, haloalkoxy, cyano, and halogen.

Compounds having one or more chiral centers can exist in various stereoisomeric forms. Stereoisomers are compounds that differ only in their spatial arrangement. When a disclosed compound is named or depicted by structure without indicating stereochemistry, it is understood that the name or the structure encompasses one or more of the possible stereoisomers, or geometric isomers, or a mixture of the encompassed stereoisomers or geometric isomers.

When a geometric isomer is depicted by name or structure, it is to be understood that the geometric isomeric purity of the named or depicted geometric isomer is at least 60%, 70%, 80%, 90%, 99% or 99.9% pure by weight. Geometric isomeric purity is determined by dividing the weight of the named or depicted geometric isomer in the mixture by the total weight of all of the geometric isomers in the mixture. It includes a single stereoisomers free of the other stereoisomers, or, alternatively, mixtures of the stereoisomers.

Racemic mixture means 50% of one enantiomer and 50% of is corresponding enantiomer. When a compound with one chiral center is named or depicted without indicating the stereochemistry of the chiral center, it is understood that the name or structure encompasses both possible enantiomeric forms (e.g., both enantiomerically-pure, enantiomerically-enriched or racemic) of the compound. When a compound with two or more chiral centers is named or depicted without indicating the stereochemistry of the chiral centers, it is understood that the name or structure encompasses all possible diasteriomeric forms (e.g., diastereomerically pure, diastereomerically enriched and equimolar mixtures if one or more diastereomers e.g., racemic mixtures) of the compound.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers also can be obtained from diastereomerically- or enantiomerically-pure intermediates, reagents, and catalysts by well-known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Included in the present teachings are pharmaceutically acceptable salts of the compounds disclosed herein. The disclosed compounds have basic amine groups and therefore can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, nitric, and sulfuric acids) and of organic acids (such as, e.g., acetic acid, benzenesulfonic, benzoic, methanesulfonic, and p-toluenesulfonic acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

As used herein, the term "pharmaceutically-acceptable salt" refers to pharmaceutical salts that are, within the scope of sound medical judgment, suitable for use in contact with the tissues of humans and lower animals without undue toxicity, irritation, and allergic response, and are commensurate with a reasonable benefit/risk ratio. Pharmaceutically-acceptable salts are well known in the art. For example, S. M. Berge, et al. describes pharmacologically acceptable salts in *J. Pharm. Sci.*, 1977, 66:1-19.

The neutral forms of the compounds of the invention are regenerated from their corresponding salts by contacting the salt with a base or acid and isolating the parent compound in the conventional manner. The parent form of the compound may differ from the various salt forms in certain physical properties, such as solubility in polar solvents. The neutral forms of compounds disclosed herein also are included in the invention.

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

As used herein, the terms "co-administration", "administered in combination with", and their grammatical equivalents, are meant to encompass administration of two or more therapeutic agents to a single subject, and are intended to include treatment regimens in which the agents are administered by the same or different route of administration or at the same or different times. In some embodiments the one or more compounds described herein will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

Generally, an effective amount of a compound taught herein varies depending upon various factors, such as the given drug or compound, the pharmaceutical formulation, the route of administration, the type of disease or disorder, the identity of the subject or host being treated, and the like, but can nevertheless be routinely determined by one skilled in the art. An effective amount of a compound of the present teachings may be readily determined by one of ordinary skill by routine methods known in the art.

The term "effective amount" or "therapeutically effective amount" means an amount when administered to the subject which results in beneficial or desired results, including clinical results, e.g., inhibits, suppresses or reduces the symptoms of the condition being treated in the subject as compared to a control. For example, a therapeutically effective amount can be given in unit dosage form (e.g., 1 mg to about 50 g per day, alternatively from 10 mg to about 5 grams per day; and in another alternatively from 10 mg to 1 gram per day).

The particular mode of administration and the dosage regimen will be selected by the attending clinician, taking into account the particulars of the case (e.g. the subject, the disease, the disease state involved, the particular treatment, and whether the treatment is prophylactic). Treatment can involve daily or multi-daily or less than daily (such as weekly or monthly etc.) doses over a period of a few days to months, or even years. However, a person of ordinary skill in the art would immediately recognize appropriate and/or equivalent doses looking at dosages of approved compositions for treating a PPARδ related disease using the disclosed PPAR agonists for guidance.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

"Pharmaceutically acceptable excipient" and "pharmaceutically acceptable carrier" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

Compounds of the Invention

Disclosed herein are embodiments of a compound having general Formula (I):

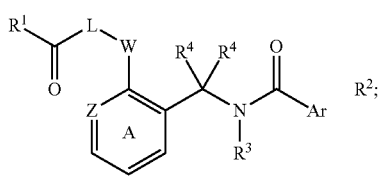

or a pharmaceutically acceptable salt thereof.

In a $1^{st}$ embodiment, the compound has the structure of Formula (II):

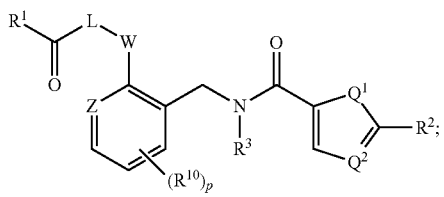

or a pharmaceutically acceptable salt thereof, wherein $Q^1$ is $CR^{20}=CR^{20}$, $N=CH$, $CH=N$,

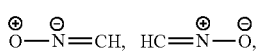

or S; $Q^2$ is $CR^{20}$ or N; p is an integer having a value of 1 or 2; each $R^{10}$ is independently hydrogen, halogen, $C_1$-$C_4$-alkyl, $C_1$-$C_4$-haloalkyl, CN, $C_1$-$C_4$-alkoxy, $C_1$-$C_4$-haloalkoxy, or $C_3$-$C_6$-cycloalkyl; each $R^{20}$ is independently hydrogen, halogen, $C_1$-$C_4$-alkyl, CN, or $C_1$-$C_4$-alkoxy; and the remainder of the variables are as defined for Formula (I).

In a $2^{nd}$ embodiment, the compound of the invention has the structure of any one of Formulas (III)-(IX):

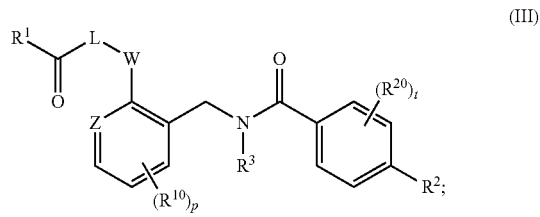

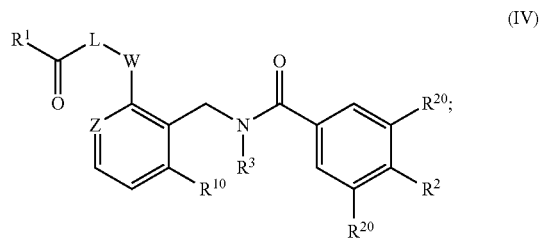

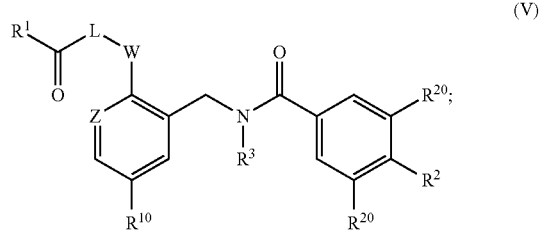

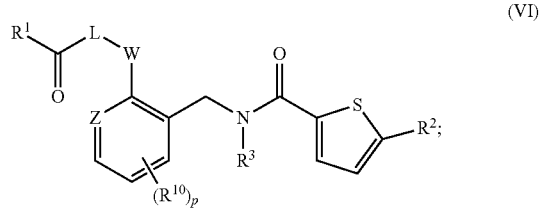

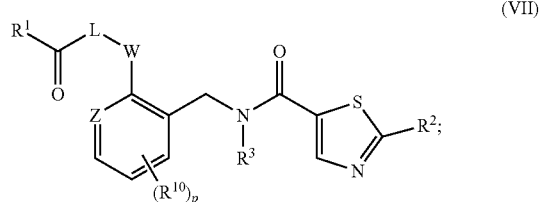

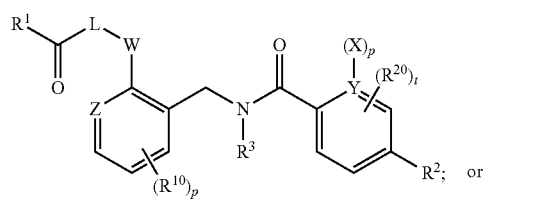

-continued

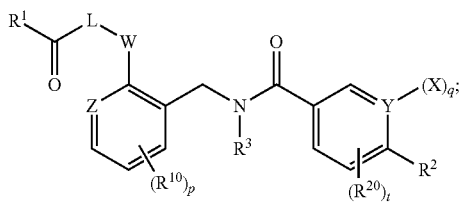
(IX)

or a pharmaceutically acceptable salt thereof.

In Formula (III), t is an integer having a value of 1 or 2; and the remainder of the variables are as defined for Formula (II) in the 1$^{st}$ embodiment.

In Formulas (IV)-(VII), t is an integer having a value of 1 or 2; and the remainder of the variables are as defined for Formula (II) in the 1$^{st}$ embodiment.

In Formula (VIII) and (IX), q is an integer having a value of 0 or 1; X is O$^{\ominus}$; Y is N$^{\oplus}$ when q is 1; or Y is N when q is 0; and the remainder of the variables are as defined for Formula (II) in the 1$^{st}$ embodiment. In certain embodiments, q is 0. Alternatively, q is 1.

In a 3$^{rd}$ embodiment, the compound has the structure of any one of Formulas (X)-(XIII):

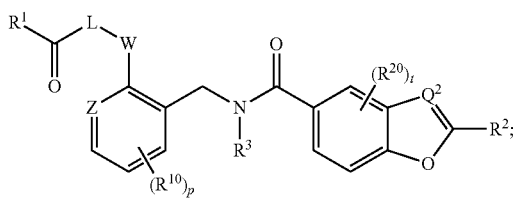
(X)

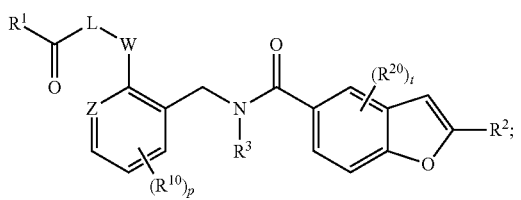
(XI)

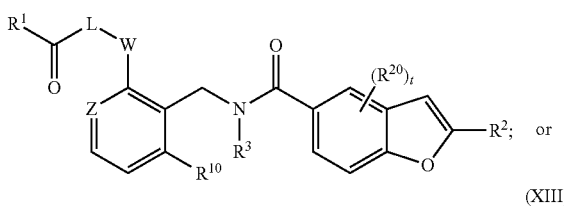
(XII)

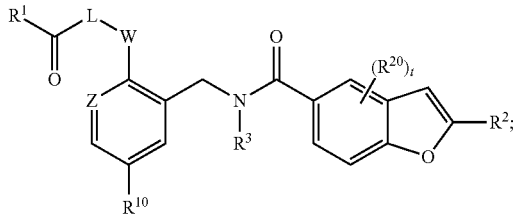
(XIII)

or a pharmaceutically acceptable salt thereof.

In Formula (X)-(XIII), Q$^2$ (where present) is CR$^{20}$ or N; p and t are integers each independently having a value of 1 or 2; each R$^{10}$ is independently hydrogen, halogen, C$_1$-C$_4$-alkyl, C$_1$-C$_4$-haloalkyl, CN, C$_1$-C$_4$-alkoxy, C$_1$-C$_4$-haloalkoxy, or C$_3$-C$_6$-cycloalkyl; each R$^{20}$ is independently hydrogen, halogen, C$_1$-C$_4$-alkyl, CN, or C$_1$-C$_4$-alkoxy; and the remainder of the variables are as defined for Formula (I).

In an 4$^{th}$ embodiment, the compound has the structure of any one of Formulas (I)-(XIII), wherein Z is CH, and the remainder of the variables are as defined in the 1$^{st}$ embodiment, the 2$^{nd}$ embodiment, or the 3$^{rd}$ embodiment.

In a 5$^{th}$ embodiment, the compound has the structure of any one of Formulas (I)-(XIII), wherein L is selected from the group consisting of:

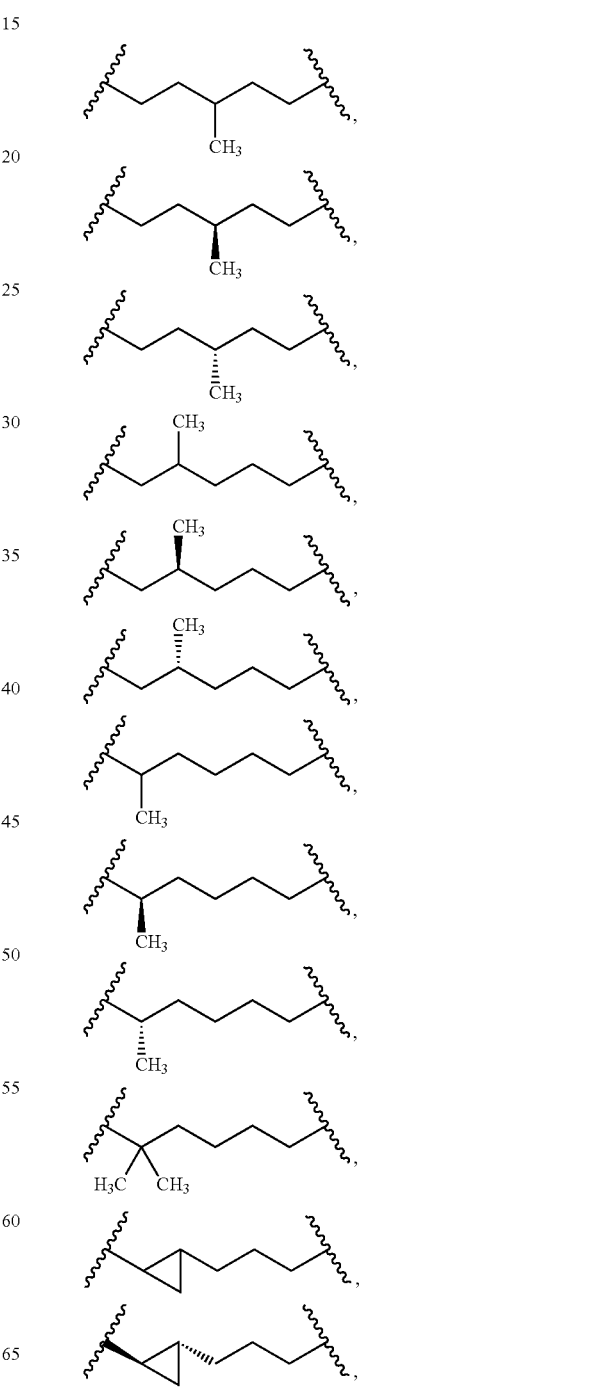

17

-continued

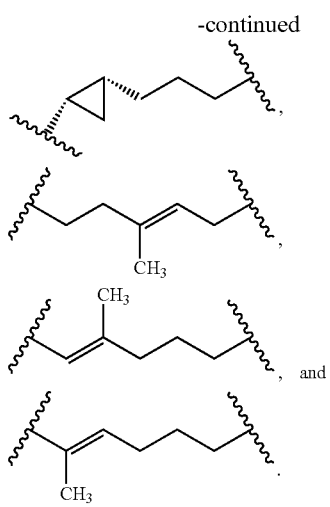

and the remainder of the variables are as defined in the 1st embodiment, the 2nd embodiment, the 3rd embodiment, or the 4th embodiment.

In a 6th embodiment, the compound has the structure of any one of Formulas (I)-(XIII), wherein L is selected from the group consisting of:

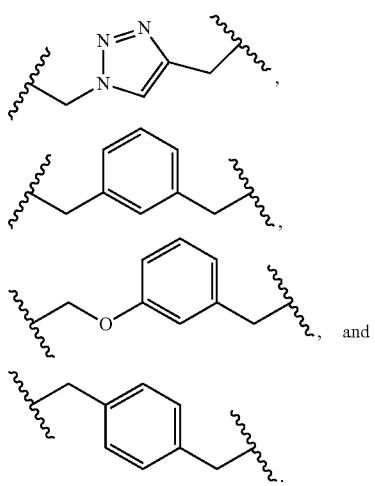

and the remainder of the variables are as defined in the 1st embodiment, the 2nd embodiment, the 3rd embodiment, or the 4th embodiment.

In a 7th embodiment, the compound has the structure of any one of Formulas (I)-(XIII), wherein W is $CH_2$, CH=CH, or C≡C, and the remainder of the variables are as defined in the 1st embodiment, the 2nd embodiment, the 3rd embodiment, the 4th embodiment, or the 5th embodiment.

In a 8th embodiment, the compound has the structure of any one of Formulas (I)-(XIII), wherein W is O, and the remainder of the variables are as defined in the 1st embodiment, the 2nd embodiment, the 3rd embodiment, the 4th embodiment, the 5th embodiment, or the 6th embodiment.

In an 9th embodiment, the compound has the structure of any one of Formulas (I)-(XIII), wherein $R^3$ is methyl, and the remainder of the variables are as defined in the 8th embodiment.

In a 10th embodiment, the compound has the structure of any one of Formulas (I)-(XIII), wherein $R^2$ is phenyl,

18 furanyl, thienyl, —≡—$CF_3$, $OCF_3$, or $OCHF_2$, wherein the phenyl can be optionally substituted with halogen, CN, $C_1$-$C_4$-alkyl, OH, $C_1$-$C_4$ alkoxy, formyl, acetyl, acetoxy, or carboxyl, and wherein the furanyl and the thienyl each can be optionally substituted with $C_1$-$C_4$-alkyl; and the remainder of the variables are as defined in the 7th embodiment and the 8th embodiment. In certain embodiments, $R^2$ is unsubstituted phenyl, unsubstituted furanyl, 5-methyl-2-furanyl, —≡—$CF_3$, $OCF_3$, or $OCHF_2$; and the remainder of the variables are as defined in the 8th embodiment or the 9th embodiment.

In an 11th embodiment, the compound has the structure of any one of Formulas (I)-(XIII), wherein L is selected from the group consisting of:

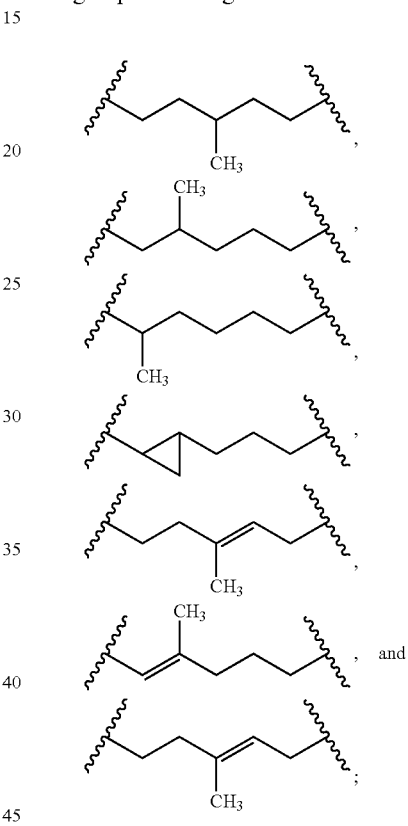

and the remainder of the variables are as defined in the 8th embodiment, the 9th embodiment, or the 10th embodiment. In preferred embodiments, L is

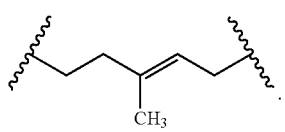 [SMILES: *C/C=C(\C)CC*]

In an 12th embodiment, the compound has the structure of any one of Formulas (I)-(XIII), wherein $R^{10}$ is hydrogen, halogen, methyl, CN, $OCH_3$, $CF_3$, $OCF_3$, $OCHF_2$, or cyclopropyl; and the remainder of the variables are as defined in the 8th embodiment, the 9th embodiment, the 10th embodiment, or the 11th embodiment. In particular embodiments, $R^{10}$ is hydrogen, fluorine, bromine, methyl, or $OCH_3$; and the remainder of the variables are as defined in the 8th embodiment, the 9th embodiment, the 10th embodiment, or the 11th embodiment.

In a 13th embodiment, the compound has the structure of any one of Formulas (I)-(XIII), wherein $R^{20}$ is hydrogen or halogen; and the remainder of the variables are as defined in any one of the 8th embodiment, the 9th embodiment, the 10th embodiment, the 11th embodiment, or the 12th embodiment. In certain embodiments, $R^{20}$ is hydrogen, fluorine, or chlorine; and the remainder of the variables are as defined in the 8th embodiment, the 9th embodiment, the 10th embodiment, the 11th embodiment, or the 12th embodiment.

In a 14th embodiment, the compound has the structure of any one of Formulas (X)-(XIII), wherein $R^2$ is hydrogen or $C_1$-$C_4$-alkyl, and the remainder of the variables are defined in any one of the 8th embodiment, the 9th embodiment, the 10th embodiment, the 11th embodiment, the 12th embodiment, or the 13th embodiment. In particular embodiments, $R^2$ is hydrogen or methyl, and the remainder of the variables are defined in the 8th embodiment, the 9th embodiment, the 10th embodiment, the 11th embodiment, the 12th embodiment, or the 13th embodiment.

In a 15th embodiment, the compound has the structure of any one of Formulas (I)-(XIII), wherein $R^2$ is unsubstituted furanyl, and the remainder of the variables are defined in any one of the 8th embodiment, the 9th embodiment, the 10th embodiment, the 11th embodiment, the 12th embodiment, the 13th embodiment. Alternatively, the compound has the structure of any one of Formulas (I)-(XIII), wherein $R^2$ is 5-methyl-2-furanyl, and the remainder of the variables are defined in the 8th embodiment, the 9th embodiment, the 10th embodiment, the 11th embodiment, the 12th embodiment, or the 13th embodiment.

In a preferred embodiment, the compound has the structure of Formula (III), wherein $R^1$ is OH; W is O; Z is CH; L is

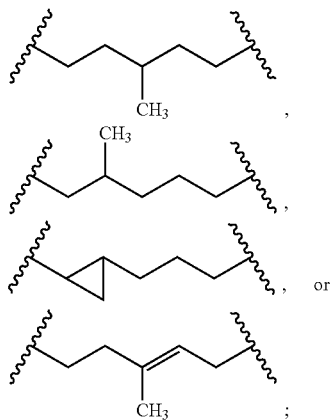

$R^2$ is unsubstituted furanyl or 5-methyl-2-furanyl; $R^3$ is methyl; p and t are 1; $R^{10}$ is hydrogen, fluorine, bromine, methyl, or $OCH_3$; and $R^{20}$ is hydrogen, fluorine, or chlorine.

In certain embodiments, the invention is any one of the compounds depicted in the exemplification section of the instant application; pharmaceutically acceptable salts as well as the neutral forms of these compounds also are included in the invention. Specifically, the invention is any one of the compounds depicted in Examples 8A-8BB; pharmaceutically acceptable salts as well as the neutral forms of these compounds also are included in the invention. In preferred embodiments, the invention is any one of Compounds 8a-8bb; pharmaceutically acceptable salts as well as the neutral forms of these compounds also are included in the invention.

Methods of Treatment

Methods of treating a PPARδ-related disease or condition in a subject are disclosed. The methods can include administering to the subject a therapeutically effective amount of one or more compounds or compositions provided herein.

In one embodiment, the PPARδ-related disease is a mitochondrial disease. Examples of mitochondrial diseases include, but are not limited to, Alpers's Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, and retinitis pigmentosa, and Pearson Syndrome.

In other embodiments, the PPARδ-related disease is a vascular disease (such as a cardiovascular disease or any disease that would benefit from increasing vascularization in tissues exhibiting impaired or inadequate blood flow). In other embodiments, the PPARδ-related disease is a muscular disease, such as a muscular dystrophy. Examples of muscular dystrophy include but are not limited to Duchenne muscular dystrophy, Becker muscular dystrophy, limb-girdle muscular dystrophy, congenital muscular dystrophy, facioscapulohumeral muscular dystrophy, myotonic muscular dystrophy, oculopharyngeal muscular dystrophy, distal muscular dystrophy, and Emery-Dreifuss muscular dystrophy.

In some embodiments, the PPARδ-related disease or condition is a demyelinating disease, such as multiple sclerosis, Charcot-Marie-Tooth disease, Pelizaeus-Merzbacher disease, encephalomyelitis, neuromyelitis optica, adrenoleukodystrophy, or Guillian-Barre syndrome.

In other embodiments, the PPARδ-related disease is a metabolic disease. Examples of metabolic diseases include but are not limited to obesity, hypertriglyceridemia, hyperlipidemia, hypoalphalipoproteinemia, hypercholesterolemia, dyslipidemia, Syndrome X, and Type II diabetes mellitus.

In yet other embodiments, the PPARδ-related disease is a muscle structure disorder. Examples of a muscle structure disorders include, but are not limited to, Bethlem myopathy, central core disease, congenital fiber type disproportion, distal muscular dystrophy (MD), Duchenne & Becker MD, Emery-Dreifuss MD, facioscapulohumeral MD, hyaline body myopathy, limb-girdle MD, a muscle sodium channel disorders, myotonic chondrodystrophy, myotonic dystrophy, myotubular myopathy, nemaline body disease, oculopharyngeal MD, and stress urinary incontinence.

In still other embodiments, the PPARδ-related disease is a neuronal activation disorder. Examples of neuronal activation disorders include, but are not limited to, amyotrophic lateral sclerosis, Charcot-Marie-Tooth disease, Guillain-Barre syndrome, Lambert-Eaton syndrome, multiple sclerosis, myasthenia gravis, nerve lesion, peripheral neuropathy, spinal muscular atrophy, tardy ulnar nerve palsy, and toxic myoneural disorder.

In other embodiments, the PPARδ-related disease is a muscle fatigue disorder. Examples of muscle fatigue disorders include, but are not limited to chronic fatigue syndrome, diabetes (type I or II), glycogen storage disease, fibromyalgia, Friedreich's ataxia, intermittent claudication, lipid storage myopathy, MELAS, mucopolysaccharidosis, Pompe disease, and thyrotoxic myopathy.

In some embodiments, the PPARδ-related disease is a muscle mass disorder. Examples of muscle mass disorders include, but are not limited to, cachexia, cartilage degeneration, cerebral palsy, compartment syndrome, critical illness myopathy, inclusion body myositis, muscular atrophy (disuse), sarcopenia, steroid myopathy, and systemic lupus erythematosus.

In other embodiments, the PPARδ-related disease is a beta oxidation disease. Examples of beta oxidation diseases include, but are not limited to, systemic carnitine transporter, carnitine palmitoyltransferase (CPT) II deficiency, very long-chain acyl-CoA dehydrogenase (LCHAD or VLCAD) deficiency, trifunctional enzyme deficiency, medium-chain acyl-CoA dehydrogenase (MCAD) deficiency, short-chain acyl-CoA dehydrogenase (SCAD) deficiency, and riboflavin-responsive disorders of β-oxidation (RR-MADD).

In some embodiments, the PPARδ-related disease is a vascular disease. Examples of vascular diseases include, but are not limited to, peripheral vascular insufficiency, peripheral vascular disease, intermittent claudication, peripheral vascular disease (PVD), peripheral artery disease (PAD), peripheral artery occlusive disease (PAOD), and peripheral obliterative arteriopathy.

In other embodiments, the PPARδ-related disease is an ocular vascular disease. Examples of ocular vascular diseases include, but are not limited to, age-related macular degeneration (AMD), stargardt disease, hypertensive retinopathy, diabetic retinopathy, retinopathy, macular degeneration, retinal haemorrhage, and glaucoma.

In yet other embodiments, the PPARδ-related disease is a muscular eye disease. Examples of muscular eye diseases include, but are not limited to, strabismus (crossed eye/wandering eye/walleye ophthalmoparesis), progressive external ophthalmoplegia, esotropia, exotropia, a disorder of refraction and accommodation, hypermetropia, myopia, astigmatism, anisometropia, presbyopia, a disorders of accommodation, or internal ophthalmoplegia.

In yet other embodiments, the PPARδ-related disease is a metabolic disease. Examples of metabolic disorders include, but are not limited to, hyperlipidemia, dyslipidemia, hyperchlolesterolemia, hypertriglyceridemia, HDL hypocholesterolemia, LDL hypercholesterolemia and/or HLD non-cholesterolemia, VLDL hyperproteinemia, dyslipoproteinemia, apolipoprotein A-I hypoproteinemia, atherosclerosis, disease of arterial sclerosis, disease of cardiovascular systems, cerebrovascular disease, peripheral circulatory disease, metabolic syndrome, syndrome X, obesity, diabetes (type I or II), hyperglycemia, insulin resistance, impaired glucose tolerance, hyperinsulinism, diabetic complication, cardiac insufficiency, cardiac infarction, cardiomyopathy, hypertension, non-alcoholic fatty liver disease (NAFLD), nonalcoholic steatohepatitis (NASH), thrombus, Alzheimer disease, neurodegenerative disease, demyelinating disease, multiple sclerosis, adrenal leukodystrophy, dermatitis, psoriasis, acne, skin aging, trichosis, inflammation, arthritis, asthma, hypersensitive intestine syndrome, ulcerative colitis, Crohn's disease, and pancreatitis.

In still other embodiments, the PPARδ-related disease is cancer. Examples of cancer include, but are not limited to, cancers of the colon, large intestine, skin, breast, prostate, ovary, and/or lung.

Pharmaceutical Compositions and Administration Thereof
Additional Therapeutic Agents Pharmaceutical compositions are disclosed that include one or more compounds provided herein (such as 1, 2, 3, 4 or 5 of such compounds), and typically at least one additional substance, such as an excipient, a known therapeutic other than those of the present disclosure, and combinations thereof. In some embodiments, the disclosed PPAR agonists can be used in combination with other agents known to have beneficial activity with the disclosed PPAR agonists. For example, disclosed compounds can be administered alone or in combination with: one or more other PPAR agonists, such as a thiazolidinedione, including rosiglitazone, pioglitazone, troglitazone, and combinations thereof, or a sulfonylurea agent or a pharmaceutically acceptable salt thereof, such as tolbutamide, tolazamide, glipizide, carbutamide, glisoxepide, glisentide, glibornuride, glibenclamide, gliquidone glimepiride, gliclazide and the pharmaceutically acceptable salts of these compounds, or muraglitazar, farglitazar, naveglitazar, netoglitazone, rivoglitazone, K-111, GW-677954, (–)-Halofenate, acid, arachidonic acid, clofbrate, gemfibrozil, fenofibrate, ciprofibrate, bezafibrate, lovastatin, pravastatin, simvastatin, mevastatin, fluvastatin, indomethacin, fenoprofen, ibuprofen, and the pharmaceutically acceptable salts of these compounds.

In one embodiment, disclosed compounds may be administered in combination with dexamphetamine, amphetamine, mazindole or phentermine; and administered in combination with medicaments having an anti-inflammatory effect.

Further, when used for the treatment of a metabolic condition, the pharmaceutical compositions provided herein can be administered as a combination therapy with one or more pharmacologically active substances having favorable effects on metabolic disturbances or disorders. For example, the disclosed pharmaceutical compositions may be administered in combination with RXR agonists for treating metabolic and cardiovascular diseases medicaments, which lower blood glucose; antidiabetics, such as insulins and insulin derivatives, including Lantus, Apidra, and other fast-acting insulins, and GLP-1 receptor modulators; active ingredients for treating dyslipidemias; anti-atherosclerotic medicaments; anti-obesity agents; anti-inflammatory active ingredients; active ingredients for treating malignant tumors; anti-thrombotic active ingredients; active ingredients for treating high blood pressure; active ingredients for treating heart failure, and combinations thereof.

Working Examples

Skeletal muscle relies on the resident progenitor cells, the satellite cells, for postnatal growth and regeneration. Therefore, maintaining an adequate number and proper function of satellite cells is critical for muscle to appropriately response to damage. While endurance exercise promotes adaptive responses in the muscle, including an increase in the satellite cell number, it is not known whether transcriptionally directed "endurance exercise training" has similar effects. Here it is shown that mice harboring constitutively active PPARδ in skeletal muscle displayed an accelerated regenerative process in muscle after an acute injury. Gene expression analyses showed earlier resolution of the inflammatory response and induction of myogenic markers, indicating that PPARδ activation induces a temporal shift in the regenerative process. Notably, a significant increase in the number of satellite cells was found in mice with constitutively active PPARδ expressed in skeletal muscle, consistent with the observed increase in proliferating cell number after the injury. PPARδ activation induced the expression of FGF1, which is known to be involved in muscle development and regeneration. In particular, PPARδ up-regulates FGF1a isoform, which may be responsible for supporting cell proliferation and reestablishment of vasculature to augment the regenerative process. Furthermore, the restoration of fiber integrity was improved in wild-type mice after acute treatment with the PPARδ synthetic ligand, GW501516. Collectively, these findings allude to the therapeutic potential of PPARδ, to accelerate the recovery from acute muscle injury.

Activation of peroxisome proliferator activated receptor δ (PPARδ) induces a fiber type switch toward a more oxidative phenotype, altering both metabolic and functional output of the muscle (Wang et al., *PLoS Biol* 2(10):e294. Erratum in: *PLoS Biol.* 2005 January; 3(1):e61 (2004); Luquet et al., *FASEB J* 17(15):2299-2301 (2003)). Specifically, PPARδ-mediated muscle remodeling translates into supernatural physical endurance, and protection against diet-induced obesity and symptoms of metabolic disorders that ensue (Wang et al., *PLoS Biol* 2(10):e294. Erratum in: *PLoS Biol.* 2005 January; 3(1):e61 (2004); Wang et al., *Cell* 113:159-170 (2003)). Furthermore, pharmacological activation of PPARδ and exercise training synergistically enhance oxidative fibers and running endurance (Narkar V A et al., *Cell* 134(3):405-415 (2008)). Exercise confers a myriad of healthful benefits to the body, including improvement of atrophic and disease conditions (Nicastro et al., *Braz J Med Biol Res* 44(11):1070-9 (2011); Markert et al., *Muscle Nerve* 43(4):464-78 (2011)). Recently, endurance exercise alone has been shown to improve ageing induced decrease in satellite cell number and their myogenic capacity (Shefer et al., *PLoS One* 5(10):e13307 (2010)).

It is demonstrated herein that both genetic and pharmacological activation of PPARδ promote muscle regeneration in an acute thermal injury mouse model. PPARδ activation during regeneration expedites resolution of inflammatory response and restoration of contractile proteins. Interestingly, acute pharmacological activation of PPARδ by oral administration of a synthetic ligand, GW501516, is sufficient to confer similar benefits during muscle regeneration after an acute injury. Based on these observations, a novel role of PPARδ during adult muscle regeneration and its use as a therapeutic target to enhance regenerative efficiency of skeletal muscle is provided.

EXEMPLIFICATION

Example 1

Experimental Procedures

A. Animals

VP16-PPARδ mice (Wang et al., *Cell* 113:159-170 (2003)) were bred to CB6F1 strain (Jackson Laboratories) and used as heterozygotes in experiments. The non-transgenic littermates served as controls. All experiments were performed when animals were 8 weeks of age. Nestin-GFP mice (Mignone et al., *J Comp Neurol* 469(3):311-324 (2004)) were kindly provided by Dr. Fred Gage at the Salk Institute for Biological Studies.

B. Freeze Burn Injury

TA muscles were injured according to previously published methods with a few modifications (Brack et al., *Science* 317(5839):807-810 (2007)). A stainless steel 1 g weight (Mettler-Toledo) equilibrated to the temperature of dry ice was placed directly on the exposed TA for 10 seconds. Following the thermal injury, incision was closed using VetBond (3M). All injury procedures were performed on the left leg, and the right leg was used as control.

C. Histology

Animals were perfused with 15 mL of ice-cold PBS followed immediately by 20 mL of 10% saline buffered formalin. TA muscles were excised and immersed in 4% paraformaldehyde for at least 48 hours at 4° C. Tissues were dehydrated in series of solutions with increasing percentage of ethanol. Dehydrated tissues were cleared in xylene and allowed for paraffin to permeate over night at 60° C. Tissues were then embedded in plastic molds.

Paraffin embedded tissue blocks were sectioned at 7 μm thick on Leica Jung 2500 Microtome. Sections were stained with hematoxylin and counter stained with 1% eosin. Slides were dried and mounted with Entellan mounting media (EMS). Three random non-overlapping fields were photographed for analysis. Regenerating fiber number was measured by counting the number of discernible muscle fibers with centralized myonuclei (Ge et al., *Am J Physiol Cell Physiol* 297(6):C1434-1444 (2009)). Regenerating fiber cross sectional area (CSA) was measured using Image J software.

D. Evans Blue Dye Staining

Injured animals were injected with Evans Blue dye according published protocol (Hamer et al., *J Anat* 200(Pt 1):69-79 (2002)). Sterile 1% w/v Evans Blue dye in PBS was intraperitoneally injected at 1% volume relative to the body mass of an animal. Seven hours after the injection, injured TA muscles were harvested and snap-frozen by isopentane quenching in liquid nitrogen. Frozen sections were cut in 10 μm thickness, fixed in ice-cold acetone, dipped in xylene and mounted with DPX. Proportion of the stained area over the total area was measured using ImageJ software.

E. BrdU Labeling 50 mg/kg body weight of BrdU (Sigma) was injected intraperitoneally as solution of 10 mg/mL BrdU in saline. TA muscles were harvested at 7 days after injury and processed for paraffin sections as described above. BrdU incorporation was visualized using the BrdU Labeling and Detection Kit I (Roche) and BrdU+ nuclei were counted and represented as a proportion of total nuclei in a field.

F. RT-QPCR

Whole or partial tissues were homogenized by Polytron probe homogenizer in Trizol reagent (Invitrogen). Total RNA was extracted from the homogenates according to the manufacturer's protocol. 1 μg of DNase-treated total RNA was reverse transcribed using Superscript II Reverse Transcriptase (Invitrogen) according to the manufacturer's instructions. cDNAs were diluted 1/40 with ddH$_2$O and used as templates in RT-QPCR reactions with SYBRGreenER qPCR SuperMix detection system (Invitrogen). Samples were prepared in technical triplicates and relative mRNA levels were calculated by using the standard curve methodology and normalized against GAPDH mRNA levels in the same samples.

G. Myofiber Isolation

Either whole or partial gastrocnemius muscle was digested in 2% collagenase I (Sigma) in DMEM with 10% FBS for 60 minutes at 37° C. Muscle tissue was further mechanically digested by triturating with fire polished wide bore Pasteur pipet. Liberated fibers were washed in two changes of PBS with 10% FBS and finally mounted on glass slides with Vectashield mounting media (Vector Labs).

H. Isolation of Satellite Cells

Satellite cells were harvested from TA of 8 weeks old animals according to published protocols with some modifications (Day et al. (2007) Nestin-GFP reporter expression defines the quiescent state of skeletal muscle satellite cells. *Dev Biol* 304(1):246-259). Muscles were removed and washed briefly in DMEM on ice. They were then minced to fine slurry with razor blade on 60 mm culture dish over ice. Minced muscles were transferred to one well of a 6-well plate containing 5 ml of 450 KPU/ml pronase in DMEM. The tissues were digested at 37° C./5% CO$_2$ for 60 minutes. After digestion, tissues were vigorously triturated 20 times through 10 ml serological pipet. Digested tissues were filtered through 40 micron cell strainer and washed with equal volume of DMEM with 20% horse serum. Cells were spun down at 1000 g for 10 minutes and resuspended in sorting buffer (DMEM with 10% FBS). Cells were separated from larger debris by 20%/60% Percoll gradient (Yablonka-Reuveni Z et al. (1987) Isolation and clonal analysis of satellite cells from chicken pectoralis muscle. *Dev Bio* 119: 252-259). GFP positive cells were sorted on BD FACSAria II sorter.

Example 2

Muscle Specific Activation of PPARδ Confers Regenerative Advantage

While it has been shown that the majority of the metabolic genes are down regulated in this model, PPARδ expression was induced over 2 fold at 2 days after the injury (Warren et al. (2007) Mechanisms of skeletal muscle injury and repair revealed by gene expression studies in mouse models. *J Physiol.* 582.2: 825-841, FIG. 1A). This injury dependent up-regulation of PPARδ strongly suggested a possible role for PPARδ during the early part of the regenerative process.

Freeze burn injury was used to elicit the regenerative program, which has been shown to model the standard course of regenerative response, including satellite cell activation (Karpati and Molnar. "Muscle fibre regeneration in human skeletal muscle diseases." In: Schiaffino S, Partridge T (eds). Skeletal muscle repair and regeneration. Springer, Dordrecht, 2008). Additionally, since the injury is directly applied to the surface of the muscle, it is highly localized and reproducible.

Figure 1D:
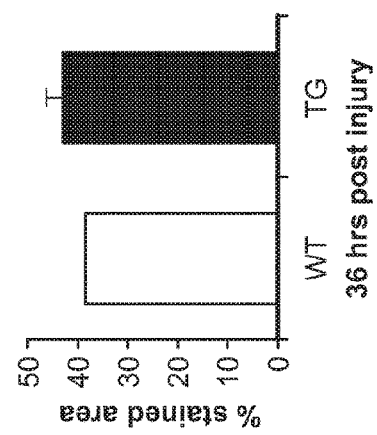
Figure 1E:
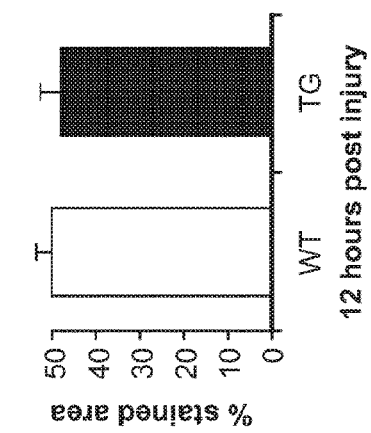
Figure 1F:
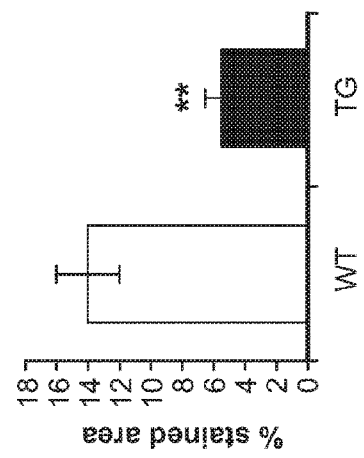

Using Evans Blue dye uptake as a marker of myofiber damage, fiber integrity was histologically assessed. The freeze burn injury does not incapacitate the animals and the damaged fibers restore original cross sectional area by 21 days after the injury (FIG. 1B). By comparing the proportion of stained fibers within the cross sectional area (CSA) of the injured muscle 5 days after the injury, the degree of existing damage was quantified. At 5 days after the injury, VP16-PPARδ (TG) animals show significantly less dye uptake, thus increased fiber intactness, over the wildtype (WT) animals (FIG. 1C). While 14% of the total CSA shows dye uptake, only 5% of the total CSA of TG muscle show dye uptake (n=8 WT; n=5 TG; p=0.001) (FIG. 1D). At 12 and 36 hours after the injury, however, both WT and TG animals showed similar proportions of stained area (50.6% and 47.4% (p=0.67), and 38.5% and 43.3% (p=0.23), respectively) (FIGS. 1E and 1F). Similar level of dye uptake shortly after the injury shows that both WT and TG animals initially sustain similar degree of damage from the injury and suggests that PPARδ activation does not confer protection from damage. Instead, the reduction in Evans Blue dye uptake observed 5 days after the injury suggests that the muscle specific PPARδ activation promotes restoration of fiber integrity after the injury.

The morphological hallmarks of regenerating fibers was determined for a detailed analysis of the process. H&E stained transverse sections through the injured area were examined at 3, 5 and 7 days post injury. At 3 days after the injury, both WT and TG animals showed similar degrees of degeneration defined as necrosing fibers surrounded by infiltrating monocytes (FIG. 1G). No regenerating fibers, characterized by small, round shape and centralized nuclei, were discernible at this time point in WT animals, but a notable few were seen in TG animals (arrows, FIG. 1G). By day 5 after the injury, obvious differences begin to emerge. In WT animals, small regenerating fibers were visible but necrosing fibers and monocytes were still prevalent at the site of the injury (arrowheads, FIG. 1G). While in the TG animals, the injury site harbors orderly arrangement of small regenerating fibers. Quantification of regenerating fiber number and CSA reveals that by 5 days post injury, TG animals show significant regenerative advantage over their WT counterparts. Both CSA of the regenerating fibers and the number of regenerating fibers were significantly greater for TG animals at 43.5% (n=5 or 6; p<0.03) and 33.0% (n=11 or 12; p<0.001), respectively (FIGS. 1B and 1C). By day 7 post injury, the damage site appears architecturally similar between WT and TG animals, where both show a field of immature regenerating fibers without the infiltrating immune cells. However, quantification of the regenerating fibers revealed a regenerative advantage of the TG animals in the number of nascent regenerating fibers (FIG. 1H). At 21 days after the injury, both WT and TG animals have restored their fiber size and number to that of the uninjured level (FIG. 1J). These data demonstrate that the muscle specific activation of PPARδ sufficiently bestows regenerative advantage, most prominently observed in the early stages of the regenerative process.

Example 3

PPARδ Activation Leads to Temporal Shift, Thus Increased Efficiency of the Regenerative Process Skeletal muscle regeneration is an intricately orchestrated process involving a variety of cell types. For example, immune cells, both neutrophils and macrophages, are necessary for the proper progression of regenerative process (Zacks et al., *Muscle Nerve* 5:152-161 (1982); Grounds et al., *Cell Tissue Res* 250:563-569 (1987); Teixeira et al., *Muscle Nerve* 28(4):449-459 (2003); Summan et al., *Am J Physiol Regul Integr Comp Physiol* 290:R1488-R1495 (2006); Contreras-Shannon et al., *Am J Physiol Cell Physiol* 292:C953-967 (2007); Segawa et al., *Exp Cell Res* 314(17): 3232-3244 (2008)). Additionally, various cytokines are necessary to promote chemotaxis of monocytes and also to directly regulate the activities of myogenic cells (Warren et al., *Am J Physiol Cell Physiol* 286(5):C1031-1036 (2004); Yahiaoui et al., *J Physiol* 586:3991-4004 (2008); Chazaud et al., *JCB* 163(5):1133-1143 (2003)). Therefore, the temporal expression profiles of genes associated with various aspects of the regenerative process was determined.

Figure 2A:
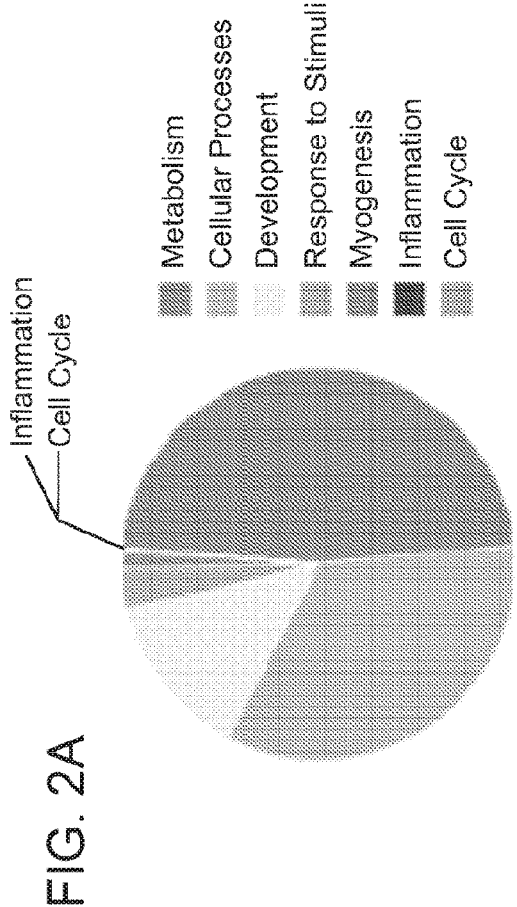
FIGS. 2A-2E illustrate that PPARδ activation promotes a temporal shift in gene expression profile of the regenerative process. *P<0.05. All error bars are SEM.
Figure 2B:
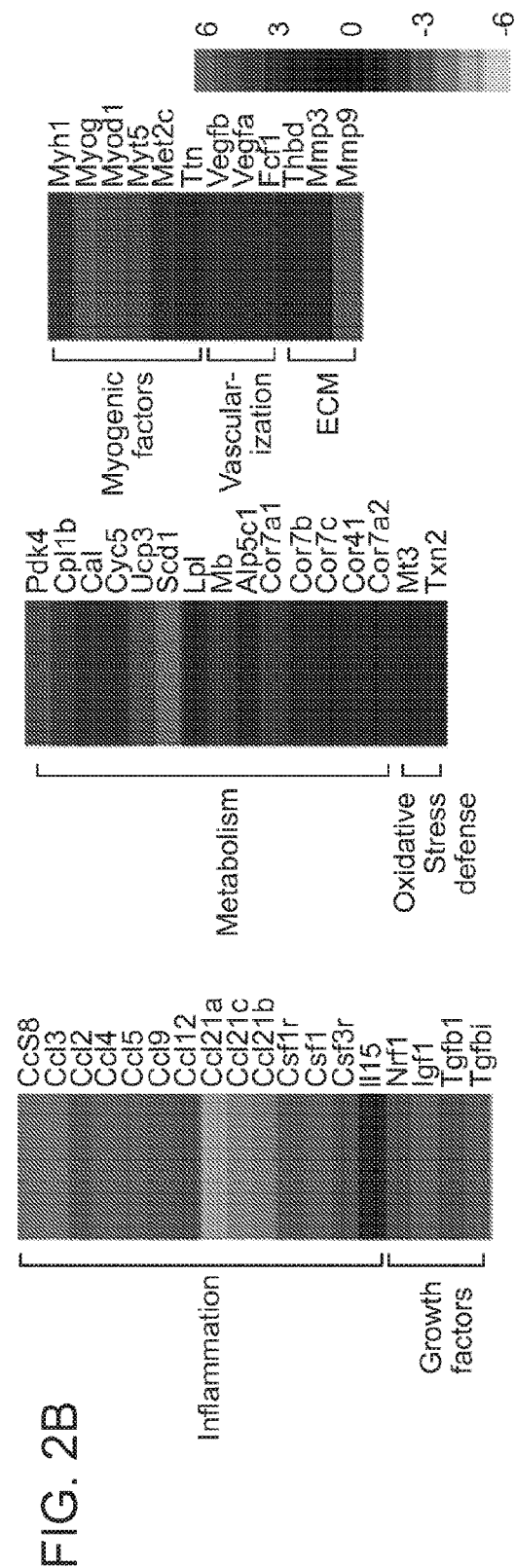

Global, injury specific gene expression changes, were identified in VP16-PPARδ animals by microarray. Comparing the gene expression profiles of injured TG to WT 3 days post-injury, 3257 genes that changed expression pattern, of those, 1375 of them were down regulated and 1882 were up regulated. Interestingly, genes involved in myogenesis and remodeling were robustly up-regulated by PPARδ activation while those involved in inflammatory response were down regulated in injured TG muscles (FIG. 2A). Additionally, genes involved in developmental processes, angiogenesis and anti-apoptotic processes emerged from the analysis (FIG. 2A). Relative expressions of regeneration markers reveal down-regulation of early makers (inflammatory genes) and up-regulation of regenerative/remodeling genes (myogenic, vascularization, ECM genes) in TG animals 3 days post injury (FIG. 2B). Collectively, PPARδ activation appears to control a network of genes involved directly in myogenesis and also in remodeling and repair processes after the injury.

Figure 2C:
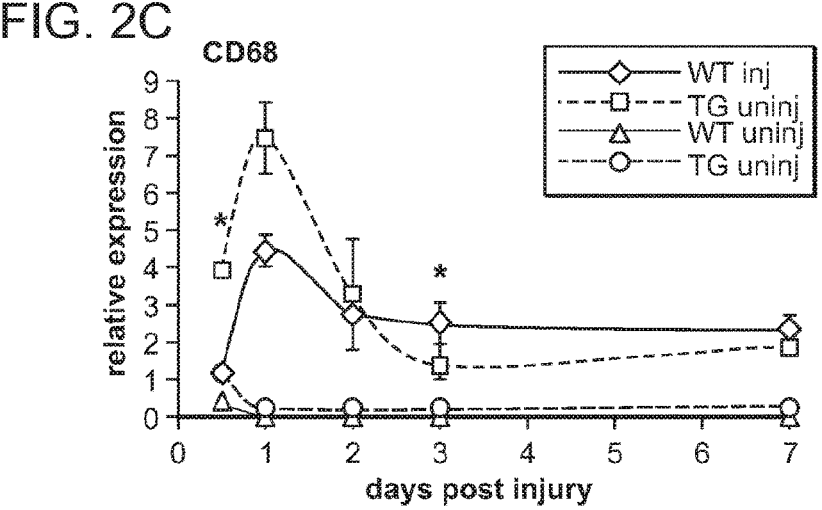
Figure 2D:
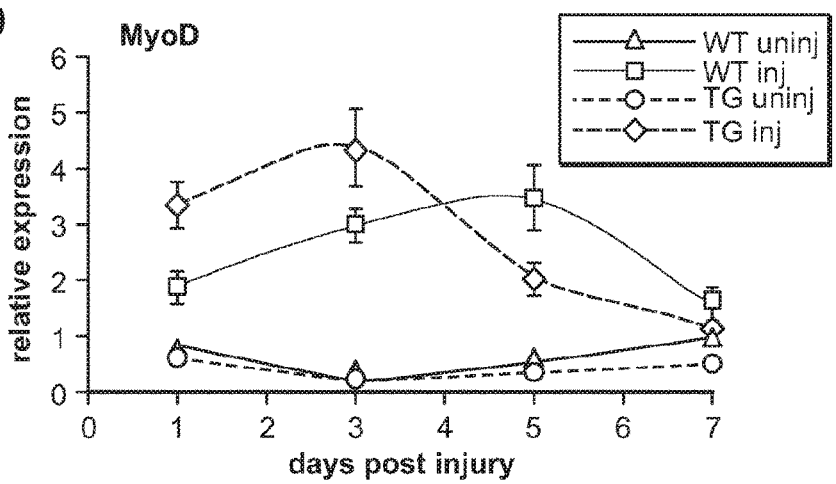
Figure 2E:
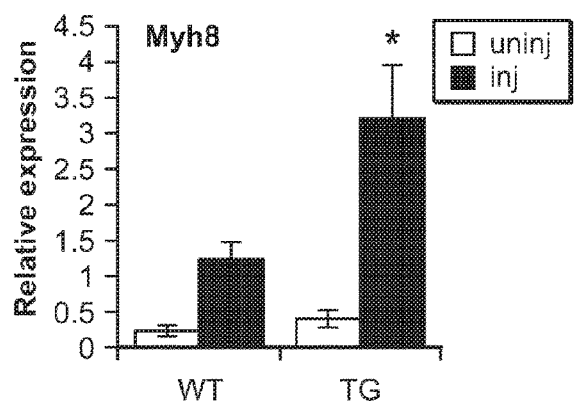

Underlying phasic progression of the regenerative program is a temporally coordinated gene expression of a variety of contributing processes. In order to validate and temporally expand the microarray data, expression of CD68 (inflammation) and MyoD (myogenesis) were measured by Q-PCR at several time points over 7 days after injury (FIGS. 2C and 2D). A temporal shift in the expression patterns of regenerative markers for TG animals compared to their WT littermates was observed. TG animals showed rapid induction of CD68 whose expressions peaked sooner and were subsequently down regulated earlier than in the WT animals. Interestingly, inflammatory markers studied here peaked at similar levels between the two genotypes, which indicates that TG animals do not completely suppress their inflammatory responses. Instead, it appears that the TG animals respond and resolve their inflammatory responses more efficiently, which is consistent with the accelerated restoration of muscle morphology observed. TG animals also show higher expression of perinatal myosin heavy chain gene, Myh8, at 7 days post injury, indicating more efficient reassembly of the contractile properties (FIG. 2E). PPARδ activation leads to a temporal shift in the expression patterns of regenerative markers, which together with the histology data, shows a role of PPARδ in increasing regenerative efficiency.

Example 4

PPARδ Directs Neo-Vascularization Via Regulation of FGF1

This example describes adaptive responses bestowed by PPARδ activation in the muscle which may contribute to the observed beneficial effects on regeneration.

Figure 3A:
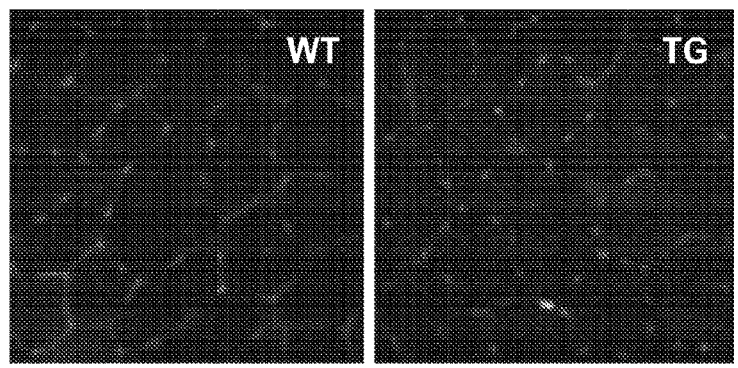
FIGS. 3A-3G illustrate that PPARδ regulates FGF1a to promote micro-vascularization. *P<0.05; **P<0.01. All error bars are SEM.
Figure 3B:
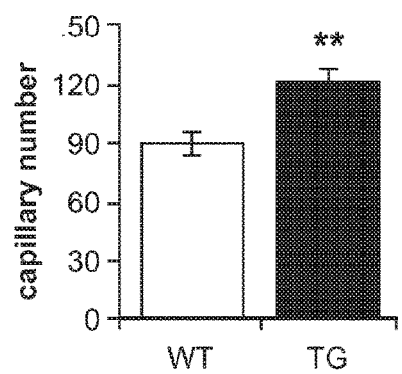
Figure 3C:
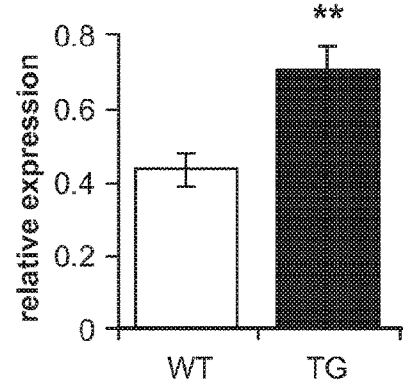
Figure 3D:
Figure 3E:
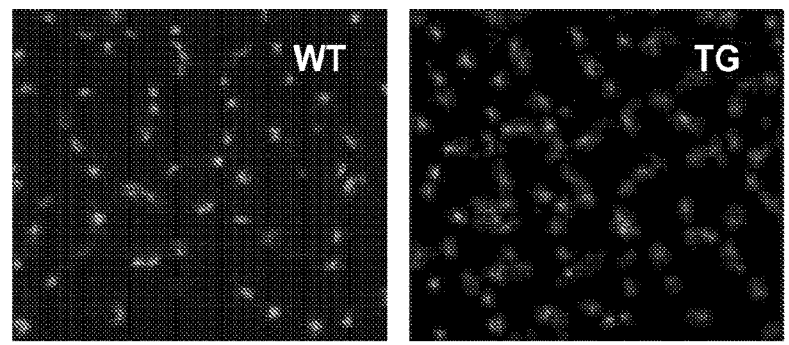
Figure 3F:
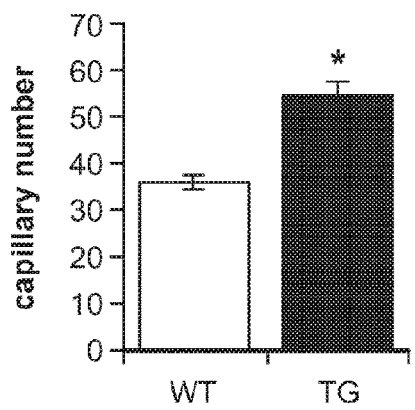
Figure 3G:
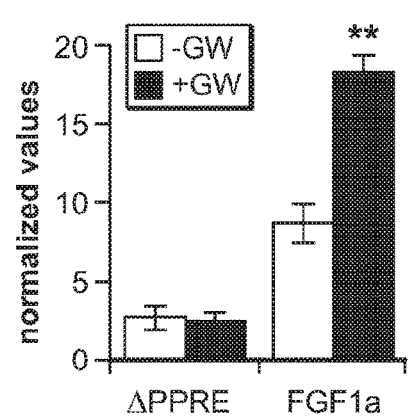

Increased vasculature is one of the hallmarks of oxidative myofibers, which facilitates introduction of immune cells and also supports increased number of satellite cells. TG animals show increased expression of FGF1 in TA muscle (FIG. 3D). Upon injury, TG animals maintain high expression of FGF1 expression (FIG. 3D). Immunostaining transverse sections of uninjured TA from WT and TG animals revealed 36% increase in the number of CD31+ capillaries per field by PPARδ activation (FIGS. 3A-C). Furthermore, after the injury, TG animals show increased expression of CD31, which is indicative of increased vascularity (FIG. 3E-F). The induction of FGF1a upon activation of PPAR delta with the GW1516 ligand was confirmed using a luciferase reporter assay (FIG. 3G). FGF1 has been shown to be expressed in regenerating fibers in chronic disease models and has been implicated in myogenesis and regeneration (Oliver, Growth Factors. 1992; 7(2):97-106, 1992; Saito, 2000, Muscle Nerve. 23(4):490-7) and to increase microvasculature in adipocytes and PPARδ directly regulates expression of FGF1a isoform (Jonker, et al., Nature. 485(7398):391-4, 2012). Therefore, increased vascularity may contribute to the accelerated regenerative process observed in VP16-PPARδ animals.

Example 5

PPARδ Activation Positively Regulates Quiescent Satellite Cell Number

One of the first events following the injury is the proliferation of muscle resident progenitors, the satellite cells. This example describes results showing that the regenerative advantage observed in TG animals could be due to altered satellite cell homeostasis.

Figure 4A:
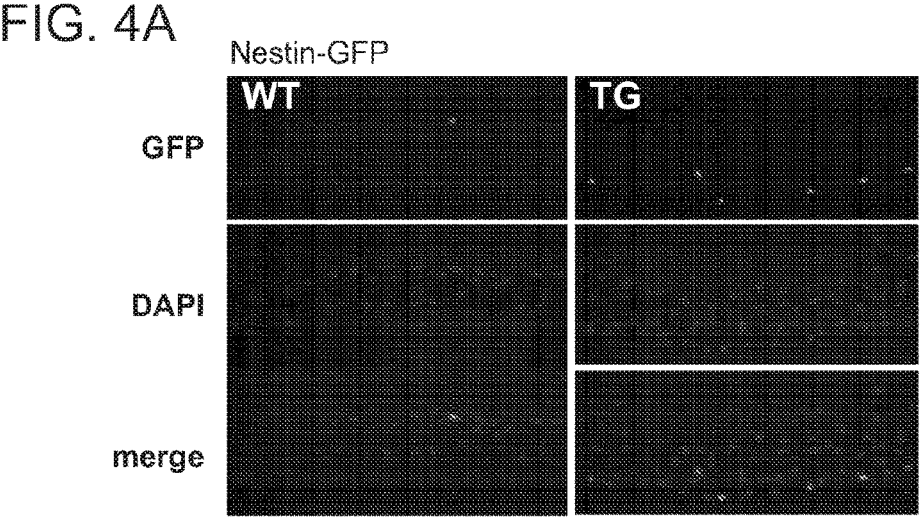
Figure 4B:
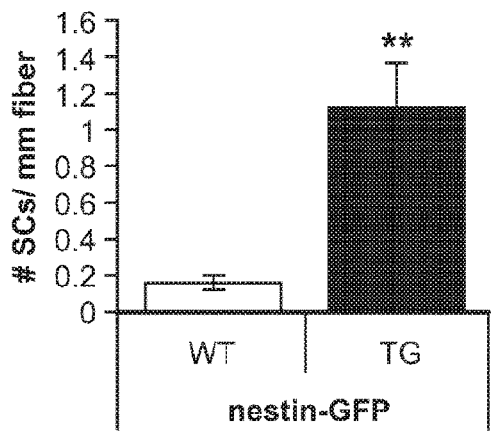

Nestin expression was used as a marker of satellite cells, and nestin-GFP; VP16-PPARδ double transgenic animals were used to genetically label quiescent satellite cells (SCs) in vivo (Mignone et al., J Comp Neurol 469(3):311-324 (2004); Day et al., Dev Biol 304(1):246-259 (2007)). Gastrocnemius muscles were enzymatically digested to liberate individual fibers, then mounted for quantification (FIG. 4A). While double transgenic animals averaged 1.01 SCs per mm of fiber length, GFP+ animals only had 0.15 SCs per mm, a 6.48 fold higher SC content on VP16-PPARδ muscle fiber (FIG. 4B).

Figure 4C:
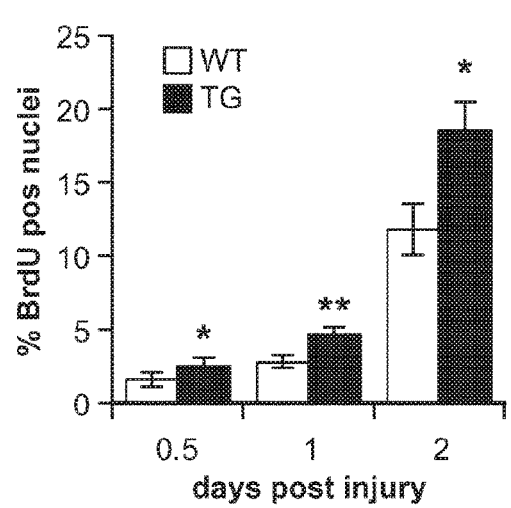
Figure 7D:
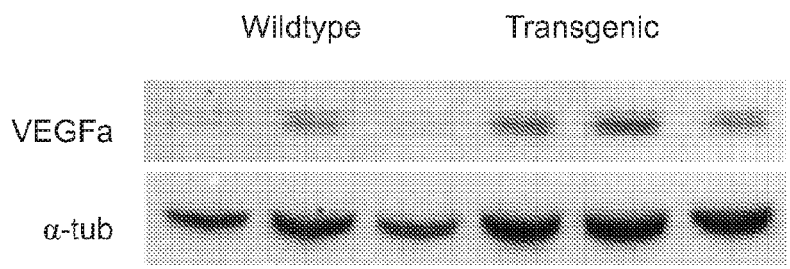
FIG. 7D shows induction of VEGFα in TA muscle, as measured by Western Blot, in TG animals.
Figure 7E:
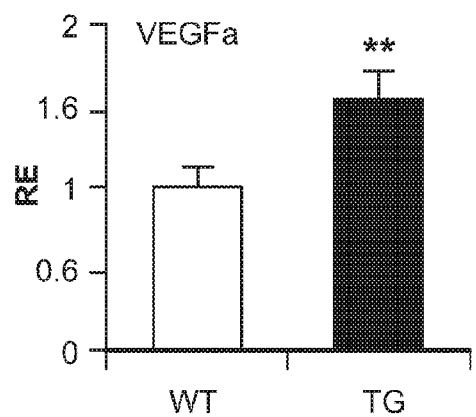
FIG. 7E shows quantification of TNFα Western Blot.

Satellite cell activity was measured as myoblast proliferation elicited by the freeze burn injury in vivo. After the freeze burn injury, BrdU was intraperitoneally injected at 12 hrs, 24 hrs and 2 days after the injury and the muscles were harvested 7 days after the injury to calculate the ratio of BrdU+ to total nuclei. TG animals showed 40-60% increase in the number of BrdU+ proliferating cells at all three injection times (FIG. 4C). Therefore, PPARδ induced increase in the number of quiescent satellite cells yields higher number of fusion competent myoblasts, leading to the enhancement of regenerative capacity of the muscle.

Example 6

Acute Pharmacological Activation of PPARδ Confers Regenerative Advantage

Pharmacological activation of PPARδ has been shown to induce PPARδ target genes in fast-twitch hind limb muscles (Narkar et al., Cell 134(3):405-415 (2008)). To demonstrate that an acute pharmacological activation of PPARδ can modulate regenerative process after injury, C57BL6J mice were treated with GW501516 (Sundai Chemicals, China) orally at 5 mg/kg for 4 days prior to and 5 days after the thermal injury to the TA.

Up-regulation of known PPARδ target genes (PDK4, CPT1b, and catalase) was confirmed by QPCR, attesting to the successful delivery and activity of the PPARδ ligand in the muscle (FIG. 5A). While vehicle treated animals showed dye uptake in 7.6% of the cross sectional area (CSA), merely 4.9% of the muscle CSA was stained in the ligand treated animals (FIGS. 5B and 5C). Therefore, the drug treated animals showed 34.7% reduction in the proportion of stained area 5 days after the injury, demonstrating that pharmacological activation of PPARδ enables accelerated restoration of myofiber integrity after the injury.

Moreover, BrdU injection at 48 hours after the injury revealed that PPARδ activation promotes myoblast proliferation after the injury (FIG. 5D). However, an increase in the number of quiescent satellite cells was not observed after 9 days or 4 weeks of ligand treatment. Since satellite cells do not undergo rapid turnover, length of ligand treatment may have been too short. Nonetheless, GW501516 treatment promoted myoblast proliferation in vivo after the injury, which may contribute to the accelerated regeneration after the injury.

The expression of inflammatory marker genes at 3 days after the injury was measured by QPCR. While the initial inflammatory responses are similarly generated with or without the PPARδ ligand treatment at 12 hours after the injury, by 3 days after the injury, the expressions of inflammatory marker genes were significantly reduced by the PPARδ agonist treatment (FIG. 5E). This result is consistent with the known role of PPARδ as an anti-inflammatory, and also corroborates the data discussed earlier with the genetic over-expression of activated PPARδ during muscle regeneration.

In summary, PPARδ activation expedites skeletal muscle regeneration following an acute thermal injury. VP16-PPARδ transgenic animals showed increased satellite cell proliferation at the early phase of the regenerative process, which subsequently translated into increased CSA and the number of nascent regenerating fibers. Most interestingly, muscle specific over expression of PPARδ seems to increase the resident satellite cell pool. Increased satellite cell population on a muscle fiber seems to contribute to the accelerated resolution of the injury. These findings unveil a novel role for PPARδ in the maintenance of skeletal muscle; as a potential therapeutic target for accelerated restoration of muscle mass after an acute injury and other atrophic conditions.

Notably, PPARδ activation seems to promote rapid emergence of nascent fibers after the injury. There being no evidence of hyperplasia at 21 days after the injury when the regenerative process is essentially complete, it is concluded that the additional nascent fibers efficiently fuse with each other to restore mature fibers (Karpati G, Molnar M J in *Skeletal muscle repair and regeneration*, eds Schiaffino S, Partridge T (Springer, Dordrecht), (2008)). While IGF-1 and myostatin seem to rely on fiber hypertrophy to augment regenerative progress, PPARδ seems to employ a unique way to promote regeneration (Menetrey et al., *J Bone Joiny Surg Br* 82(1):131-7 (2000); Wagner et al., *Ann Neurol* 52(6): 832-6 (2002); Bogdanovich et al., *Nature* 420(6914): 418-21 (2002)). Underlying this difference may be the increased number of quiescent satellite cells. Higher number of progenitor cells leads to the increase in post injury proliferating cells and consequent increase in the number of nascent fibers. While various growth factors and chemokines, including IGF-1 and myostatin, have been shown to enhance proliferation of satellite cells and promote regeneration, it is unclear whether any of them positively regulate the number of quiescent satellite cells (Husmann I et al., *Cytokine Growth Factor Rev* 7(3):249-258 (1996); McCroskery S et al., *J Cell Biol* 162(6):1135-1147 (2003); Musaro A et al., *Nat Genet* 27:195-200 (2001); Amthor H et al., *PNAS* 106(18):7479-84 (2009)). The findings shown herein indicate a novel role of PPARδ as a positive regulator of satellite cell pool. Interestingly, since rapid cell proliferation was not observed under normal conditions, PPARδ mediated satellite cell expansion is transient and tightly regulated, most likely elicited by external stimuli, such as signals for postnatal growth and injury. In an adult muscle, satellite cell number is finite, diminishing detrimentally in disease state and aging. It is of great therapeutic benefit if PPARδ activation can bestow infinite abundance of satellite cell population throughout the life of an organism.

While enhancement in regenerative capacity was observed in both genetic and pharmacological models, the inherent differences in the experimental parameters is acknowledged. Orally administered GW501516 was delivered systemically, presumably activating PPARδ in a variety of organs and cell types in the animal. However, in VP16-PPARδ animals, activation of the PPARδ receptors is limited to the mature muscle fibers. Additionally, genetic background of the animals may affect the efficiency of regeneration after an injury (Grounds and McGeachie, *Cell Tissue Res* 255(2):385-391 (1989); Roberts et al., *J Anat* 191:585-594 (1997)). Extramuscular effects of PPARδ agonist administration may require further investigation when considering clinical use of GW501516 to augment muscle injury treatment. Recently, pharmacological activation of PPARδ has been shown to improve sarcolemmal integrity in mdx mice (Miura et al., *Hum mol Genet* 18(23):4640-4649 (2009)).

The results herein expand previous understandings of the role of PPARδ in muscle physiology. It is shown herein that PPARδ not only controls running endurance and metabolic parameters in the muscle, but also its regenerative program. PPARδ activation affects multiple facets of the regenerative program, exerting comprehensive but transient effects to expedite the progress. In view of these findings, PPARδ may be pharmacologically targeted to enhance the regenerative capacity of the muscle after injury and possibly other degenerative conditions where satellite cell function is compromised. For example, PPARδ activation can be used to treat other degenerative conditions such as aging induced satellite cell dysfunction and ensuing sarcopenia.

Example 7a

PPARδ Activity Screen

Cell Culture and Transfection:

CV-1 cells were grown in DMEM+10% charcoal stripped FCS. Cells were seeded into 384-well plates the day before transfection to give a confluency of 50-80% at transfection. A total of 0.8 g DNA containing 0.64 micrograms pCMX-PPARDelta LBD, 0.1 micrograms pCMX.beta.Gal, 0.08 micrograms pGLMH2004 reporter and 0.02 micrograms pCMX empty vector was transfected per well using FuGene transfection reagent according to the manufacturer's instructions (Roche). Cells were allowed to express protein for 48 h followed by addition of compound.

Plasmids:

Human PPARδ was used to PCR amplify the PPARδ LBD. The amplified cDNA ligand binding domain (LBD) of PPARδ isoform was (PPARδ amino acid 128 to C-terminus) and fused to the DNA binding domain (DBD) of the yeast transcription factor GAL4 by subcloning fragments in frame into the vector pCMX GAL (Sadowski et al. (1992), Gene 118, 137) generating the plasmids pCMX-PPARDelta LBD. Ensuing fusions were verified by sequencing. The pCMXMH2004 luciferase reporter contains multiple copies of the GAL4 DNA response element under a minimal eukaryotic promoter (Hollenberg and Evans, 1988). pCMXβGal was generated.

Compounds: All compounds were dissolved in DMSO and diluted 1:1000 upon addition to the cells. Compounds were tested in quadruple in concentrations ranging from 0.001 to 100 µM. Cells were treated with compound for 24 h followed by luciferase assay. Each compound was tested in at least two separate experiments.

Luciferase Assay: Medium including test compound was aspirated and washed with PBS. 50 µl PBS including 1 mM Mg++ and Ca++ were then added to each well. The luciferase assay was performed using the LucLite kit according to the manufacturer's instructions (Packard Instruments). Light emission was quantified by counting on a Perkin Elmer Envision reader. To measure 3-galactosidase activity 25 µl supernatant from each transfection lysate was transferred to a new 384 microplate. Beta-galactosidase assays were performed in the microwell plates using a kit from Promega and read in a Perkin Elmer Envision reader. The beta-galactosidase data were used to normalize (transfection efficiency, cell growth etc.) the luciferase data.

Statistical Methods: The activity of a compound is calculated as fold induction compared to an untreated sample.

For each compound the efficacy (maximal activity) is given as a relative activity compared to GW501516, a PPARδ agonist. The $EC_{50}$ is the concentration giving 50% of maximal observed activity. $EC_{50}$ values were calculated via non-linear regression using GraphPad PRISM (GraphPad Software, San Diego, Calif.).

The following examples provide physical and in vitro data for various different exemplary compounds.

Nuclear Hormone Receptor (NHR) Assays

Cell Handling: PathHunter NHR cell lines were expanded from freezer stocks according to standard procedures. Cells were seeded in a total volume of 20 μL into white walled, 384-well microplates and incubated at 37° C. for the appropriate time prior to testing. Assay media contained charcoal-dextran filtered serum to reduce the level of hormones present.

Agonist Format: For agonist determination, cells were incubated with sample to induce response. Intermediate dilution of sample stocks was performed to generate 5× sample in assay buffer. 5 μL of 5× sample was added to cells and incubated at 37° C. or room temperature for 3-16 hours. Final assay vehicle concentration was 1%.

Antagonist Format: For antagonist determination, cells were pre-incubated with antagonist followed by agonist challenge at the $EC_{80}$ concentration. Intermediate dilution of sample stocks was performed to generate 5× sample in assay buffer. 5 μL of 5× sample was added to cells and incubated at 37° C. or room temperature for 60 minutes. Vehicle concentration was 1%. 5 μL of 6×$EC_{80}$ agonist in assay buffer was added to the cells and incubated at 37° C. or room temperature for 3-16 hours.

Signal Detection: Assay signal was generated through a single addition of 12.5 or 15 μL (50% v/v) of PathHunter Detection reagent cocktail, followed by a one hour incubation at room temperature. Microplates were read following signal generation with a PerkinElmer Envision™ instrument for chemiluminescent signal detection.

Data Analysis: Compound activity was analyzed using CBIS data analysis suite (ChemInnovation, CA). For agonist mode assays, percentage activity was calculated using the following formula:

% Activity=100%×(mean RLU of test sample−mean RLU of vehicle control)/(mean MAX control ligand−mean RLU of vehicle control).

For antagonist mode assays, percentage inhibition was calculated using the following formula:

% Inhibition=100%×(1−(mean RLU of test sample−mean RLU of vehicle control)/(mean RLU of $EC_{80}$ control−mean RLU of vehicle control)).

Note that for select assays, the ligand response produces a decrease in receptor activity (inverse agonist with a constitutively active target). For those assays inverse agonist activity was calculated using the following formula:

% Inverse Agonist Activity=100%×((mean RLU of vehicle control−mean RLU of test sample)/ (mean RLU of vehicle control−mean RLU of MAX control)).

TABLE 1

NHR Interaction Assay and PPARdelta Activity Screen

| Compound | Mol. Wt | NHR Protein Interaction Biosenor assay, PPARdelta EC50 (nM) | PPAR delta transactivation EC50 (nM) |
|---|---|---|---|
| Compound 8a | 433.50 | 5.06 | 56.00 |
| Compound 8b | 443.54 | 33.60 | 226.00 |
| Compound 8c | 451.49 | 1.93 | 15.00 |
| Compound 8d | 467.90 | 1.59 | 7.40 |
| Compound 8e | 447.53 | 11.86 | |
| Compound 8f | 421.49 | 45.06 | |
| Compound 8g | 451.49 | 5.51 | 40.00 |
| Compound 8h | 435.20 | 40.20 | 998.00 |
| Compound 8i | 433.49 | 693.50 | |
| Compound 8j | 435.52 | 64.50 | 566.00 |
| Compound 8k | 433.50 | 1849.20 | |
| Compound 8l | 417.51 | 1265.10 | |
| Compound 8m | 420.51 | 13.49 | 1316.00 |
| Compound 8n | 447.40 | 22.6 | 19.80 |
| Compound 8o | 435.51 | 228.90 | 1639.00 |
| Compound 8p | 469.54 | 1757.20 | |
| Compound 8q | 455.51 | 116.02 | |
| Compound 8r | 471.51 | 627.57 | |
| Compound 8s | 449.55 | 510.92 | |
| Compound 8t | 433.50 | 52.10 | 308.00 |
| Compound 8u | 433.50 | 265.9 | 320.00 |
| Compound 8v | 433.50 | 209.9 | 2510.00 |
| Compound 8w | 433.50 | 706.8 | 643.80 |
| Compound 8x | 433.50 | 264.9 | 82.50 |
| Compound 8y | 439.53 | 232.90 | |
| Compound 8z | 437.54 | 5544.50 | |
| Compound 8aa | 501.50 | | 683.00 |
| Compound 8bb | 473.57 | | 58% inhibition @ 10 uM |
| Compound 8cc | 419.48 | 80.43 | |

Example 7b

Pharmacokinetic Screening

In this example, the PK profile of several PPARδ agonists disclosed herein in male CD-1 mice or Wistar rats was determined. Similar methods can be used to analyze other compounds provided herein.

All compounds were separately administered to CD-1 mice at 3 mg/kg iv or 10 mg/kg po. GW501516 was administered to Wistar rats at 3 mg/kg (i.v.) or 10 mg/kg (p.o.).

TABLE 2

Pharmacokinetic Data

| Compound | NHR Protein Interaction Biosenor assay, PPAR-delta EC50 (nM) | Mice_PK_IV_Cl [ml/min/kg] | Mice_PK_IV_AUC (0-inf) [ng * hr/ml] |
|---|---|---|---|
| Compound 8a | 5.06 | 15.16 | 3299.40 |
| Compound 8c | 1.93 | 34.30 | 1459.00 |
| Compound 8cc | | 66.87 | 748.00 |
| Compound 8d | 1.59 | 34.65 | 1443.00 |
| Compound 8e | 11.86 | 23.10 | 2166.00 |
| Compound 8f | 45.06 | 40.02 | |
| Compound 8g | 5.51 | 23.00 | 2195.00 |
| Compound 8h | 40.20 | 4.20 | 11843.00 |
| Compound 8i | 693.50 | 10.65 | 4691.00 |

TABLE 2-continued

Pharmacokinetic Data

| Compound | NHR Protein Interaction Biosenor assay, PPAR-delta EC50 (nM) | Mice_PK_IV_Cl [ml/min/kg] | Mice_PK_IV_AUC (0-inf) [ng * hr/ml] |
|---|---|---|---|
| Compound 8k | 1849.20 | 3.92 | 12804.00 |
| Compound 8l | 1265.10 | 9.68 | 5161.00 |
| Compound 8m | 13.49 | 115.00 | 434.70 |
| Compound 8n | 22.6 | 5.10 | |
| Compound 8o | 228.90 | 2.78 | 11397.00 |
| Compound 8p | 1757.20 | 173.05 | 288.90 |
| Compound 8q | 116.02 | 80.32 | 622.50 |
| Compound 8s | 510.92 | 1.03 | 48454.90 |
| Compound 8t | 52.10 | 3.08 | |
| Compound 8u | 265.9 | 1.70 | 30142.00 |
| Compound 8w | 706.8 | 1.70 | |
| Compound 8x | 264.9 | 1.90 | |

Provided below is a comparison of activity and pharmacokinetic data of some compounds of the invention against several comparator compounds

TABLE 3

Activity/Pharmacokinetic Comparison

| Comparator Compound | Compound | NHR Protein Interaction Biosenor assay, PPARdelta EC50 (nM) | Mice_PK_IV_Cl [ml/min/kg] |
|---|---|---|---|
| Comparator Cmpd. 1<br>PPAR-delta EC50 = 12.6 nM<br>Mice_PK_IV_Cl = 44.06 mL/min/kg | Compound 8a | 5.06 | 15.16 |
| | Compound 8t | 52.10 | 3.08 |
| Comparator Cmpd. 2<br>PPAR-delta EC50 = 4.81 nM<br>Mice_PK_IV_Cl = 194.4 mL/min/kg | Compound 8h | 40.20 | 4.20 |
| | Compound 8n | 22.6 | 5.10 |

TABLE 3-continued

Activity/Pharmacokinetic Comparison

| Comparator Compound | Compound | NHR Protein Interaction Biosenor assay, PPARdelta EC50 (nM) | Mice_PK_IV_Cl [ml/min/kg] |
|---|---|---|---|
| Comparator Cmpd. 7<br>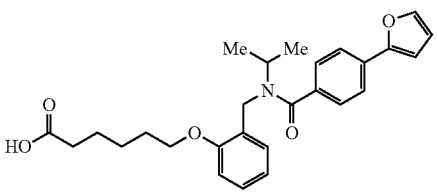 [SMILES: CC(C)N(Cc1ccccc1OCCCCCC(=O)O)C(=O)c1ccc(-c2ccco2)cc1]<br>PPAR-delta EC50 = 511.80 nM | 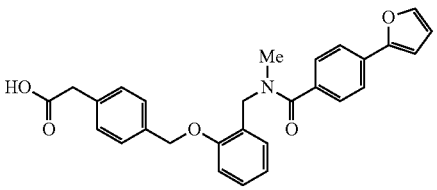 [SMILES: CN(Cc1ccccc1OCc1ccc(CC(=O)O)cc1)C(=O)c1ccc(-c2ccco2)cc1]<br>Compound 8m | 23.50 | 36.57 |
| Comparator Cmpd. 3<br>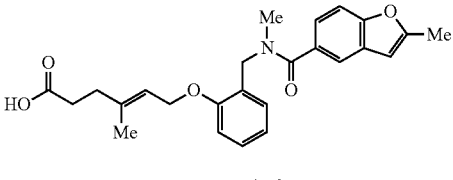<br>PPAR-delta EC50 = 60.16 nM<br>Mice_PK_IV_Cl = 27.95 mL/min/kg<br>[AUC (0-inf) = 1788.0 ng * hr/ml] | 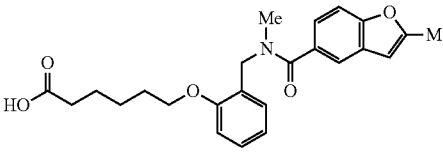<br>Compound 8f | 45.06 | 40.02 |

Figure 8:
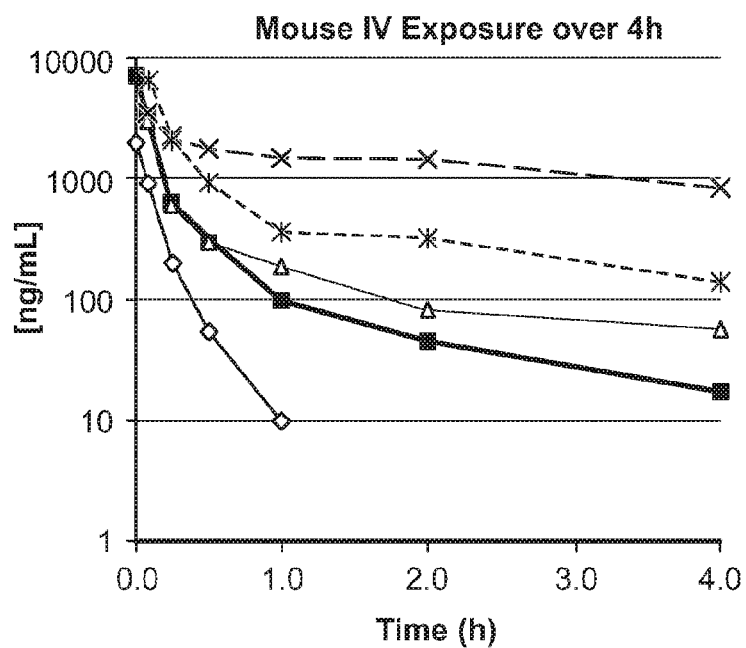
FIG. 8 is a line graph depicting the IV exposure in mice of several PPARδ agonists over the course of four hours.

A line graph comparing the mouse IV exposure of some of the compounds of the invention in comparison versus comparator compounds is shown in FIG. 8.

Example 8

Synthetic Preparation of Compound Embodiments

Abbreviations
Me methyl
Et ethyl
nPr n-propyl
iPr isopropyl
cPr cyclopropyl
nBu n-butyl
iBu isobutyl
Boc tert-butyloxycarbonyl
Ac acetyl
Ph phenyl
Tf trifluoromethanesulfonyl
Ts 4-methylphenylsulfonyl
EDCI 3-(3-dimethylaminopropyl)-1-ethylcarbodiimide
HOBt 1-hydroxybenzotriazole
HATU 1-[bis(dimethylamino)methylene]-1H-1,2,3-triazolo[4,5-b]pyridinium 3-oxide hexafluorophosphate
HBTU N,N,N',N'-Tetramethyl-O-(1H-benzotriazol-1-yl)uronium hexafluorophosphate
DIPEA diisopropylethylamine
Togni's reagent 3,3-dimethyl-1-(trifluoromethyl)-1,2-benziodoxole
DCM dichloromethane
DME dimethoxyethane
DMF N,N-dimethylformamide
DMF.DMA N,N-dimethylformamide dimethyl acetal
DMSO dimethylsulfoxide
TFA trifluoroacetic acid
THF tetrahydrofuran
MW microwave irradiation
aq Aqueous M concentration expressed in mol/L
RT room temperature
TLC thin lay chromatography
HPLC high-performance liquid chromatography
MPLC medium pressure liquid chromatography
LCMS liquid chromatography-mass spectrometry
ESI+ m/z values in mass spectroscopy (Ionization ESI)
ESI− m/z values in mass spectroscopy (Ionization ESI)
$^1$H NMR (DMSO-$d_6$) δ (ppm) of peak in $^1$H NMR in DMSO-$d_6$
s singlet (spectrum)
d doublet (spectrum)
t triplet (spectrum)
q quartet (spectrum)
dd double doublet (spectrum)
br broad line (spectrum)
m multiplet (spectrum).

General Scheme-I

[Structures 1–5 shown]

-continued

[Structure 6 shown]

Reagents and Conditions: a) mCPBA, Et$_2$O, -30° C. to 0° C., 12 h, 57%; b) NaIO$_4$, 1,4-dioxane, H$_2$O, RT, 24 h, 100%; c) Jones reagent, acetone, RT, 78%; d) H$_2$SO$_4$, MeOH, RT, 97%; e) CBr$_4$, PPh$_3$, THF, RT, 4 h, 72%.

General Scheme-II

[Structures shown]

R = H, F
R1 = Me, iPr

Reagents and Conditions: a) MeNH$_2$·HCl, Et$_3$N, NaBH$_4$, MeOH, RT.

General Scheme-III

[Structures shown]

Y = B(OH)$_2$, Bpin

X = Br, I

[Product structure shown]

R$_2$ = H, F, Cl
R$_3$ = H, Me

Reagents and Conditions: a) Pd(PPh$_3$)$_4$, K$_2$CO$_3$, DMF, H$_2$O, 90° C.

General Scheme-IV

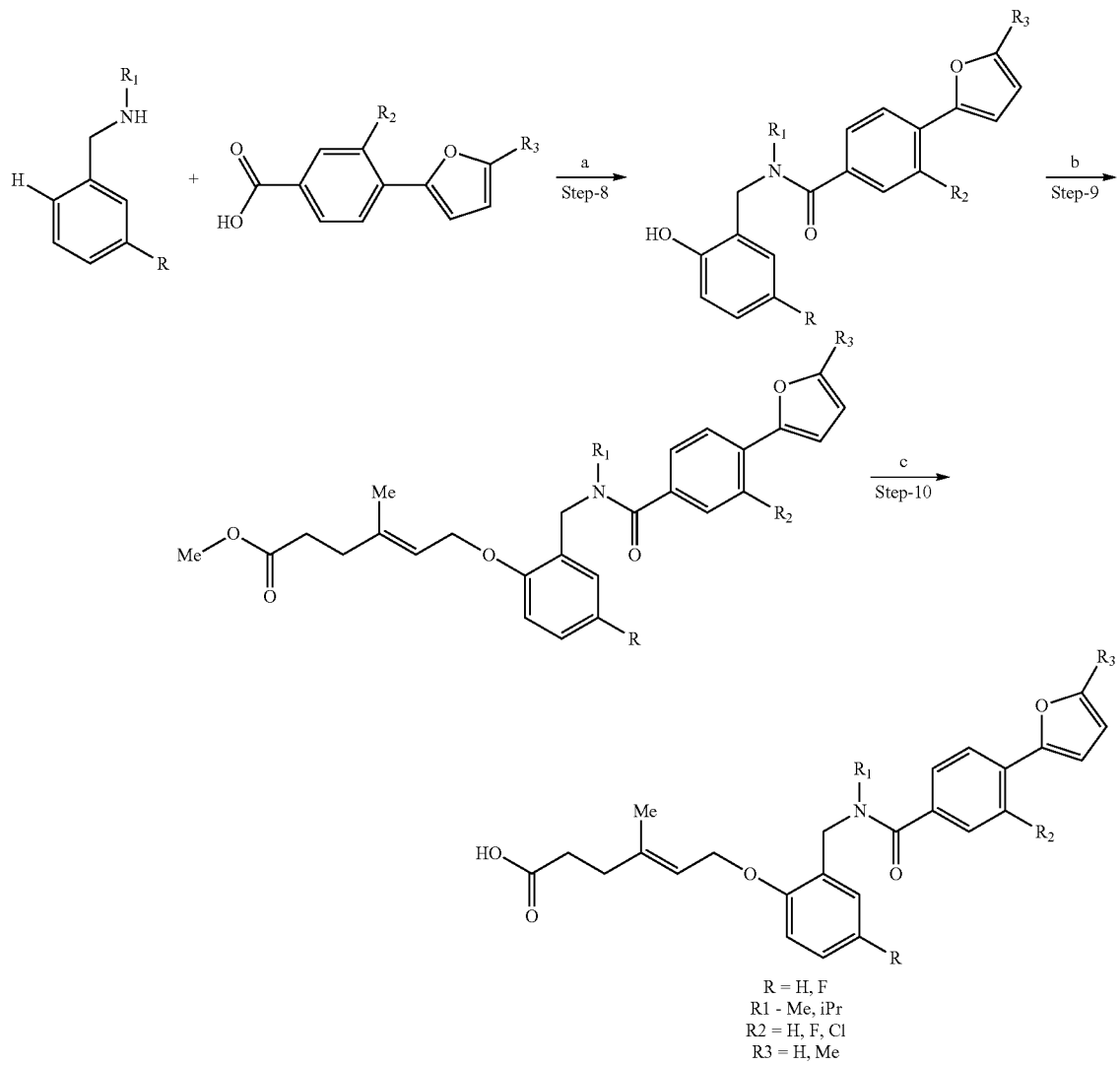

R = H, F
R1 - Me, iPr
R2 = H, F, Cl
R3 = H, Me

Reagents and Conditions: a) EDCl•HCl, HOBt, Et₃N, DMF, RT; b) Methyl (E)-6-bromo-4-methylhex-4-enoate, K₂CO₃, DMF, RT; c) LiOH•H₂O, THF, EtOH, H₂O, RT.

Example 8A

Synthesis of (E)-6-(2-((4-(furan-2-yl)-N-methylbenzamido)methyl)phenoxy)-4-methylhex-4-enoic acid (Compound 8a)

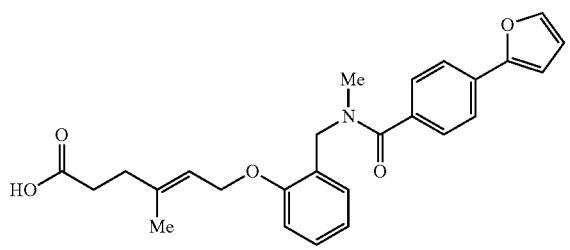 [SMILES: C/C(=C\COc1ccccc1CN(C)C(=O)c1ccc(-c2ccco2)cc1)CCC(=O)O]

Step 1: Synthesis of (E)-5-(3,3-dimethyloxiran-2-yl)-3-methylpent-2-en-1-yl acetate (Compound 8a-i)

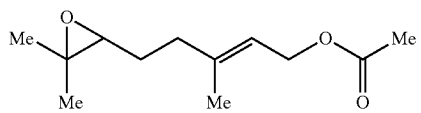 [SMILES: CC(=O)OC/C=C(\C)CCC1OC1(C)C]

In a 250 mL round bottom flask, a solution of geranyl acetate (2.0 g, 10.20 mmol) in diethyl ether (20 mL) was treated with a solution of mCPBA (5.01 g, 30.60 mmol) in diethyl ether (20 mL) dropwise at −30° C. Once the addition was complete, the temperature was allowed to rise to 0° C. The reaction mixture was stirred at same temperature for 6 h and then placed overnight in a cold room (+3° C.). After completion of the reaction (TLC), the reaction mixture was washed with 1 N NaOH (pH>10) and later with water till the washings were neutral pH. The extract was washed with brine, dried over anhydrous Na$_2$SO$_4$ and solvent was removed under reduced pressure. The crude residue was purified by silica gel column chromatography (elution, 10% EtOAc in hexanes) to afford the title compound. Yield: 1.21 g (57.1%).

$^1$H NMR (300 MHz, CDCl$_3$): δ 5.38 (t, J=6.0 Hz, 1H), 4.60 (d, J=7.2 Hz, 2H), 2.72 (t, J=6.3 Hz, 1H), 2.23-2.12 (m, 2H), 2.04 (s, 3H), 1.72 (s, 3H), 1.69-1.62 (m, 2H), 1.30 (s, 3H), 1.26 (s, 3H).

Step 2: Synthesis of (E)-3-methyl-6-oxohex-2-en-1-yl acetate (Compound 8a-ii)

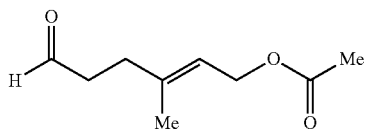 [SMILES: CC(=O)OC/C=C(\C)CCC=O]

In a 250 mL round bottom flask, a solution of (E)-5-(3, 3-dimethyloxiran-2-yl)-3-methylpent-2-en-1-yl acetate (1.0 g, 4.71 mmol) in 1,4-dioxane (15 mL) was treated with a solution of NaIO$_4$ (2.01 g, 9.43 mmol) in water (20 mL) at RT. The reaction mixture was stirred at same temperature for 24 h. After completion of reaction (TLC), the inorganic salts were filtered through Celite® pad. The filtrate was extracted with EtOAc (100 mL×3). The combined organic extract was washed with water, brine and dried over anhydrous Na$_2$SO$_4$. The solvent was removed under reduced pressure. The residue obtained was purified by silica gel column chromatography (gradient elution, 5-15% EtOAc in hexanes) to afford the title compound. Yield: 0.82 g (quant).

$^1$H NMR (400 MHz, CDCl$_3$): δ 9.80 (s, 1H), 5.36-5.35 (m, 1H), 4.58 (d, J=6.8 Hz, 2H), 2.59-2.37 (m, 4H), 2.35 (s, 3H), 1.71 (s, 3H).

Step 3: Synthesis of (E)-6-acetoxy-4-methylhex-4-enoic acid (Compound 8a-iii)

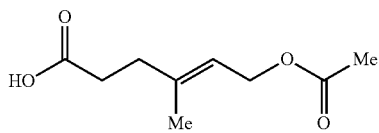 [SMILES: CC(=O)OC/C=C(\C)CCC(=O)O]

In a 250 mL round bottom flask, freshly prepared Jones reagent (10 mL) was added dropwise to a solution of (E)-3-methyl-6-oxohex-2-en-1-yl acetate (0.8 g, 4.54 mmol) in acetone (14 mL) till the orange color of solution persisted. After completion of the reaction (TLC), the reaction mixture was diluted with EtOAc and washed with water until pH 3. The organic layer was separated, washed with brine and dried over anhydrous Na$_2$SO$_4$. The solvent was removed under reduced pressure. The residue obtained was used in the next step without further purification. Yield: 0.66 g (crude).

$^1$H NMR (300 MHz, DMSO-d$_6$): δ 12.85 (brs, 1H) 5.27 (t, J=6.9 Hz, 1H), 4.50 (d, J=7.2 Hz, 2H), 2.33-2.18 (m, 4H), 1.99 (s, 3H), 1.64 (s, 3H).

Step 4: Synthesis of methyl (E)-6-hydroxy-4-methylhex-4-enoate (Compound 8a-iv)

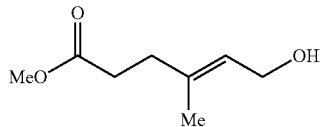 [SMILES: COC(=O)CC/C(C)=C/CO]

In a 100 mL round bottom flask, a solution of (E)-6-acetoxy-4-methylhex-4-enoic acid (1.1 g, 5.90 mmol) in methanol (20 mL) was treated with concentrated H$_2$SO$_4$ (3 drops). The reaction mixture was stirred for 12 h at RT. After completion of the reaction (TLC), the reaction mixture was diluted with EtOAc (100 mL) and washed with water. The organic layer was separated and dried over anhydrous Na$_2$SO$_4$. The solvent was removed under reduced pressure. The residue obtained was used in next step without further purification. Yield: 0.91 g.

$^1$H NMR (300 MHz, CDCl$_3$): δ 5.44 (t, J=6.9 Hz, 1H), 4.16 (d, J=6.9 Hz, 2H), 3.67 (s, 3H), 2.48-2.34 (m, 4H), 1.68 (s, 3H).

Step-5: Synthesis of methyl (E)-6-bromo-4-methyl-hex-4-enoate (Compound 8a-v)

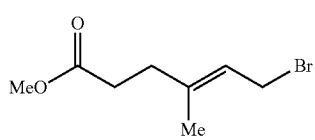

In a 100 mL round bottom flask, a solution of methyl (E)-6-hydroxy-4-methylhex-4-enoate (5.0 g, 31.6 mmol) in THF (90 mL) were treated with CBr$_4$ (15.61 g, 47.0 mmol) and PPh$_3$ (12.43 g, 47.0 mmol) under inert atmosphere. The reaction mixture was stirred for 4 h at RT. After completion of reaction (TLC), the reaction mixture was diluted with diethyl ether and the solid formed was filtered through a Celite® pad. The filtrate was dried over anhydrous Na$_2$SO$_4$. The solvent was removed under reduced pressure. The residue obtained was purified by silica gel column chromatography (gradient elution, 5-10% EtOAc in hexanes) to afford the title compound. Yield: 5.53 g (72.1%)

$^1$H NMR (400 MHz, CDCl$_3$): δ 5.57 (t, J=8.4 Hz, 1H), 4.03 (d, J=8.4 Hz, 2H), 3.68 (s, 3H), 2.47-2.38 (m, 4H), 1.74 (s, 3H).

Step-6: Synthesis of 2-((methylamino)methyl)phenol (Compound 8a-vi)

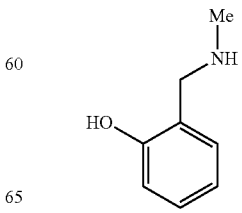

In a 250 mL round bottom flask, a solution of methyl amine hydrochloride (5.52 g, 81.8 mmol) in MeOH (50 mL) was treated with Et₃N (13.36 mL, 98.2 mmol) at RT. The mixture was stirred at RT for 30 min and treated with a solution of salicylaldehyde (10.0 g, 81.8 mmol) in MeOH (50 mL) at RT under nitrogen atmosphere. The resulting mixture was stirred at RT for 1 h. The mixture was cooled to 0° C. and NaBH₄ (3.09 g, 31.8 mmol) was added in portions at RT. The reaction mixture was stirred at RT for 2 h. Upon completion of reaction (TLC), the reaction mixture was concentrated under reduced pressure. The residue obtained was diluted with cold water and extracted with EtOAc (300 mL×2). The combined organic extract was washed with brine and dried over anhydrous Na₂SO₄. The solution was concentrated under reduced pressure to afford the title compound, which was used in next step without further purification. Yield: 9.11 g (81.3%).

¹H NMR (300 MHz, DMSO-d₆): δ 7.07-7.01 (m, 2H), 6.71-6.65 (m, 2H), 5.86 (brs, 2H), 3.75 (s, 2H), 2.25 (s, 3H).
LCMS (ESI+, m/z): 138.2 (M+H)⁺.

Step-7: Synthesis of 4-(furan-2-yl)benzoic acid (Compound 8a-vii)

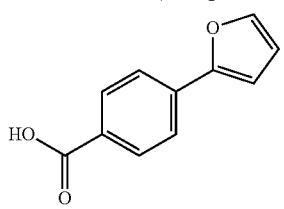

In a 100 mL resealable reaction tube, 4-iodobenzoic acid (15.0 g, 60.48 mmol) and furan-2-ylboronic acid (13.5 g, 129.0 mmol) were dissolved in degassed DMF (375 mL) and water (70 mL) at RT under nitrogen atmosphere. Pd(PPh₃)₄ (6.97 g, 6.0 mmol), K₂CO₃ (25.04 g, 181.2 mmol) were sequentially added to the above solution under nitrogen atmosphere. The resulting mixture was degassed by purging with argon gas for 15 min, and reaction mixture was heated to 90° C. until completion of the reaction (TLC). The reaction mixture was cooled to RT, diluted with cold water and washed with ethyl acetate (3×30 mL). The aqueous layer was separated and acidified to pH 3 with concentrated HCl, before extracting with EtOAc (400 mL×2). The combined extract was washed with brine, dried over anhydrous Na₂SO₄ and concentrated under reduced pressure to get the title compound as light yellow solid. Yield: 11.37 g (quant).

¹H NMR (300 MHz, DMSO-d₆): δ 12.95 (brs, 1H), 7.97 (d, J=8.1 Hz, 2H), 7.82-7.78 (m, 3H), 7.13 (d, J=3.6 Hz, 1H), 6.64-6.63 (m, 1H),
LCMS (ESI-, m/z): 186.9 (M-H)⁻.

Step 8: Synthesis of 4-(furan-2-yl)-N-(2-hydroxybenzyl)-N-methylbenzamide (Compound 8a-viii)

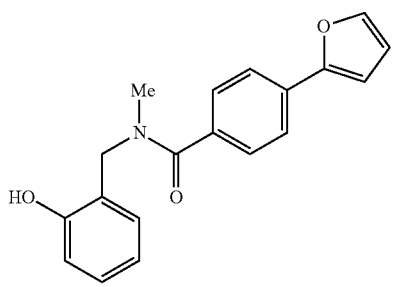 [SMILES: CN(Cc1ccccc1O)C(=O)c1ccc(-c2ccco2)cc1]

In a 250 mL round bottom flask, a stirred solution of 2-((methylamino)methyl)phenol (5.0 g, 36.44 mmol) and 4-(furan-2-yl)benzoic acid (6.82 g, 36.44 mmol) in DMF (50 mL) was treated with EDCI.HCl (10.44 g, 54.66 mmol), HOBt (7.42 g, 54.66 mmol) and Et₃N (10.2 mL, 72.89 mmol) at RT under nitrogen atmosphere. The reaction mixture was stirred at RT for 12 h under nitrogen atmosphere. Upon completion of reaction (TLC), the reaction mixture was diluted with cold water, and extracted with EtOAc (30 mL×2). The combined organic extract was washed with saturated NaHCO₃, brine and dried over anhydrous Na₂SO₄. The solution was concentrated under reduced pressure and residue obtained was purified by silica gel column chromatography (elution, 10% EtOAc-hexanes) to yield the title compound. Yield: 5.23 g (46.8%).

¹H NMR (300 MHz, CDCl₃): δ 9.89 (brs, 1H), 7.72 (d, J=8.4 Hz, 2H), 7.53-7.50 (m, 3H), 7.27-7.25 (m, 1H), 7.18 (d, J=9.0 Hz, 1H), 7.01 (d, J=7.8 Hz, 1H), 6.86 (t, J=7.5 Hz, 1H), 6.75 (d, J=3.3 Hz, 1H), 6.50-6.49 (m, 1H), 4.62 (s, 2H), 3.07 (s, 3H).
LCMS (ESI+, m/z): 307.8 (M+H)⁺.

Step-9: Synthesis of methyl (E)-6-(2-((4-(furan-2-yl)-N-methylbenzamido)methyl)phenoxy)-4-methylhex-4-enoate (Compound 8a-ix)

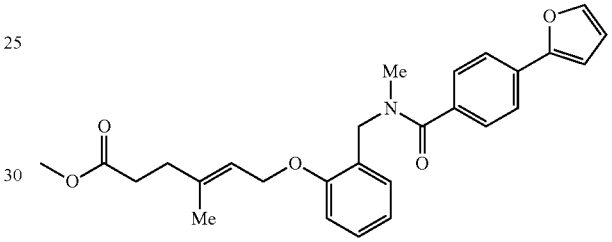

In a 250 mL round bottom flask, a stirred solution of 4-(furan-2-yl)-N-(2-hydroxybenzyl)-N-methylbenzamide (2.5 g, 8.14 mmol) in DMF (50 mL) was treated with K₂CO₃ (3.37 g, 24.42 mmol) and methyl (E)-6-bromo-4-methylhex-4-enoate (2.15 g, 9.77 mmol) at RT under nitrogen atmosphere. The resulting reaction mixture was stirred at RT for 12 h. After completion of the reaction (TLC), the reaction mixture was cooled to RT, filtered and washed with ethyl acetate. The filtrate was concentrated under reduced pressure and residue obtained was diluted with cold water (50 mL), before extracting with ethyl acetate (200 mL). The organic layer was washed with brine, dried over anhydrous Na₂SO₄ and concentrated under reduced pressure. The residue obtained was purified by silica gel column chromatography (gradient elution, 15-30% EtOAc in hexanes) to afford the title compound. Yield: 0.90 g (23.6%).

LCMS (ESI+, m/z): 448.3 (M+H)⁺ and 470.1 (M+Na)⁺.

Step-10: Synthesis of (E)-6-(2-((4-(furan-2-yl)-N-methylbenzamido)methyl)phenoxy)-4-methylhex-4-enoic acid (Compound 8a)

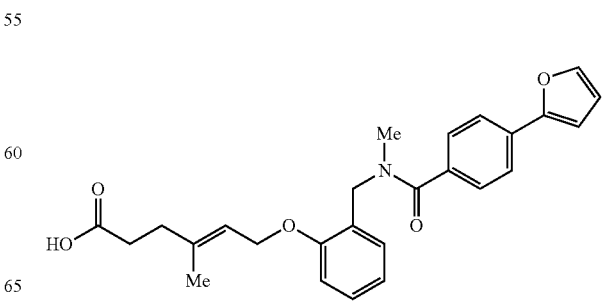

In a 100 mL round bottom flask, a stirred solution of methyl (E)-6-(2-((4-(furan-2-yl)-N-methylbenzamido)methyl)phenoxy)-4-methylhex-4-enoate (0.9 g, 1.88 mmol) in THF (20 mL), EtOH (6 mL) and water (6 mL), was treated with lithium hydroxide monohydrate (0.4 g, 9.43 mmol) at RT. The reaction mixture was stirred at RT for 3 h. Upon completion of reaction (TLC), the reaction mixture was concentrated under reduced pressure. The residue obtained was washed with EtOAc, diluted with cold water and acidified with 1 N HCl. The aqueous layer was extracted with EtOAc (25 mL×3). The combined organic extract was washed with brine and dried over anhydrous $Na_2SO_4$. The solution was concentrated under reduced pressure to give the title compound. Yield: 0.38 g (46.5%).

$^1$H NMR (400 MHz, DMSO-$d_6$, 90° C.): δ 11.80 (br, 1H), 7.73-7.72 (m, 3H), 7.47 (d, J=8.4 Hz, 2H), 7.27-7.19 (m, 2H), 7.02-6.95 (m, 3H), 6.59-6.58 (m, 1H), 5.44-5.42 (m, 1H), 4.58-4.55 (m, 4H), 2.51 (s, 3H), 2.33-2.28 (m, 4H), 1.69 (s, 3H).

LCMS (ESI+, m/z): 434.2 (M+H)$^+$ and 456.1 (M+Na)$^+$.
HPLC: 95.12%. (210 nm).

Example 8B

Synthesis of (E)-4-methyl-6-[2-[[methyl-(4-phenylbenzoyl)amino]methyl]phenoxy] hex-4-enoic acid (Compound 8b)

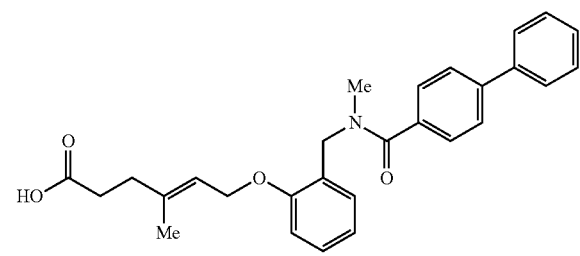 [SMILES: C/C(=C\COc1ccccc1CN(C)C(=O)c1ccc(-c2ccccc2)cc1)CCC(=O)O]

Step-1: Synthesis of N-[(2-hydroxyphenyl)methyl]-N-methyl-4-phenylbenzamide (Compound 8b-i)

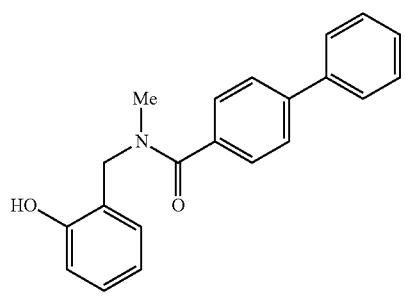 [SMILES: CN(Cc1ccccc1O)C(=O)c1ccc(-c2ccccc2)cc1]

In a 100 mL round bottom flask, a stirred solution of 2-((methylamino)methyl)phenol (1.0 g, 7.28 mmol) and 4-phenylbenzoic acid (1.44 g, 7.28 mmol) in DMF (20 mL) was treated with EDCl.HCl (1.65 g, 7.64 mmol), HOBt (1.17 g, 8.64 mmol) and Et$_3$N (1.46 mL, 10.8 mmol) at RT under nitrogen atmosphere. The reaction mixture was stirred at RT for 12 h under nitrogen atmosphere. Upon completion of reaction (TLC), the reaction mixture was diluted with cold water, and extracted with EtOAc (30 mL×2). The combined organic extract was washed with saturated NaHCO$_3$, brine and dried over anhydrous Na$_2$SO$_4$. The solution was concentrated under reduced pressure and residue obtained was purified by silica gel column chromatography (elution, 10% EtOAc-hexanes) to yield title compound. Yield: 0.51 g (22.1%).

$^1$H NMR (400 MHz, CDCl$_3$): δ 9.94 (brs, 1H), 7.65-7.56 (m, 6H), 7.50-7.37 (m, 3H), 7.31 (d, J=1.6 Hz, 1H), 7.20 (d, J=7.6 Hz, 1H), 7.02 (d, J=8.0 Hz, 1H), 6.87 (t, J=7.2 Hz, 1H), 4.64 (s, 2H), 3.10 (s, 3H).

LCMS (ESI+, m/z): 318.1 (M+H)$^+$.

Step-2: Synthesis of methyl (E)-4-methyl-6-[2-[[methyl-(4-phenylbenzoyl)amino]methyl]phenoxy]hex-4-enoate (Compound 8b-ii)

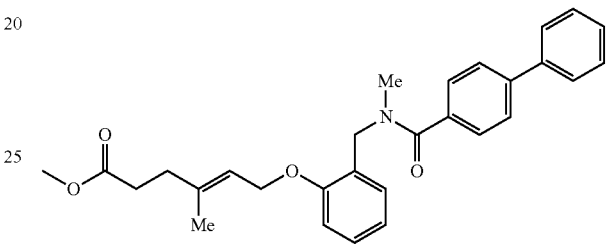

In a 100 mL round bottom flask, a solution of N-[(2-hydroxyphenyl)methyl]-N-methyl-4-phenyl-benzamide (0.43 g, 1.35 mmol) in DMF (15 mL) was treated with potassium carbonate (0.56 g, 4.05 mmol) and methyl (E)-6-bromo-4-methylhex-4-enoate (0.89 g, 4.06 mmol) at RT under nitrogen atmosphere. The resulting reaction mixture was heated at 70° C. with constant stirring for 12 h. The reaction mixture was cooled to RT, filtered and washed with ethyl acetate. The filtrate was concentrated under reduced pressure and residue obtained was diluted with cold water (50 mL), before extracting with ethyl acetate (200 mL). The organic extract was washed with brine, dried over anhydrous Na$_2$SO$_4$ and concentrated under reduced pressure. The residue obtained was purified by silica gel column chromatography (gradient elution, 15-30% EtOAc in hexanes) to afford the title compound. Yield: 0.24 g (38.2%).

LCMS (ESI+, m/z): 458.4 (M+H)$^+$ and 480.0 (M+Na)$^+$.

Step-3: Synthesis of (E)-4-methyl-6-[2-[[methyl-(4-phenylbenzoyl) amino] methyl] phenoxy] hex-4-enoic acid (Compound 8b-iii)

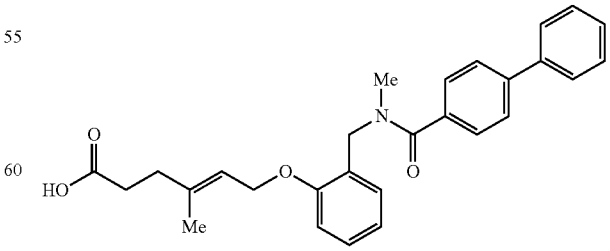

In a 100 mL round bottom flask, a stirred solution of methyl (E)-4-methyl-6-[2-[[methyl-(4-phenylbenzoyl)amino]methyl]phenoxy]hex-4-enoate (0.23 g, 0.502 mmol)

in THF (6 mL), EtOH (2 mL) and water (2 mL), was treated with lithium hydroxide monohydrate (0.105 g, 2.51 mmol) at RT. The reaction mixture was stirred at RT for 5 h. Upon completion of reaction (TLC), the reaction mixture was concentrated under reduced pressure. The residue was washed with EtOAc, diluted with cold water and acidified with 1 N HCl. The aqueous layer was extracted with EtOAc (25 mL×3). The combined organic extract was washed with brine and dried over anhydrous Na$_2$SO$_4$. The solution was concentrated under reduced pressure to give the crude residue. The product was purified over a silica gel preparative TLC (elution, 50% EtOAc in hexanes) to give the title compound. Yield: 0.031 g (13.9%; based on pure isolated material with HPLC purity >95%).

$^1$H NMR (400 MHz, DMSO-d$_6$, 60° C.): δ 7.72-7.68 (m, 4H), 7.52-7.46 (m, 4H), 7.40-7.39 (m, 1H), 7.28-7.20 (m, 2H), 7.03-6.96 (m, 2H), 5.45 (brs, 1H), 4.57 (br, 4H), 2.90 (s, 3H), 2.27 (m, 4H), 1.69 (s, 3H).

LCMS (ESI+, m/z): 444.2 (M+H)$^+$ and 466.2 (M+Na)$^+$.
HPLC: 96.30% (210 nm).

Example 8C

Synthesis of (E)-6-(2-((3-fluoro-4-(furan-2-yl)-N-methylbenzamido)methyl) phenoxy)-4-methylhex-4-enoic acid (Compound 8c)

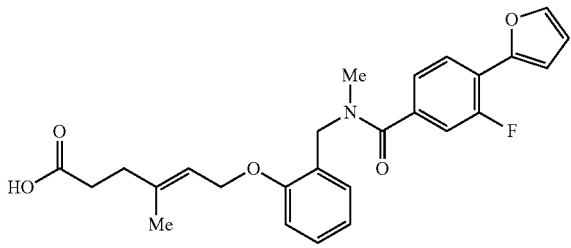 [SMILES: C/C(=C\COc1ccccc1CN(C)C(=O)c1ccc(-c2ccco2)c(F)c1)CCC(=O)O]

Step-1: Synthesis of 3-fluoro-4-(furan-2-yl)benzoic acid (Compound 8c-i)

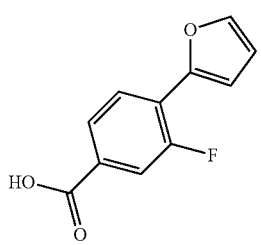 [SMILES: O=C(O)c1ccc(-c2ccco2)c(F)c1]

The title compound was synthesized from 4-bromo-3-fluorobenzoic acid (1.50 g, 6.84 mmol) and furan-2-ylboronic acid (1.53 g, 13.69 mmol) following the experimental procedure described in step-7 of Example 8A. Yield: 0.68 g (48.2%).

$^1$H NMR (400 MHz, DMSO-d$_6$): δ 13.35 (brs, 1H), 7.94-7.90 (m, 2H), 7.86 (d, J=8.4 Hz, 1H), 7.80 (d, J=8.0 Hz, 1H), 7.04 (t, J=1.8 Hz, 1H), 6.73-6.72 (m, 1H).

Step-2: Synthesis of 3-fluoro-4-(furan-2-yl)-N-(2-hydroxybenzyl)-N-methylbenzamide (Compound 8c-ii)

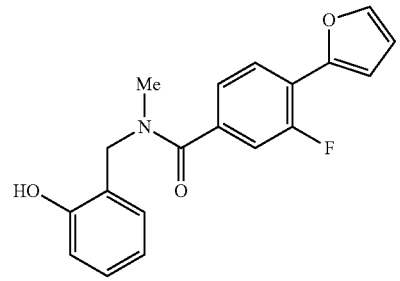

The title compound was synthesized from 2-((methylamino)methyl)phenol (0.4 g, 2.91 mmol) and 3-fluoro-4-(furan-2-yl)benzoic acid (0.60 g, 2.91 mmol) following the experimental procedure described in step-8 of Example 8A. Yield: 0.60 g (63.8%).

$^1$H NMR (300 MHz, CDCl$_3$): δ 9.73 (brs, 1H), 7.90 (t, J=7.8 Hz, 1H), 7.53 (brs, 1H), 7.35-7.28 (m, 2H), 7.18 (d, J=6.3 Hz, 2H), 7.01 (d, J=8.1 Hz, 1H), 6.95-6.92 (m, 1H), 6.82 (t, J=7.2 Hz, 1H), 6.55-6.53 (m, 1H), 4.61 (s, 2H), 3.08 (s, 3H).

LCMS (ESI+, m/z): 326.2 (M+H)$^+$.

Step-3: Synthesis of methyl (E)-6-(2-((3-fluoro-4-(furan-2-yl)-N-methylbenzamido) methyl)phenoxy)-4-methylhex-4-enoate (Compound 8c-iii)

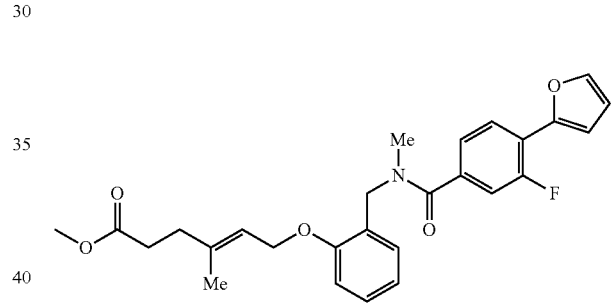

The title compound was synthesized from 3-fluoro-4-(furan-2-yl)-N-(2-hydroxy benzyl)-N-methylbenzamide (0.43 g, 1.32 mmol) and methyl (E)-6-bromo-4-methylhex-4-enoate (0.873 g, 3.96 mmol) following the experimental procedure described in step-9 of Example 8A. Yield: 0.310 g (50.4%).

LCMS (ESI, m/z): 466.2 (M+H)$^+$ and 488.3 (M+Na)$^+$.

Step-4: Synthesis of (E)-6-(2-((3-fluoro-4-(furan-2-yl)-N-methylbenzamido)methyl) phenoxy)-4-methylhex-4-enoic acid (Compound 8c)

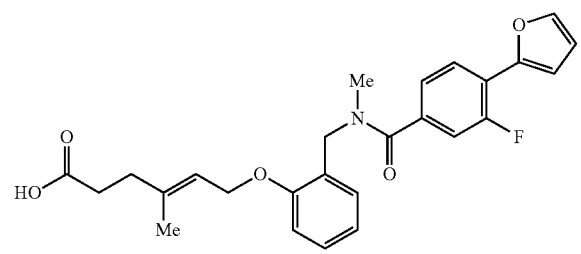

The title compound was synthesized from methyl (E)-6-(2-((3-fluoro-4-(furan-2-yl)-N-methylbenzamido)methyl)phenoxy)-4-methylhex-4-enoate (0.3 g, 0.64 mmol) following the experimental procedure described in step-10 of Example 8A. Yield: 0.110 g (32.2%).

$^1$H NMR (400 MHz, DMSO-d6, 90° C.): δ 11.78 (brs, 1H), 7.84-7.80 (m, 2H), 7.35-7.32 (m, 2H), 7.27 (t, J=7.6 Hz, 1H), 7.22 (d, J=7.2 Hz, 1H), 7.03 (d, J=8.0 Hz, 1H), 6.99 (t, J=7.2 Hz, 1H), 6.91-6.90 (m, 1H), 6.66-6.58 (m, 1H), 5.54 (brs, 1H), 4.58 (brs, 4H), 2.89 (s, 3H), 2.33-2.27 (m, 4H), 1.69 (s, 3H).

LCMS (ESI+, m/z): 452.1 (M+H)$^+$ and 474.1 (M+Na)$^+$

HPLC: 99.0% (210 nm).

Example 8D (E)-6-(2-((3-chloro-4-(furan-2-yl)-N-methylbenzamido)methyl)phenoxy)-4-methylhex-4-enoic acid (Compound 8d)

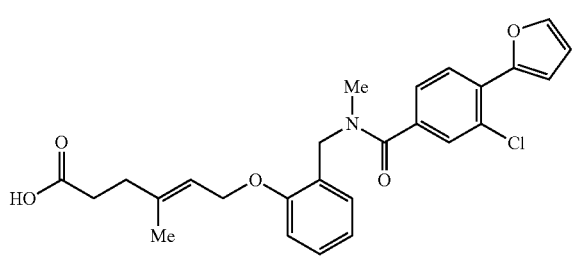

Step-1: Synthesis of 3-chloro-4-(furan-2-yl)benzoic acid (Compound 8d-i)

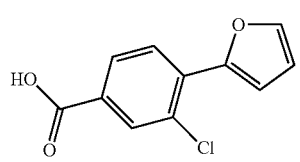 [SMILES: O=C(O)c1ccc(-c2ccco2)c(Cl)c1]

The title compound was synthesized from 3-chloro-4-bromobenzoic acid (2.0 g, 8.51 mmol) and furan-2-ylboronic acid (1.91 g, 17.02 mmol) following the experimental procedure described in step-7 of Example 8A. Yield: 1.53 g (79.8%)

$^1$H NMR (400 MHz, CD$_3$OD): δ 8.11 (s, 1H), 8.00 (s, 1H), 7.83 (s, 1H), 7.72 (d, J=1.2 Hz, 1H), 7.34 (d, J=3.2 Hz, 1H), 6.65-6.64 (m, 1H).

Step-2: Synthesis of 3-chloro-4-(furan-2-yl)-N-(2-hydroxybenzyl)-N-methylbenzamide (Compound 8d-ii)

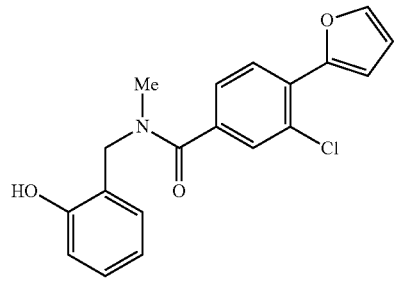 [SMILES: CN(Cc1ccccc1O)C(=O)c1ccc(-c2ccco2)c(Cl)c1]

The title compound was synthesized from 2-((methylamino)methyl)phenol (1.3 g, 5.85 mmol) and 3-chloro-4-(furan-2-yl)benzoic acid (0.96 g, 7.02 mmol) following the experimental procedure described in step-8 of Example 8A. Yield: 1.21 g (60.3%).

LCMS (ESI+, m/z): 342.1 (M+H)$^+$.

Step-3: Synthesis of methyl (E)-6-(2-((3-chloro-4-(furan-2-yl)-N-methylbenzamido) methyl)phenoxy)-4-methylhex-4-enoate (Compound 8d-iii)

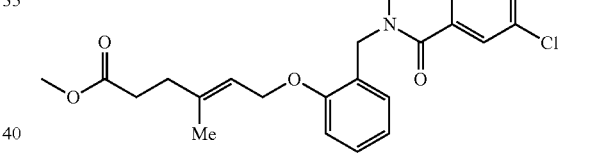

The title compound was synthesized from 3-chloro-4-(furan-2-yl)-N-(2-hydroxybenzyl)-N-methylbenzamide (0.4 g, 1.17 mmol) and methyl (E)-6-bromo-4-methylhex-4-enoate (0.39 g, 1.75 mmol) following the experimental procedure described in step-9 of Example 8A. Yield: 0.42 g (75.0%).

LCMS (ESI+, m/z): 482.1 (M+H)$^+$ and 504.0 (M+Na)$^+$.

Step-4: Synthesis of (E)-6-(2-((3-chloro-4-(furan-2-yl)-N-methylbenzamido) methyl)phenoxy)-4-methylhex-4-enoic acid (Compound 8d)

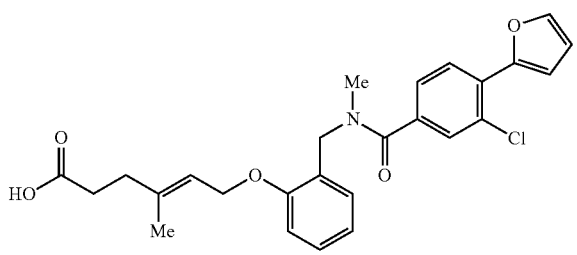

The title compound was synthesized from methyl (E)-6-(2-((3-chloro-4-(furan-2-yl)-N-methylbenzamido)methyl)phenoxy)-4-methylhex-4-enoate (0.41 g, 0.852 mmol) following the experimental procedure described in step-10 of Example 8A. Yield: 0.12 g (30.1%).

$^1$H NMR (400 MHz, DMSO-d$_6$, 90° C.): δ 7.86-7.82 (m, 2H), 7.55 (s, 1H), 7.47 (d, J=8.0 Hz, 1H), 7.27 (t, J=7.6 Hz, 1H), 7.22 (d, J=7.2 Hz, 1H), 7.17 (d, J=3.2 Hz, 1H), 7.03 (d, J=8.0 Hz, 1H), 6.98 (t, J=7.2 Hz, 1H), 6.67-6.66 (m, 1H), 5.44 (br s, 1H), 4.57 (br s, 4H), 2.89 (s, 3H), 2.32-2.27 (m, 4H), 1.69 (s, 3H).

LCMS (ESI+, m/z): 468.2 (M+H)$^+$ and 490.1 (M+Na)$^+$.

HPLC: 99.10% (210 nm).

Example 8E

Synthesis of (E)-4-methyl-6-(2-((N-methyl-4-(5-methylfuran-2-yl)benzamido) methyl)phenoxy)hex-4-enoic acid (Compound 8e)

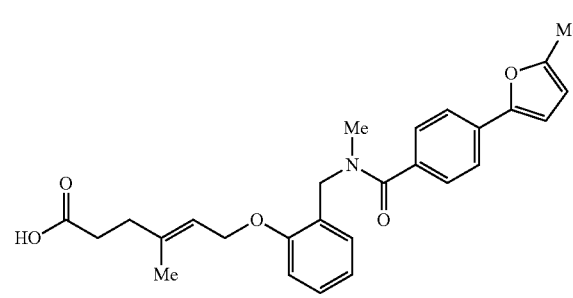

Step-1: Synthesis of 4-(5-methylfuran-2-yl)benzoic acid (Compound 8e-i)

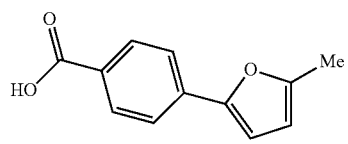 [SMILES: Cc1ccc(-c2ccc(C(=O)O)cc2)o1]

The title compound was synthesized from 4-iodobenzoic acid (2.0 g, 8.06 mmol) and 4,4,5,5-tetramethyl-2-(5-methylfuran-2-yl)-1,3,2-dioxaborolane (2.01 g, 9.67 mmol) following the experimental procedure described in step-7 of Example 8A. Yield: 1.96 g (crude)

$^1$H NMR (400 MHz, DMSO-d$_6$): δ 13.0 (br, 1H), 7.96 (d, J=8.4 Hz, 2H), 7.75 (d, J=8.4 Hz, 2H), 7.01 (d, J=3.2 Hz, 1H), 6.27 (m, 1H), 2.36 (s, 3H).

LCMS (ESI+, m/z): 203.2 (M+H)$^+$.

Step-2: Synthesis of N-(2-hydroxybenzyl)-N-methyl-4-(5-methylfuran-2-yl)benzamide (Compound 8e-ii)

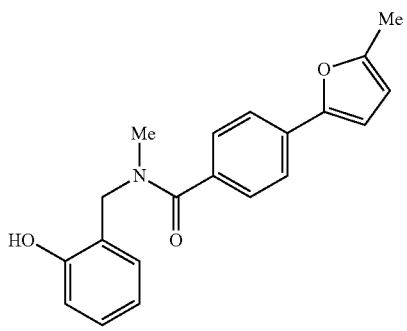 [SMILES: Cc1ccc(-c2ccc(C(=O)N(C)Cc3ccccc3O)cc2)o1]

The title compound was synthesized from 2-((methylamino)methyl)phenol (1.0 g, 7.29 mmol) and 4-(5-methylfuran-2-yl)benzoic acid (1.77 g, 8.75 mmol) following the experimental procedure described in step-8 of Example 8A. Yield: 1.52 g (64.1%)

$^1$H NMR (400 MHz, DMSO-d$_6$): δ 9.40 (brs, 1H), 7.67 (d, J=8.0 Hz, 2H), 7.46 (d, J=8.0 Hz, 2H), 7.16-7.10 (m, 2H), 6.86-6.81 (m, 3H), 6.20-6.19 (m, 1H), 4.56 (s, 2H), 2.92 (s, 3H), 2.36 (s, 3H).

LCMS (ESI+, m/z): 322.3 (M+H)$^+$.

Step-3: Synthesis of methyl (E)-4-methyl-6-(2-((N-methyl-4-(5-methylfuran-2-yl) benzamido) methyl)phenoxy)hex-4-enoate (Compound 8e-iii)

The title compound was synthesized from N-(2-hydroxybenzyl)-N-methyl-4-(5-methylfuran-2-yl)benzamide (0.5 g, 1.55 mmol) and methyl (E)-6-bromo-4-methylhex-4-enoate (0.516 g, 2.33 mmol) following the experimental procedure described in step-9 of Example 8A.

Yield: 0.26 g (37.3%)

$^1$H NMR (300 MHz, DMSO-d$_6$, 90° C.): δ 7.66 (d, J=8.0 Hz, 2H), 7.44 (d, J=8.4 Hz, 2H), 7.27 (t, J=7.2 Hz, 1H), 7.20 (d, J=7.2 Hz, 1H), 7.01-6.94 (m, 2H), 6.82 (d, J=3.2 Hz, 1H), 6.20 (d, J=2.8 Hz, 1H), 5.42 (brs, 1H), 4.57-4.55 (m, 4H), 3.57 (s, 3H), 2.89 (s, 3H), 2.41-2.25 (m, 4H), 2.36 (s, 3H), 1.69 (s, 3H).

LCMS (ESI+, m/z): 462.1 (M+H)$^+$ and 484.1 (M+Na)$^+$.

Step-4: Synthesis of (E)-4-methyl-6-(2-((N-methyl-4-(5-methylfuran-2-yl)benzamido) methyl)phenoxy) hex-4-enoic acid (Compound 8e)

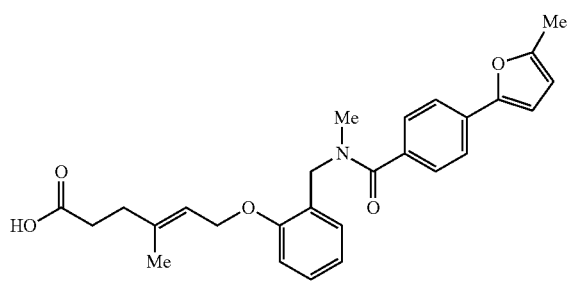 [SMILES: C/C(=C\COc1ccccc1CN(C)C(=O)c1ccc(-c2ccc(C)o2)cc1)CCC(=O)O]

The title compound was synthesized from methyl methyl (E)-4-methyl-6-(2-((N-methyl-4-(5-methylfuran-2-yl)benzamido)methyl)phenoxy)hex-4-enoate (0.26 g, 0.56 mmol) following the experimental procedure described in step-10 of Example 8A. Yield: 0.18 g (71.4%).

$^1$H NMR (300 MHz, DMSO-d$_6$, 90° C.): δ 7.67 (d, J=8.0 Hz, 2H), 7.45 (d, J=8.4 Hz, 2H), 7.25 (t, J=8.0 Hz, 1H), 7.19 (d, J=7.2 Hz, 1H), 7.02 (d, J=8.0 Hz, 1H), 6.97 (t, J=7.6 Hz, 1H), 6.83 (d, J=2.8 Hz, 1H), 6.20-6.19 (m, 1H), 5.39 (brs, 1H), 4.57-4.53 (m, 4H), 2.89 (s, 3H), 2.36 (s, 3H), 2.24 (t, J=8.4 Hz, 2H), 2.02 (t, J=8.4 Hz, 2H), 1.67 (s, 3H).

LCMS (ESI+, m/z): 448.2 (M+H)$^+$ and 470.1 (M+Na)$^+$.
HPLC: 93.7% (210 nm).

Example 8F

Synthesis of (E)-6-(2-((N,2-dimethylbenzofuran-5-carboxamido)methyl) phenoxy)-4-methylhex-4-enoic acid (Compound 8f)

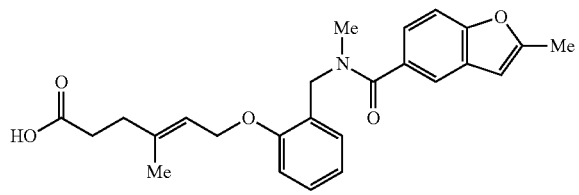 [SMILES: C/C(=C\COc1ccccc1CN(C)C(=O)c1ccc2oc(C)cc2c1)CCC(=O)O]

Step-1: Synthesis of N-(2-hydroxybenzyl)-N,2-dimethylbenzofuran-5-carboxamide (Compound 8f-i)

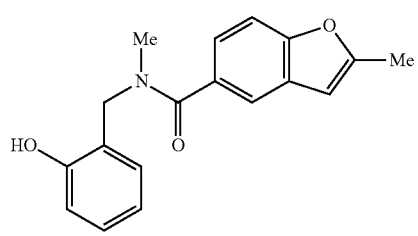 [SMILES: Cc1cc2cc(C(=O)N(C)Cc3ccccc3O)ccc2o1]

The title compound was synthesized from 2-((methylamino)methyl)phenol (0.2 g, 1.45 mmol) and 2-methylbenzofuran-5-carboxylic acid (0.26 g, 1.45 mmol) following the experimental procedure described in step-8 of Example 8A. Yield: 0.28 g (65.1%).

$^1$H NMR (300 MHz, CDCl$_3$): δ 10.14 (brs, 1H), 7.66 (d, J=1.5 Hz, 1H), 7.43 (d, J=8.4 Hz, 1H), 7.35 (d, J=1.5 Hz, 1H), 7.28-7.25 (m, 1H), 7.18 (d, J=9.0 Hz, 1H), 7.02 (d, J=8.1 Hz, 1H), 6.83 (t, J=1.2 Hz, 1H), 6.39 (s, 1H), 4.63 (s, 2H), 3.08 (s, 3H), 2.48 (s, 3H).

LCMS (ESI+, m/z): 296.1 (M+H)$^+$.

Step-2: Synthesis of methyl (E)-6-(2-((N,2-dimethylbenzofuran-5-carboxamido)methyl) phenoxy)-4-methylhex-4-enoate (Compound 8f-ii)

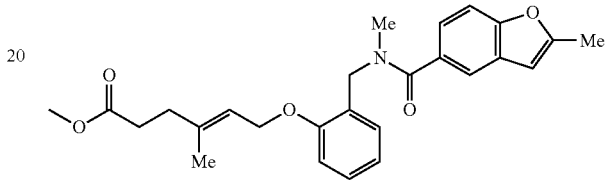

The title compound was synthesized from N-(2-hydroxybenzyl)-N,2-dimethylbenzofuran-5-carboxamide (0.28 g, 0.95 mmol) and methyl (E)-6-bromo-4-methylhex-4-enoate (0.271 g, 1.23 mmol) following the experimental procedure described in step-9 of Example 8A. Yield: 0.18 g (45.6%)

LCMS (ESI+, m/z): 436.4 (M+H)$^+$ and 458.3 (M+Na)$^+$.

Step-3: Synthesis of (E)-6-(2-((N,2-dimethylbenzofuran-5-carboxamido)methyl) phenoxy)-4-methylhex-4-enoic acid (Compound 8f)

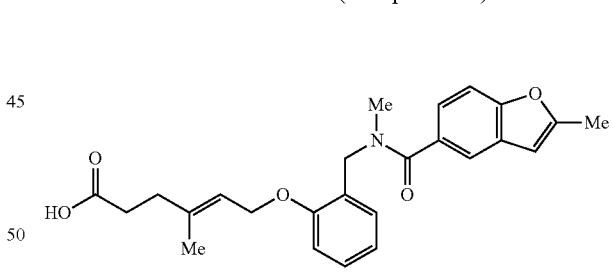

The title compound was synthesized from methyl (E)-6-(2-((N,2-dimethylbenzofuran-5-carboxamido)methyl)phenoxy)-4-methylhex-4-enoate (0.18 g, 0.41 mmol) following the experimental procedure described in step-10 of Example 8A. Yield: 0.085 g (48.8%).

$^1$H NMR (400 MHz, DMSO-d$_6$, 70° C.): δ 7.58 (br s, 1H), 7.49 (d, J=8.0 Hz, 1H), 7.27-7.19 (m, 3H), 7.02-6.95 (m, 2H), 6.59 (brs, 1H), 5.41 (s, 1H), 4.57-4.54 (m, 4H), 2.88 (s, 3H), 2.46 (s, 3H), 2.31-2.26 (m, 4H), 1.68 (s, 3H).

LCMS (ESI+, m/z): 422.2 (M+H)$^+$.
HPLC: 95.41% (210 nm).

Example-8G

Synthesis of (E)-6-(4-fluoro-2-((4-(furan-2-yl)-N-methylbenzamido) methyl) phenoxy)-4-methylhex-4-enoic acid (Compound 8g)

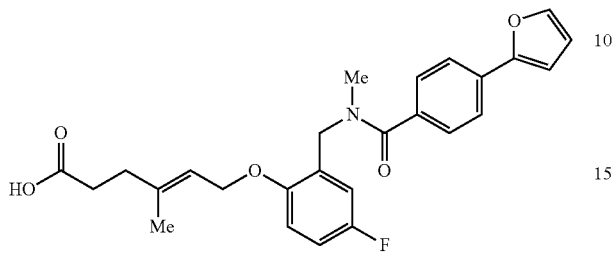

Step-1: Synthesis of 4-fluoro-2-((methylamino) methyl)phenol (Compound 8g-i)

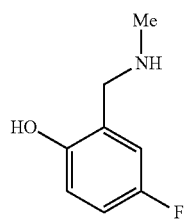 [SMILES: CNCc1cc(F)ccc1O]

The title compound was synthesized 5-fluoro-2-hydroxybenzaldehyde (1.5 g, 10.71 mmol) and methyl amine hydrochloride (3.58 g, 53.57 mmol) following the experimental procedure described in step-6 of Example 8A. Yield: 1.28 g (72.3%).

$^1$H NMR (400 MHz, CDCl$_3$): δ 6.82-6.87 (m, 1H), 6.56-6.68 (m, 2H), 3.92 (s, 2H), 2.47 (s, 3H).

LCMS (ESI+, m/z): 156.2 (M+H)$^+$.

Step-2: Synthesis of N-(5-fluoro-2-hydroxybenzyl)-4-(furan-2-yl)-N-methylbenzamide (Compound 8g-ii)

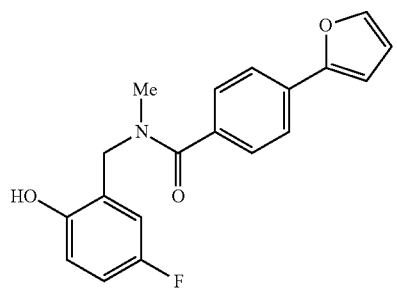 [SMILES: CN(Cc1cc(F)ccc1O)C(=O)c1ccc(-c2ccco2)cc1]

The title compound was synthesized from of 4-fluoro-2-((methylamino)methyl) phenol (0.844 g, 5.31 mmol) and 4-(furan-2-yl)benzoic acid (1.0 g, 5.31 mmol) following the experimental procedure described in step-8 of Example 8A. Yield: 1.23 g (71.1%).

$^1$H NMR (400 MHz, CDCl$_3$): δ 9.80 (brs, 1H), 7.71 (d, J=8.4 Hz, 2H), 7.52 (d, J=8.4 Hz, 2H), 7.51 (s, 1H), 6.99-6.87 (m, 3H), 6.74 (d, J=3.2 Hz, 1H), 6.50 (d, J=5.2 Hz, 1H), 4.58 (s, 2H), 3.09 (s, 3H).

LCMS (ESI+, m/z): 326.2 (M+H)$^+$.

Step-3: Synthesis of methyl (E)-6-(4-fluoro-2-((4-(furan-2-yl)-N-methylbenzamido) methyl)phenoxy)-4-methylhex-4-enoate (Compound 8g-iii)

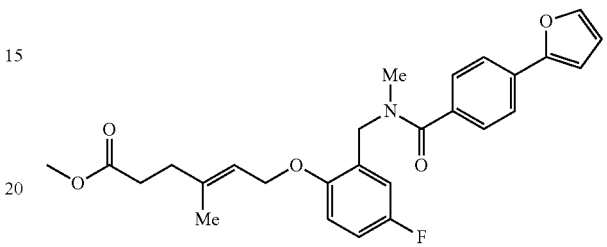

The title compound was synthesized from N-(5-fluoro-2-hydroxybenzyl)-4-(furan-2-yl)-N-methylbenzamide (0.4 g, 1.23 mmol) and methyl (E)-6-bromo-4-methylhex-4-enoate (0.815 g, 3.69 mmol) following the experimental procedure described in step-9 of Example 8A. Yield: 0.321 g (56.1%).

LCMS (ESI+, m/z): 466.1 (M+H)$^+$ and 488.2 (M+Na)$^+$.

Step-4: Synthesis of (E)-6-(4-fluoro-2-((4-(furan-2-yl)-N-methyl)-N-methylbenzamido) methyl)phenoxy)-4-methylhex-4-enoic acid (Compound 8g)

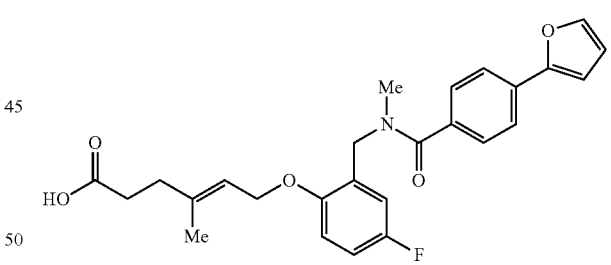

The title compound was synthesized from methyl (E)-6-(4-fluoro-2-((4-(furan-2-yl)-N-methylbenzamido)methyl) phenoxy)-4-methylhex-4-enoate (0.3 g, 0.645 mmol) following the experimental procedure described in step-10 of Example 8A. Yield: 0.225 g (77.3%)

$^1$H NMR (400 MHz, DMSO-d$_6$, 90° C.): δ 7.74-7.72 (m, 3H), 7.45 (d, J=8 Hz, 2H), 7.04-6.95 (m, 4H), 6.59 (brs, 1H), 5.42-5.39 (m, 1H), 4.56-4.54 (m, 4H), 2.92 (s, 3H), 2.32-2.27 (m, 4H) 1.68 (s, 3H).

LCMS (ESI+, m/z): 452.2 (M+H)$^+$ and 474.1 (M+Na)$^+$.

HPLC: 96.05% (210 nm).

Example 8H

Synthesis of 6-(2-((4-(furan-2-yl)-N-methylbenzamido)methyl)phenoxy)-4-methylhexanoic acid (Compound 8h)

Step-1: Synthesis of methyl 6-(2-((4-(furan-2-yl)-N-methylbenzamido)methyl)phenoxy)-4-methylhexanoate (Compound 8h-i)

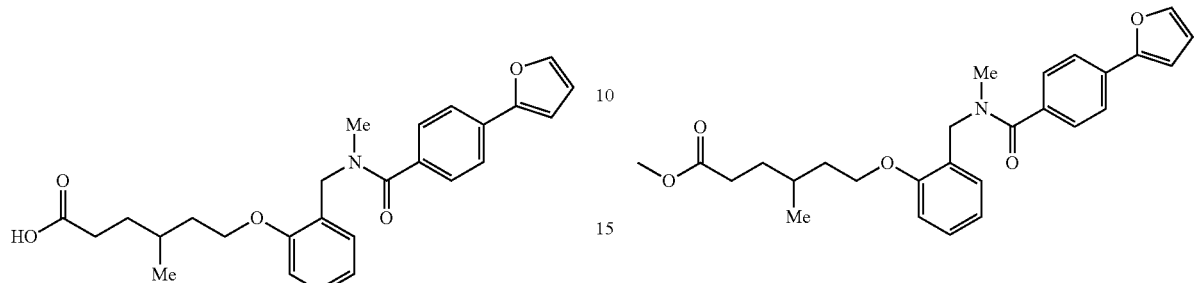

In 100 mL round bottom flask, a stirred and degassed solution of methyl (E)-6-(2-((4-(furan-2-yl)-N-methylbenzamido)methyl)phenoxy)-4-methylhex-4-enoate (0.40 g, Synthetic Scheme:

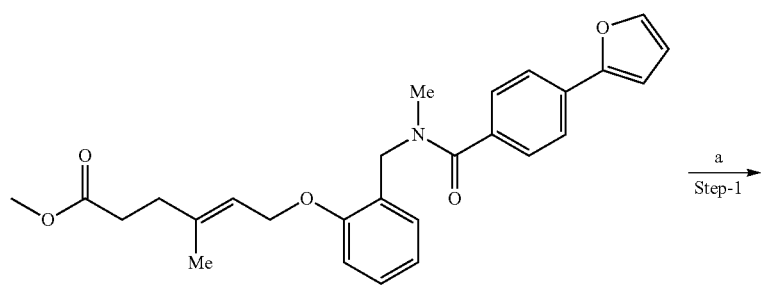 $\xrightarrow[\text{Step-1}]{a}$

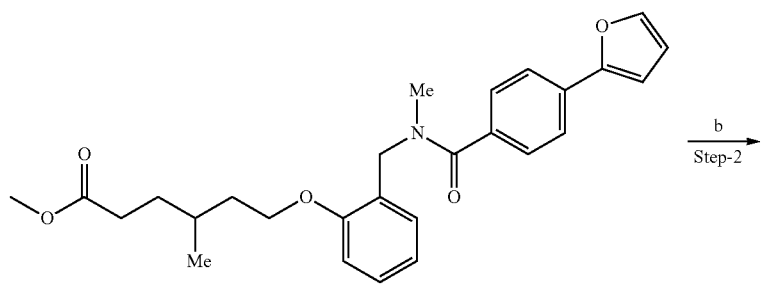 $\xrightarrow[\text{Step-2}]{b}$

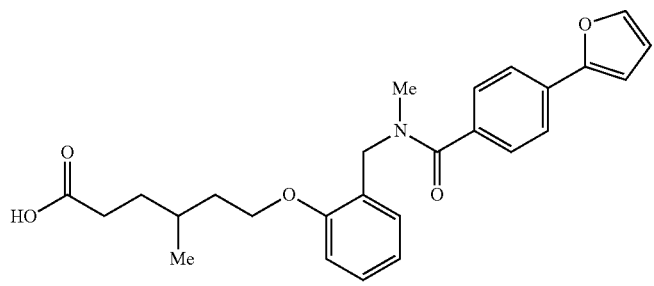

Reagents and conditions: a) Raney nickel, EtOH, H₂ (atm), RT, 5 h; b) LiOH·H₂O, THF, EtOH, H₂O, RT.

0.89 mmol) in EtOH (15 mL), was treated with Raney nickel (~100 mg) at RT. The reaction mixture was stirred at RT for 5 h under an atmosphere of hydrogen. Upon completion of reaction (TLC), the reaction mixture was filtered and concentrated under reduced pressure to afford the title compound. Yield: 0.385 g (96.0%).

LCMS (ESI+, m/z): 450.3 (M+H)+.

Step-2: Synthesis of 6-(2-((4-(furan-2-yl)-N-methylbenzamido)methyl)phenoxy)-4-methylhexanoic acid (Compound 8h)

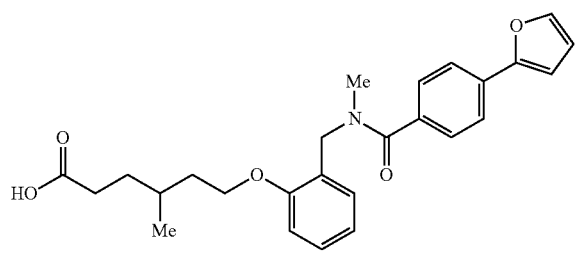 [SMILES: CC(CCOc1ccccc1CN(C)C(=O)c1ccc(-c2ccco2)cc1)CCC(=O)O]

The title compound was synthesized from methyl 6-(2-((4-(furan-2-yl)-N-methylbenzamido)methyl)phenoxy)-4-methylhexanoate (0.380 g, 0.85 mmol) following the experimental procedure described in step-10 of Example 8A. Yield: 0.231 g (62.7%).

$^1$H NMR (400 MHz, DMSO-$d_6$, 90° C.): δ 11.67 (brs, 1H), 7.74-7.72 (m, 3H), 7.48 (d, J=8.4 Hz, 2H), 7.28 (t, J=7.6 Hz, 1H), 7.21 (d, J=7.2 Hz, 1H), 7.02-6.95 (m, 3H), 6.60-6.59 (m, 1H), 4.59 (s, 2H), 4.05-4.01 (m, 2H), 2.91 (s, 3H), 2.24-2.19 (m, 2H), 1.74-1.42 (m, 5H), 0.91 (d, J=6.4 Hz, 3H).

LCMS (ESI+, m/z): 436.1 (M+H)+ and 458.1 (M+Na)+.
HPLC: 95.34% (210 nm).

Example 8I

Synthesis of (E)-6-(2-((4-(furan-2-yl)-N-methylbenzamido)methyl)phenoxy)-3-methylhex-2-enoic acid (Compound 8i)

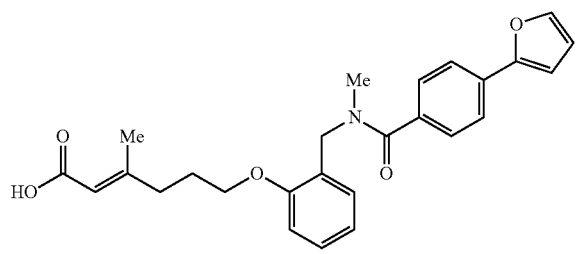 [SMILES: C/C(=C\C(=O)O)CCCOc1ccccc1CN(C)C(=O)c1ccc(-c2ccco2)cc1]

Synthetic Scheme:

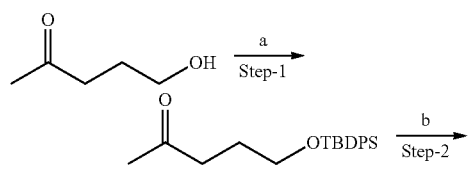

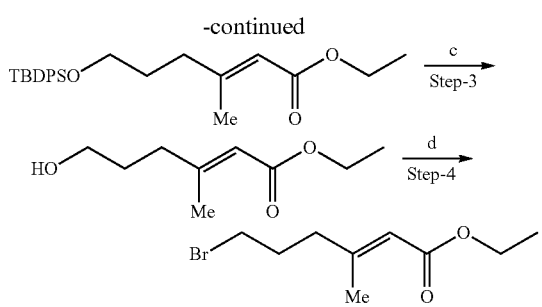

Reagents and conditions: a) TBDPSCl, imidazole, DCM, RT, 12 h; b) Triethyl phosphonoacetate, NaH, THF, RT, 12 h; c) TBAF (1.0M, THF), THF, RT, 30 min; d) CBr$_4$, PPh$_3$, THF, RT, 12 h.

Step-1: Synthesis of 5-((tert-butyldiphenylsilyl)oxy)pentan-2-one (Compound 8i-i)

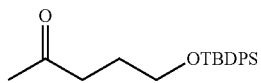

In a 100 mL round bottom flask, a solution of 5-hydroxypentan-2-one (5.0 g, 49.01 mmol) and imidazole (8.33 g, 122.5 mmol) in DCM (50 mL) was treated with TBDPSCl (16.16 g, 58.80 mmol) at 0° C. under N$_2$ atmosphere. The resulting reaction mixture was stirred at RT for 12 h. Upon completion of reaction (TLC), the reaction mixture was quenched with water and extracted with DCM (2×100 mL). The organic extract was separated and dried over anhydrous Na$_2$SO$_4$. The solvent was removed under reduced pressure. The residue obtained was purified by silica gel column chromatography (elution, 100% hexanes) to afford the title compound. Yield: 4.2 g (25.2%).

$^1$H NMR (300 MHz, CDCl$_3$): δ 7.73-7.64 (m, 4H), 7.42-7.35 (m, 6H), 3.66 (t, J=6.0 Hz, 2H), 2.54 (t, J=7.2 Hz, 2H), 2.13 (s, 3H), 1.90-1.73 (m, 2H), 1.04 (s, 9H).

Step-2: Synthesis of ethyl (E)-6-((tert-butyldiphenylsilyl)oxy)-3-methylhex-2-enoate (Compound 8i-ii)

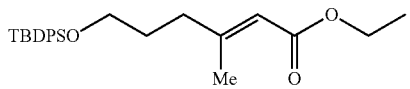

In a 100 mL two neck round bottom flask, a suspension of NaH (0.07 g, 1.75 mmol) in THF (10 mL) was treated with triethyl phosphonoacetate (0.29 mL, 1.47 mmol) at −78° C. under nitrogen atmosphere. The resulting reaction mixture was stirred for 30 min at −78° C. A solution of 5-((tert-butyldiphenylsilyl)oxy)pentan-2-one (0.51 g, 1.47 mmol) in THF (10 mL) was added dropwise to the above reaction mixture at −78° C. under nitrogen atmosphere. The reaction mixture was stirred for 12 h at RT under nitrogen atmosphere. Upon completion of reaction (TLC), the reaction mixture was quenched with ice cold water and extracted with EtOAc (2×100 mL). The organic extract was washed with brine (100 mL) and dried over anhydrous Na$_2$SO$_4$. The solvent was removed under reduced pressure. The residue obtained was purified by silica gel column chromatography (elution, 2% EtOAc in hexanes) to afford the title compound. Yield: 0.185 g (30.6%)

$^1$H NMR (300 MHz, CD$_3$OD): δ 7.67-7.64 (m, 4H), 7.42-7.39 (m, 6H), 5.68 (s, 1H), 4.12 (q, J=6.9 Hz, 2H), 3.66 (t, J=6.0 Hz, 2H), 2.24 (t, J=7.2 Hz, 2H), 2.17 (s, 3H), 1.78-1.73 (m, 2H), 1.25 (t, J=7.2 Hz, 3H), 1.04 (s, 9H).

Step-3: Synthesis of ethyl (E)-6-hydroxy-3-methyl-hex-2-enoate (Compound 8i-iii)

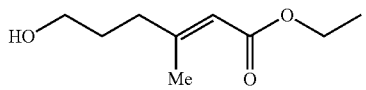

In a 50 mL round bottom flask, a solution of ethyl (E)-6-((tert-butyldiphenylsilyl)oxy)-3-methylhex-2-enoate (1.0 g, 2.43 mmol) in THF (15 mL) was treated with 1M solution of TBAF in THF (3.07 mL, 3.07 mmol) at 0° C. under nitrogen atmosphere. The resulting reaction mixture was stirred for 30 min at RT. Upon completion of reaction (TLC), the reaction mixture was diluted with water (50 mL) and extracted with EtOAc (2×100 mL). The organic extract was dried over anhydrous Na$_2$SO$_4$ and concentrated under reduced pressure. The residue obtained was purified by silica gel chromatography (elution, 20% EtOAc in hexanes) to yield the title compound. Yield: 0.33 g (78.7%).

$^1$H NMR (400 MHz, CDCl$_3$): δ 5.69 (s, 1H), 4.14 (q, J=7.2 Hz, 2H), 3.66 (t, J=6.4 Hz, 2H), 3.55 (br s, 1H); 2.24 (t, J=7.2 Hz, 2H), 2.17 (s, 3H), 1.78-1.73 (m, 2H), 1.27 (t, J=7.2 Hz, 3H)

LCMS (ESI+, m/z): 173.1 (M+H)$^+$.

Step-4: Synthesis of ethyl (E)-6-bromo-3-methyl-hex-2-enoate (Compound 8i-iv)

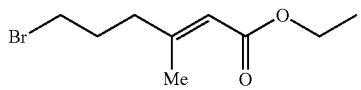

The title compound was synthesized from ethyl (E)-6-hydroxy-3-methylhex-2-enoate (0.33 g, 1.90 mmol) following the experimental procedure described in step-2 of Example 8CC.

Yield: 0.26 g (57.8%).

$^1$H NMR (400 MHz, CDCl$_3$): δ 5.70 (s, 1H), 4.16 (q, J=7.2 Hz, 2H), 3.39 (t, J=6.4 Hz, 2H), 2.30 (t, J=7.6 Hz, 2H), 2.16 (s, 3H), 2.06-2.00 (m, 2H), 1.27 (t, J=7.2 Hz, 3H).

Step-5: Synthesis of ethyl (E)-6-(2-((4-(furan-2-yl)-N-methylbenzamido)methyl) phenoxy)-3-methyl-hex-2-enoate (Compound 8i-v)

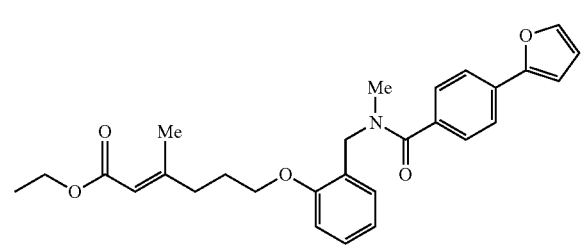 [SMILES: CCOC(=O)/C=C(\C)CCCOc1ccccc1CN(C)C(=O)c1ccc(-c2ccco2)cc1]

The title compound was synthesized from 4-(furan-2-yl)-N-(2-hydroxybenzyl)-N-methylbenzamide (0.30 g, 1.01 mmol) and ethyl (E)-6-bromo-3-methylhex-2-enoate (0.275 g, 1.07 mmol) following the experimental procedure described in step-3 of Example 8CC.

Yield: 0.42 g (93.3%).

LCMS (ESI+, m/z): 462.4 (M+H)$^+$ and 484.1 (M+Na)$^+$.

Step-5: Synthesis of (E)-6-(2-((4-(furan-2-yl)-N-methylbenzamido)methyl)phenoxy)-3-methylhex-2-enoic acid (Compound 8i)

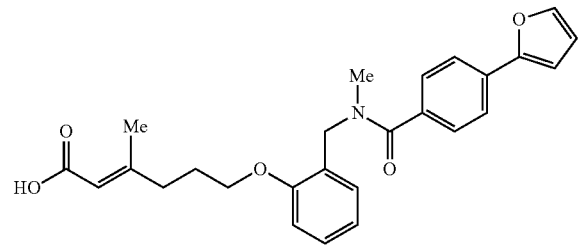 [SMILES: C/C(=C\C(=O)O)CCCOc1ccccc1CN(C)C(=O)c1ccc(-c2ccco2)cc1]

The title compound was synthesized from ethyl (E)-6-(2-((4-(furan-2-yl)-N-methylbenzamido)methyl)phenoxy)-3-methylhex-2-enoate (0.4 g, 0.86 mmol) following the experimental procedure described in step-4 of Example 8CC. Yield: 0.059 g, (15.6%).

$^1$H NMR (400 MHz, DMSO-d$_6$, 90° C.): δ 7.74-7.72 (m, 3H), 7.47 (d, J=8.4 Hz, 2H), 7.30-7.20 (m, 2H), 7.00-6.95 (m, 3H), 6.55-6.58 (m, 1H), 5.62 (s, 1H), 4.62 (s, 2H), 4.01 (t, J=6.0 Hz, 2H), 2.91 (s, 3H), 2.25 (t, J=7.2 Hz, 2H), 2.08 (s, 3H), 1.92-1.86 (m, 2H),

LCMS (ESI+, m/z): 434.4 (M+H)$^+$ and 456.1 (M+Na)$^+$.

HPLC: 99.14% (210 nm).

Example 8J

Synthesis of 6-(2-((4-(furan-2-yl)-N-methylbenzamido)methyl)phenoxy)-3-methylhexanoic acid (Compound 8j)

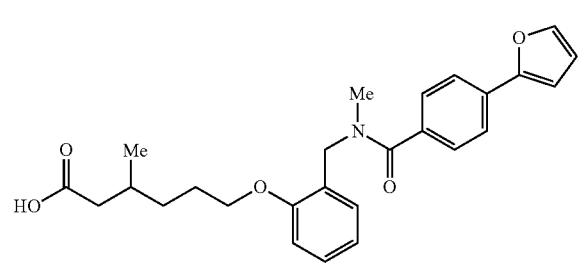 [SMILES: CC(CCCOc1ccccc1CN(C)C(=O)c1ccc(-c2ccco2)cc1)CC(=O)O]

Synthetic Scheme:

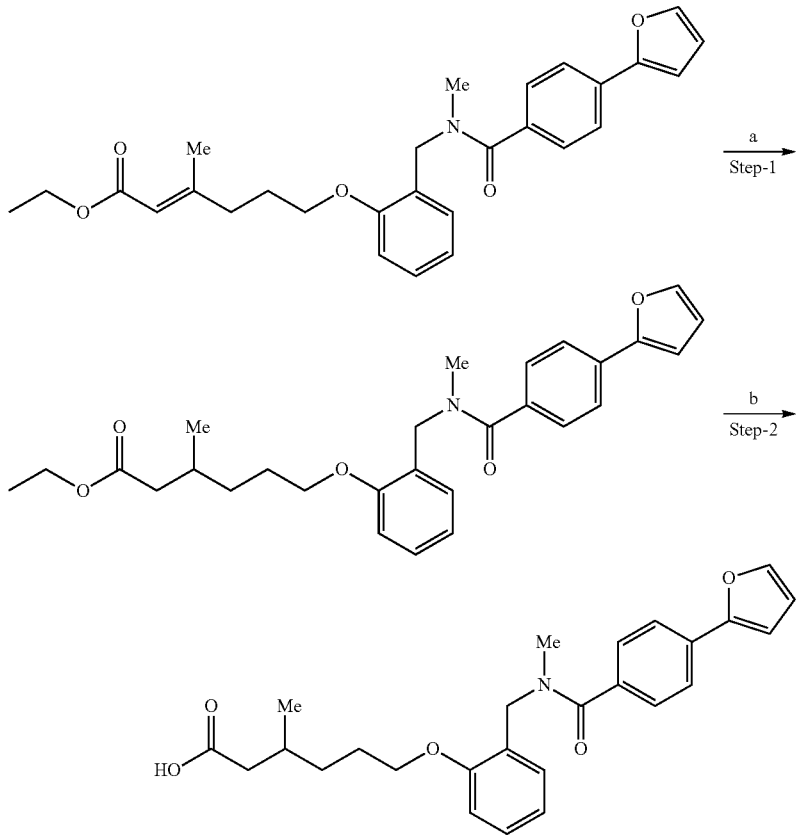

Reagents and conditions: a) NiCl₂•6H₂O, NaBH₄, MeOH; b) LiOH•H₂O, THF, EtOH, H₂O.

Step-1: Synthesis of ethyl 6-(2-((4-(furan-2-yl)-N-methylbenzamido)methyl)phenoxy)-3-methylhexanoate (Compound 8j-i)

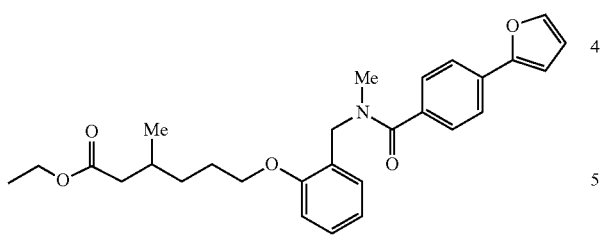

In a 50 mL round bottom flask, a solution of ethyl (E)-6-(2-((4-(furan-2-yl)-N-methylbenzamido)methyl)phenoxy)-3-methylhex-2-enoate (0.2 g, 0.44 mmol) in MeOH (10 mL) was treated sequentially with NiCl₂.6H₂O (0.016 g, 0.08 mmol) and NaBH₄ (0.050 g, 1.34 mmol) at 0° C. The reaction mixture was stirred at RT for 1 h. Upon completion of reaction (TLC), the reaction mixture was diluted with water and extracted with EtOAc (2×50 mL). The organic extract was washed with brine and dried over anhydrous Na₂SO₄. The solvent was removed under reduced pressure. The residue obtained was purified by Combi Flash (Silasep™, gradient elution, 10-15% EtOAc in hexanes) to afford the title compound. Yield: 0.15 g (72.5%).

LCMS (ESI+, m/z): 464.2 (M+H)⁺.

Step-2: Synthesis of 6-(2-((4-(furan-2-yl)-N-methylbenzamido)methyl)phenoxy)-3-methylhexanoic acid (Compound 8j)

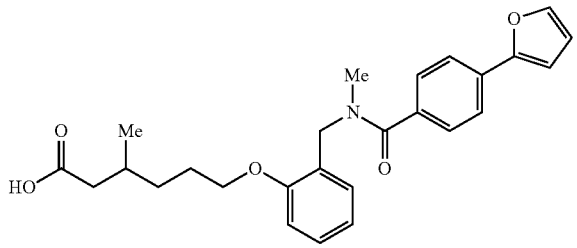 [SMILES: CC(CCCOc1ccccc1CN(C)C(=O)c1ccc(-c2ccco2)cc1)CC(=O)O]

The title compound was synthesized from ethyl 6-(2-((4-(furan-2-yl)-N-methylbenzamido)methyl)phenoxy)-3-methylhexanoate (0.15 g, 0.32 mmol) following the experimental procedure described in step-4 of Example 8CC. The residue was purified by preparative HPLC [Column: phenomenex (21.2×150 mm); Flow: 20 mL/min; mobile phase: A/B=0.01% TFA in water/MeCN; T/% B=0/20, 2/30/8/80] to afford the title compound. Yield: 0.072 g (51.1%).

¹H NMR (400 MHz, DMSO-d₆, 60° C.): δ 7.75 (s, 1H), 7.75 (d, J=7.6 Hz, 2H), 7.47 (d, J=7.6 Hz, 2H), 7.26 (m, 1H), 7.23-7.19 (m, 1H), 6.98-6.95 (m, 3H), 6.60 (brs, 1H), 4.58 (brs, 2H), 3.97 (brs, 2H), 2.90 (s, 3H), 2.22-2.19 (m, 1H), 2.03-1.99 (m, 1H), 1.86 (brs, 1H), 1.69 (brs, 2H), 1.42 (brs, 1H), 1.26 (brs, 1H), 0.89 (d, J=6.0 Hz, 3H).

LCMS (ESI+, m/z): 436.1 (M+H)⁺ and 458.1 (M+Na)⁺

HPLC: 98.2% (210 nm).

Example 8K

Synthesis of (E)-6-(2-((4-(furan-2-yl)-N-methylbenzamido)methyl)phenoxy)-2-methylhex-2-enoic acid (Compound 8k)

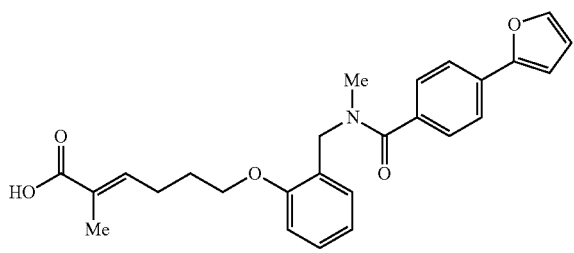 [SMILES: C/C(=C\CCCOc1ccccc1CN(C)C(=O)c1ccc(-c2ccco2)cc1)C(=O)O]

Scheme:

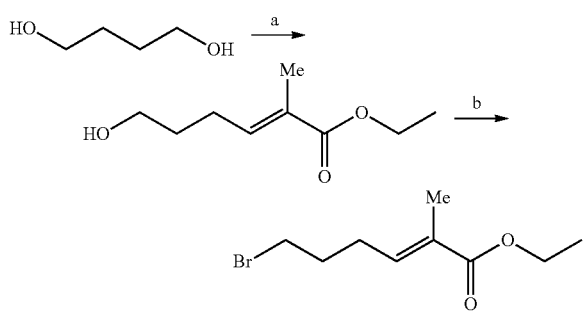

Reagents and conditions: a) (1-Ethoxycarbonylethylidene)triphenylphosphorane, MnO₂, DCM, 12 h; b) CBr₄, PPh₃, THF, RT, 12 h.

Step-1: Synthesis of ethyl (E)-6-hydroxy-2-methylhex-2-enoate (Compound 8k-i)

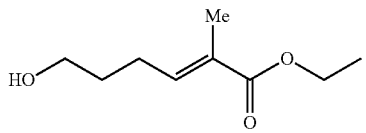

The title compound was synthesized from butane-1,4-diol (1.5 g, 16.62 mmol) and (1-ethoxycarbonylethylidene)triphenylphosphorane (14.41 g, 39.88 mmol) following the experimental procedure described in step-1 of Example 8CC. Yield: 1.28 g (44.7%).

$^1$H NMR (400 MHz, CDCl$_3$): δ 6.76 (t, J=7.6 Hz, 1H), 4.19 (q, J=7.2 Hz, 2H), 3.68 (t, J=6.4 Hz, 2H), 2.28 (t, J=7.2 Hz, 2H), 2.04-1.99 (m, 2H), 1.87 (s, 3H), 1.29 (t, J=7.2 Hz, 3H).

LCMS (ESI+, m/z): 173.4 (M+H)$^+$.

Step-2: Synthesis of ethyl (E)-6-bromo-2-methylhex-2-enoate (Compound 8k-ii)

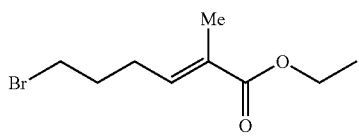

The title compound was synthesized from ethyl (E)-6-hydroxy-2-methylhex-2-enoate (0.6 g, 3.48 mmol) following the experimental procedure described in step-2 of Example 8CC.

Yield: 0.465 g (56.7%).

$^1$H NMR (400 MHz, CDCl$_3$): δ 6.69 (t, J=7.6 Hz, 1H), 4.19 (q, J=7.2 Hz, 2H), 3.42 (t, J=6.4 Hz, 2H), 2.35 (q, J=7.2 Hz, 2H), 2.04-1.99 (m, 2H), 1.87 (s, 3H), 1.29 (t, J=7.2 Hz, 3H).

LCMS (ESI+, m/z): 235.1, 237.1 (M+H)$^+$.

Step-3 Synthesis of ethyl (E)-6-(2-((4-(furan-2-yl)-N-methylbenzamido)methyl) phenoxy)-2-methylhex-2-enoate (Compound 8k-iii)

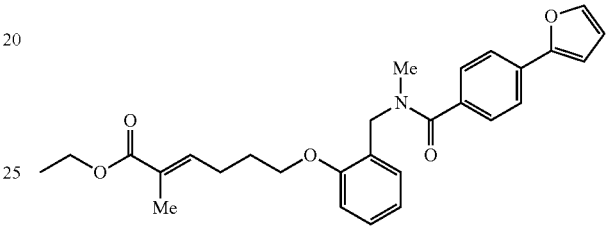

The title compound was synthesized from 4-(furan-2-yl)-N-(2-hydroxybenzyl)-N-methylbenzamide (0.5 g, 1.62 mmol) and ethyl (E)-6-bromo-2-methylhex-2-enoate (0.459 g, 1.94 mmol) following the experimental procedure described in step-3 of Example 8CC.

Yield: 0.408 g (54.4%).

LCMS (ESI+, m/z): 462.2 (M+H)$^+$ and 484.1 (M+Na)$^+$.

Step-4 Synthesis of (E)-6-(2-((4-(furan-2-yl)-N-methylbenzamido)methyl)phenoxy)-2-methylhex-2-enoic acid (Compound 8k-iv)

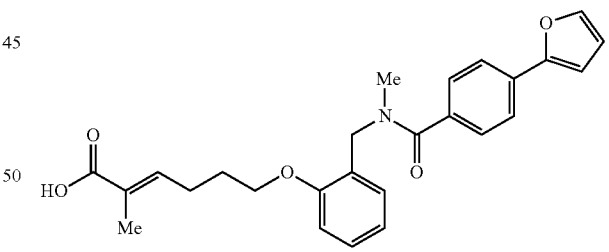

The title compound was synthesized from ethyl (E)-6-(2-((4-(furan-2-yl)-N-methylbenzamido)methyl)phenoxy)-2-methylhex-2-enoate (0.4 g, 0.87 mmol) following the experimental procedure described in step-4 of Example 8CC. Yield: 0.112 g (30.0%).

$^1$H NMR (400 MHz, DMSO-d$_6$, 80° C.): δ 7.73 (s, 1H), 7.72 (d, J=8.4 Hz, 2H), 7.47 (d, J=8.4 Hz, 2H), 7.26 (m, 1H), 7.20 (d, J=7.2 Hz, 1H), 7.00-6.96 (m, 3H), 6.75 (brs, 1H), 6.60-6.56 (m, 1H), 4.60 (s, 2H), 4.01 (t, J=6.0 Hz, 2H), 2.09 (s, 3H), 2.28 (brs, 2H), 1.86-1.83 (m, 2H), 1.71 (s, 3H).

LCMS (ESI+, m/z): 434.2 (M+H)$^+$ and 456.0 (M+Na)$^+$

HPLC: 95.12% (210 nm).

Example 8L
Synthesis of (E)-7-(2-((4-(furan-2-yl)-N-methylbenzamido)methyl)phenyl) hept-6-enoic acid (Compound 8F)
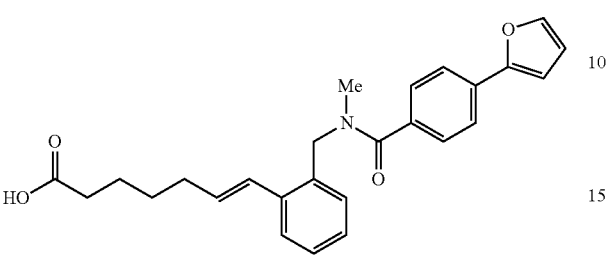
Synthetic Scheme:
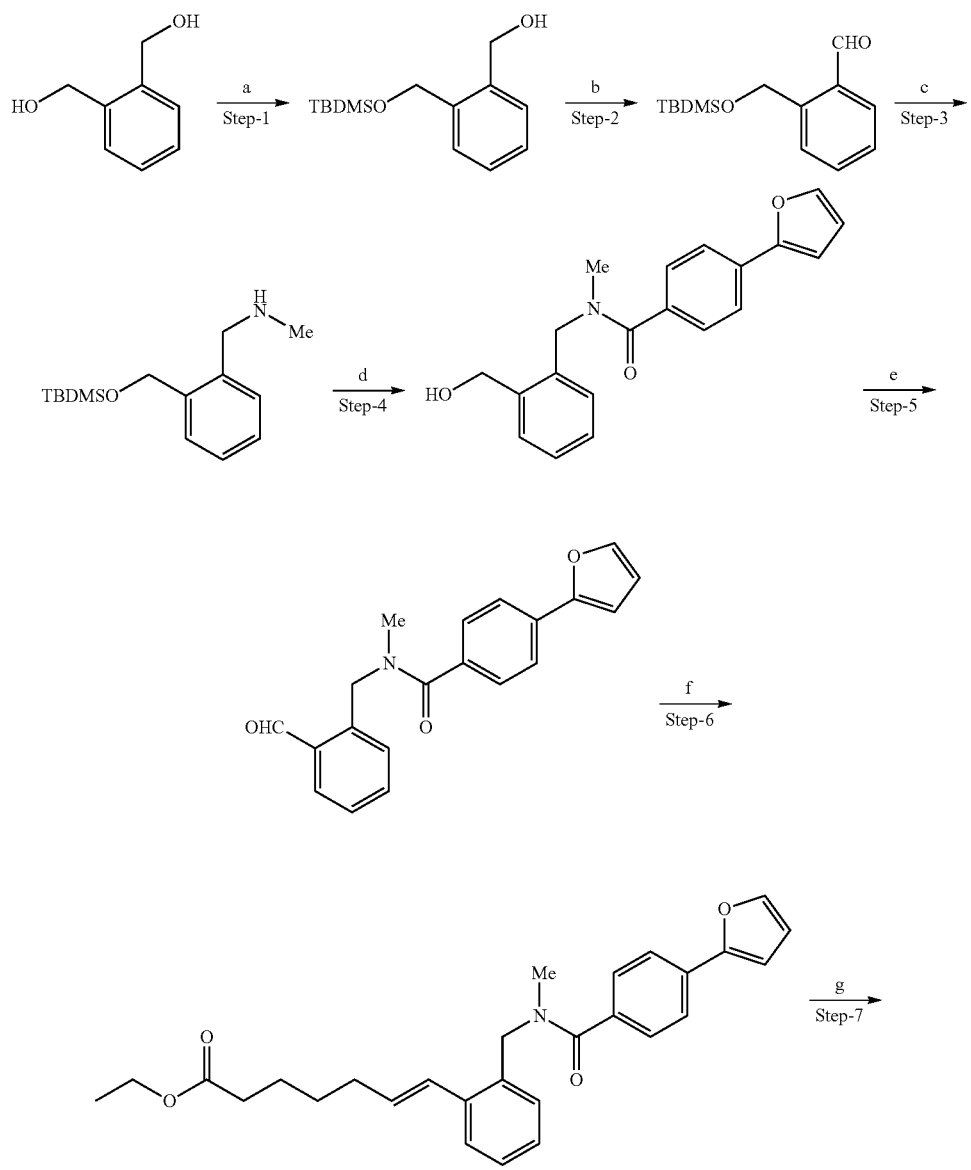

-continued

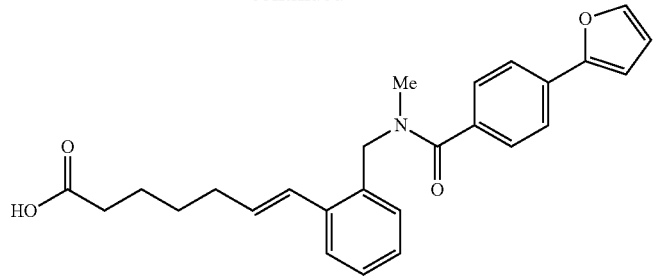 [SMILES: CN(Cc1ccccc1/C=C/CCCCC(=O)O)C(=O)c1ccc(-c2ccco2)cc1]

Reagents and conditions: a) TBDMSCl, imidazole, DCM, RT, 12 h; b) MnO₂, DCM, 12 h, RT; c) MeNH₂•HCl, NaBH₄, MeOH, 12 h, RT; d) 4-(Furan-2-yl)benzoic acid, EDCI•HCl, HOBt, Et₃N, DMF, RT; e) MnO₂, DCM, 12 h, RT: f) Ethyl 6-hexanoate triphenylphosphonium bromide, K₂CO₃, 18-Crown-6, THF, 12 h, 60° C.; g) LiOH•H₂O, THF, EtOH, H₂O, 12 h, RT.

Step-1: Synthesis of (2-(((tert-butyldimethylsilyl)oxy)methyl)phenyl)methanol (Compound 8t-i)

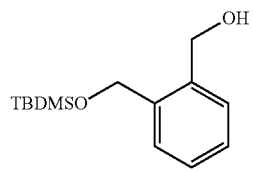 [SMILES: CC(C)(C)[Si](C)(C)OCc1ccccc1CO]

The title compound was synthesized from 1,2-phenylenedimethanol (3.6 g, 26.08 mmol) and TBDMSCl (3.14 g, 20.86 mmol) following the experimental procedure described in step-1 of example-12. Yield: 2.1 g (32.0%).

¹H NMR (400 MHz, DMSO-d₆): δ 7.34-7.36 (m, 2H), 7.25-7.23 (m, 2H), 5.07 (t, J=5.6 Hz, 1H), 4.74 (s, 2H), 4.52 (d, J=5.2 Hz, 2H), 0.90 (s, 9H), 0.07 (s, 6H).

Step-2: Synthesis of 2-(((tert-butyldimethylsilyl)oxy)methyl)benzaldehyde (Compound 8l-ii)

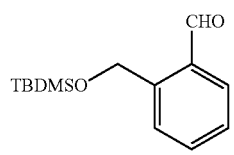 [SMILES: CC(C)(C)[Si](C)(C)OCc1ccccc1C=O]

In a 100 mL round bottom flask, a solution of (2-(((tert-butyldimethylsilyl)oxy)methyl)phenyl)methanol (2.0 g, 7.93 mmol) in DCM (20 mL) was treated with MnO₂ (14.0 g, 158.73 mmol) at RT. The resulting reaction mixture was stirred at RT for 12 h. Upon completion of reaction (TLC), the reaction mixture was filtered through a Celite® pad. The filtrate was concentrated under reduced pressure to get the title compound. Yield: 1.9 g (96.0%).

¹H NMR (400 MHz, DMSO-d₆): δ 10.2 (s, 1H), 7.91 (d, J=7.2 Hz, 1H), 7.70-7.68 (m, 2H), 7.52 (d, J=7.2 Hz, 1H), 5.11 (s, 2H), 0.90 (s, 9H), 0.08 (s, 6H).

Step-3: Synthesis of 1-(2-(((tert-butyldimethylsilyl)oxy)methyl)phenyl)-N-methylmethanamine (Compound 8f-iii)

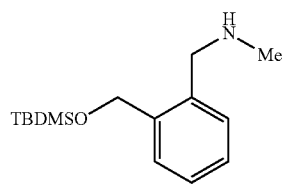 [SMILES: CNCc1ccccc1CO[Si](C)(C)C(C)(C)C]

In a 250 mL round bottom flask, a solution of methyl amine hydrochloride (0.485 g, 7.18 mmol) in MeOH (10 mL) was treated with Et₃N (1.18 mL, 8.62 mmol) at RT. The mixture was stirred at RT for 30 min. A solution of 2-(((tert-butyldimethylsilyl)oxy)methyl)benzaldehyde (1.8 g, 7.18 mmol) in MeOH (10 mL) was added to the above solution at RT under nitrogen atmosphere. The resulting mixture was stirred at RT for 12 h. The mixture was cooled to 0° C. and NaBH₄ (0.275 g, 7.18 mmol) was added in portions. The reaction mixture was stirred at RT for further 2 h. Upon completion of reaction (TLC), the reaction mixture was concentrated under reduced pressure. The residue obtained was diluted with cold water and extracted with EtOAc (300 mL×2). The combined organic extract was washed with brine and dried over anhydrous Na₂SO₄. The solution was concentrated under reduced pressure to afford the title compound, which was used in next step without further purification. Yield: 1.4 g (73.6%).

¹H NMR (400 MHz, DMSO-d₆): δ 7.39-7.32 (m, 5H), 4.80 (s, 2H), 3.65 (s, 2H), 2.29 (s, 3H), 0.90 (s, 9H), 0.08 (s, 6H).

LCMS (ESI+, m/z): 266.3 (M+H)⁺.

Step-4: Synthesis of 4-(furan-2-yl)-N-(2-(hydroxymethyl)benzyl)-N-methylbenzamide (Compound 8l-iv)

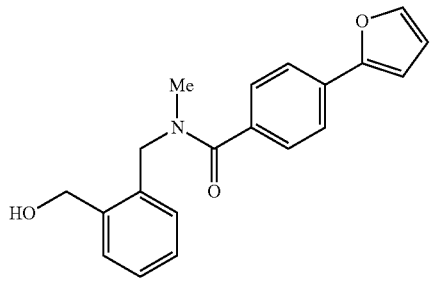 [SMILES: CN(Cc1ccccc1CO)C(=O)c1ccc(-c2ccco2)cc1]

In a 250 mL round bottom flask, a stirred solution of 1-(2-(((tert-butyldimethylsilyl)oxy)methyl)phenyl)-N-methylmethanamine (1.4 g, 5.26 mmol) and 4-(furan-2-yl)benzoic acid (0.9 g, 4.78 mmol) in DMF (10 mL) was treated with EDCI.HCl (1.11 g, 5.74 mmol), HOBt (0.78 g, 5.74 mmol) and Et₃N (1 mL, 7.17 mmol) at RT under nitrogen atmosphere. The reaction mixture was stirred at RT for 12 h under nitrogen atmosphere. Upon completion of reaction (TLC), the reaction mixture was diluted with cold water, and extracted with EtOAc (30 mL×2). The combined organic extract was washed with saturated NaHCO₃, brine and dried over anhydrous Na₂SO₄. The solution was concentrated under reduced pressure and residue obtained was purified by silica gel column chromatography (elution, 10% EtOAc in hexanes) to yield the title compound. Yield: 1.0 g (65.4%).

LCMS (ESI+, m/z): 322.1 (M+H)⁺.

Step-5: Synthesis of N-(2-formylbenzyl)-4-(furan-2-yl)-N-methylbenzamide (Compound 8l-v)

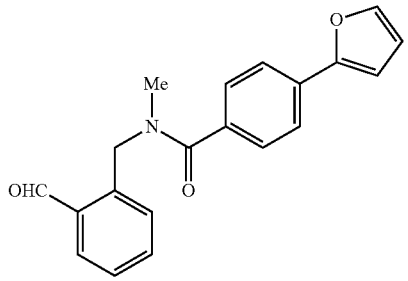 [SMILES: CN(Cc1ccccc1C=O)C(=O)c1ccc(-c2ccco2)cc1]

In a 100 mL round bottom flask, a solution of 4-(furan-2-yl)-N-(2-(hydroxymethyl)benzyl)-N-methylbenzamide (0.7 g, 2.18 mmol) in DCM (20 mL) was treated with MnO₂ (7.5 g, 43.61 mmol) at RT. The resulting reaction mixture was stirred at RT for 12 h. Upon completion of reaction (TLC), the reaction mixture was filtered through a Celite® pad. The filtrate was concentrated under reduced pressure to get the title compound. Yield: 0.6 g (86.3%).

LCMS (ESI+, m/z): 320.1 (M+H)⁺.

Step-6: Synthesis of ethyl (E)-7-(2-((4-(furan-2-yl)-N-methylbenzamido)methyl) phenyl)hept-6-enoate (Compound 8l-vi)

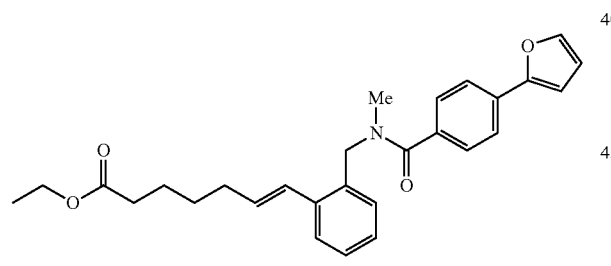

In a 250 mL round bottom flask, a solution of (6-ethoxy-6-oxohexyl)triphenylphosphonium bromide (0.6 g, 1.23 mmol) in THF (10 mL) was treated with K₂CO₃ (0.256 g, 1.85 mmol) and 18-crown-6 (0.06 g, 0.22 mmol) at 0° C. under nitrogen atmosphere. After stirring the mixture for 10 min, a solution of N-(2-formylbenzyl)-4-(furan-2-yl)-N-methylbenzamide (0.395 g, 1.23 mmol) in THF (5 mL) was added to the above mixture under nitrogen atmosphere. The reaction mixture was stirred at 60° C. for 12 h. Upon completion of reaction (TLC), the reaction mixture was diluted with ethyl acetate (100 mL) and extracted with water (100 mL). The organic extract was washed with brine, dried over anhydrous Na₂SO₄ and concentrated under reduced pressure. The residue obtained was purified by silica gel column chromatography (elution, 28% EtOAc in hexanes) to yield the title compound. Yield: 0.21 g (36.1%).

LCMS (ESI+, m/z): 446.3 (M+H)⁺.

Step-7: Synthesis of (E)-7-(2-((4-(furan-2-yl)-N-methylbenzamido)methyl)phenyl)hept-6-enoic acid (Compound 8l)

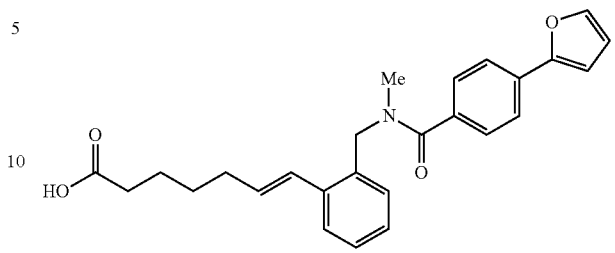

The title compound was synthesized from ethyl (E)-7-(2-((4-(furan-2-yl)-N-methylbenzamido)methyl)phenyl)hept-6-enoate (0.2 g, 0.44 mmol) following the experimental procedure described in step-4 of Example 8CC. The compound was purified by preparative HPLC [Gemini NX C 18 (21.2×150 mm particle size 5 μm); Flow: 15 mL/min; mobile phase: A/B=0.01% TFA in water/MeCN; T/% B=0/50, 2/50/8/70] to yield the title compound. Yield: 0.055 g (58.1%).

¹H NMR (400 MHz, DMSO-d₆, 60° C.): δ 11.79 (brs, 1H), 7.75 (s, 1H), 7.73 (d, J=8.4 Hz, 2H), 7.46 (d, J=8.4 Hz, 2H), 7.31-7.27 (m, 3H), 7.18 (brs, 1H), 6.99-6.98 (m, 1H), 6.61-6.59 (m, 1H), 6.45 (brs, 1H), 5.73 (brs, 1H), 4.58 (brs, 2H), 2.84 (s, 3H), 2.10-2.03 (m, 4H), 1.44-1.29 (m, 4H).

LCMS (ESI+, m/z): 418.2 (M+H)⁺ and 440.2 (M+Na)⁺.

HPLC: 96.31% (210 nm).

Example 8M

Synthesis of 2-(4-((2-((4-(furan-2-yl)-N-methylbenzamido)methyl)phenoxy) methyl)phenyl)acetic acid (Compound 8m)

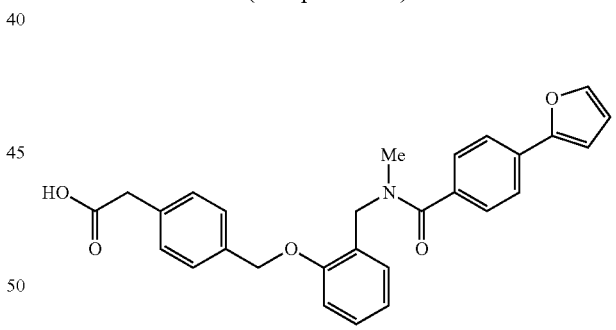

Synthetic Scheme-1:

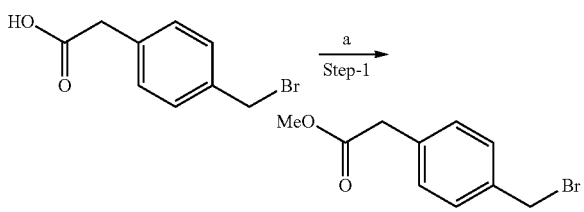

Reagents and Conditions: a) TMSCl, MeOH, RT, 1 h.

Synthetic Scheme-2:

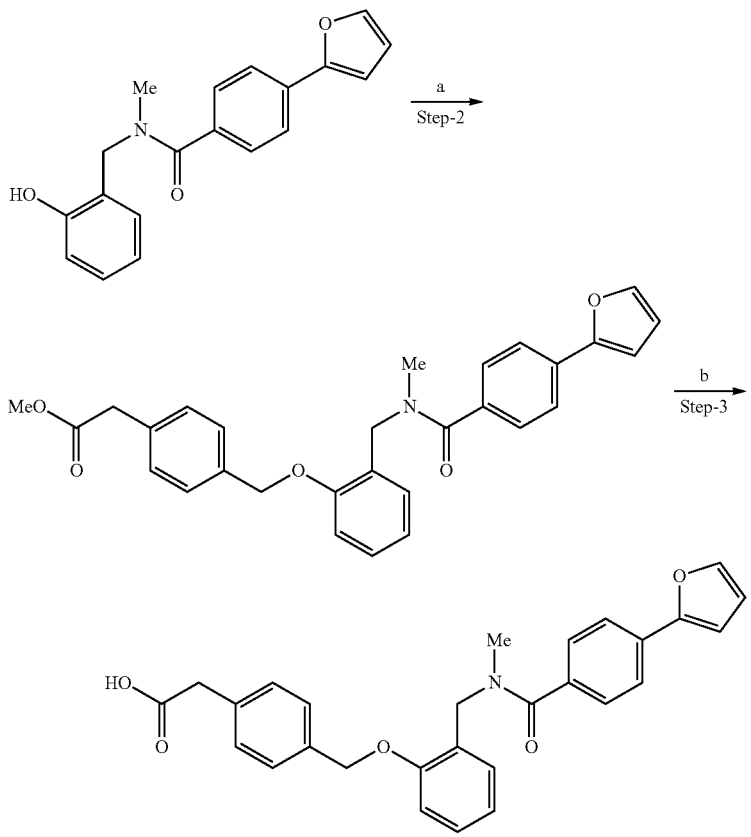

Reagents and Conditions: a) Methyl 2-(4-(bromomethyl)phenyl)acetate, K₂CO₃, DMF, 80° C., 12 h; b) LiOH•H₂O, THF, MeOH, H₂O, RT, 4 h.

Step-1. Synthesis of methyl 2-(4-(bromomethyl)phenyl)acetate (Compound 8m-i)

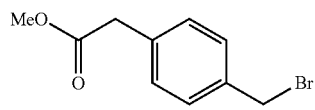 [SMILES: COC(=O)Cc1ccc(CBr)cc1]

In a 100 mL round bottom flask, a solution of 2-(4-(bromomethyl)phenyl)acetic acid (2.5 g, 10.91 mmol) in MeOH (50 mL) was treated with TMSCl (0.2 mL) under nitrogen atmosphere. The reaction mixture was stirred for 1 h at RT. Upon completion of reaction (TLC), the solvent was removed under reduced pressure. The residue obtained was dissolved in methanol and concentrated under reduced pressure to give the title compound. Yield: 2.5 g (94.3%).

$^1$H NMR (300 MHz, CDCl$_3$): δ 7.36 (d, J=8.1 Hz, 2H), 7.26 (d, J=8.4 Hz, 2H), 4.48 (s, 2H), 3.69 (s, 3H), 3.62 (s, 2H).

Step-2: Synthesis of methyl 2-(4-((2-((4-(furan-2-yl)-N-methylbenzamido)methyl) phenoxy)methyl)phenyl)acetate (Compound 8m-ii)

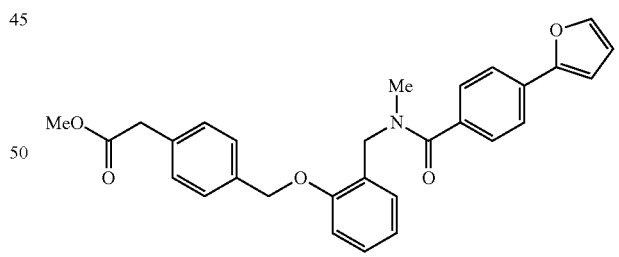

The title compound was synthesized from 4-(furan-2-yl)-N-(2-hydroxybenzyl)-N-methylbenzamide (1.0 g, 3.25 mmol) and methyl 2-(4-(bromomethyl)phenyl)acetate (0.95 g, 3.90 mmol) following the experimental procedure described in step-9 of Example 8A. Yield: 0.35 g (22.8% yield).

LCMS (ESI+, m/z): 470.1 (M+H)$^+$ and 492.3 (M+Na)$^+$.

Step-3: Synthesis of 2-(4-((2-((4-(furan-2-yl)-N-methylbenzamido)methyl)phenoxy) methyl)phenyl) acetic acid (Compound 8m)

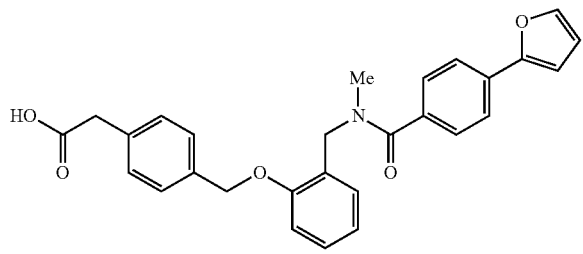 [SMILES: CN(Cc1ccccc1OCc1ccc(CC(=O)O)cc1)C(=O)c1ccc(-c2ccco2)cc1]

A stirred solution of methyl 2-(4-((2-((4-(furan-2-yl)-N-methylbenzamido)methyl) phenoxy)methyl)phenyl)acetate (0.35 g, 0.74 mmol) in THF (10 mL), MeOH (8 mL) and water (5 mL), was treated with lithium hydroxide monohydrate (0.313 g, 7.46 mmol) at RT. The mixture was stirred at RT for 4 h. Upon completion of reaction (TLC), the reaction mixture was concentrated under reduced pressure. The residue obtained was washed with EtOAc, diluted with cold water and acidified with 2 N HCl. The aqueous layer was extracted with EtOAc (3×25 mL). The combined organic extract was washed with brine and dried over anhydrous $Na_2SO_4$. The solution was concentrated under reduced pressure to give the title compound. Yield: 0.201 g (59.8%).

$^1$H NMR (400 MHz, DMSO-$d_6$, 90° C.): δ 7.72 (s, 1H), 7.70 (d, J=7.6 Hz, 2H), 7.43 (d, J=8.0 Hz, 2H), 7.34 (d, J=7.2 Hz, 2H), 7.27-7.22 (m, 4H), 7.09 (d, J=8.0 Hz, 1H), 7.0-6.92 (m, 1H), 6.95 (d, J=3.2 Hz, 1H), 6.60 (brs, 1H), 5.11 (s, 2H), 4.63 (s, 2H), 3.56 (s, 2H), 2.89 (s, 3H).

LCMS (ESI+, m/z): 456.0 (M+H)$^+$ and 478.1 (M+Na)$^+$.

HPLC: 96.87% (210 nm).

Example 8N

Synthesis of (E)-6-(2-((4-(furan-2-yl)-N-methylbenzamido)methyl)-4-methylphenoxy)-4-methylhex-4-enoic acid (Compound 8n)

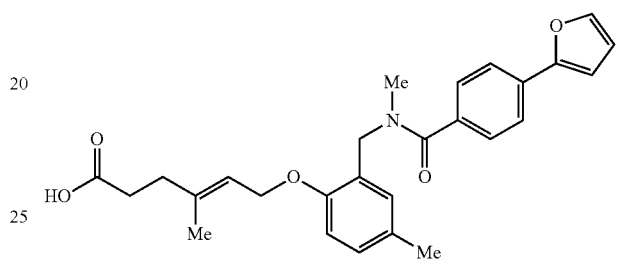

Synthetic Scheme:

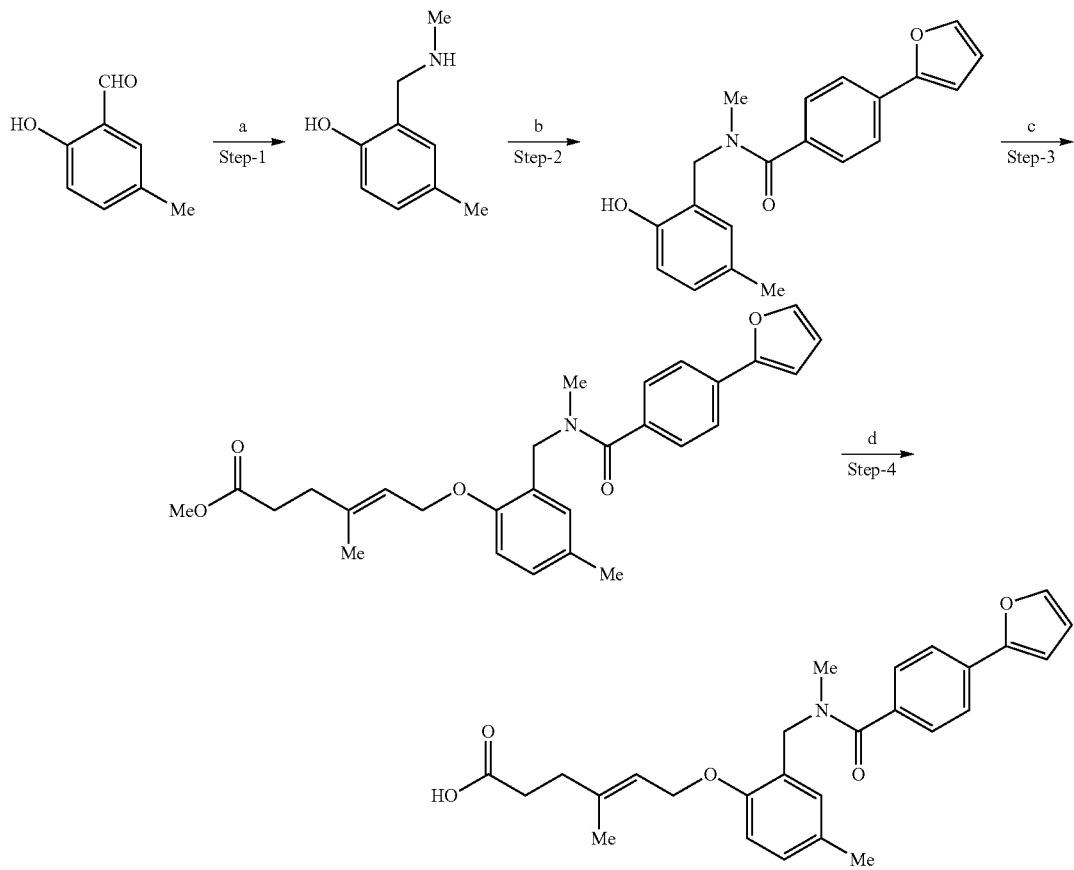

Reagents and Conditions: a) MeNH$_2$•HCl, Et$_3$N, NaBH$_4$, MeOH, RT; b) 4-(Furan-2-yl)benzoic acid, EDCI•HCl, HOBt, Et$_3$N, DMF, RT; c) Methyl (E)-6-bromo-4-methylhex-4-enoate, K$_2$CO$_3$, DMF, RT; d) LiOH•H$_2$O, THF, EtOH, H$_2$O, RT.

Step-1: Synthesis of 4-methyl-2-((methylamino)methyl)phenol (Compound 8n-i)

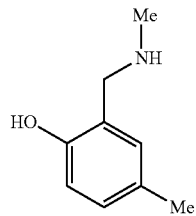

The title compound was synthesized from 2-hydroxy-5-methylbenzaldehyde (1.0 g, 7.35 mmol) following the experimental procedure described in step-6 of Example 8A. Yield: 1.03 g (81.3%).

LCMS (ESI+, m/z): 152.2 (M+H)$^+$.

Step 2: Synthesis of 4-(furan-2-yl)-N-(2-hydroxy-5-methylbenzyl)-N-methylbenzamide (Compound 8n-ii)

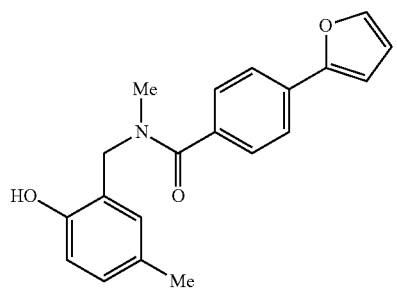 [SMILES: Cc1ccc(O)c(CN(C)C(=O)c2ccc(-c3ccco3)cc2)c1]

The title compound was synthesized from 2-((methylamino)methyl)phenol (1.0 g, 6.61 mmol) and 4-(furan-2-yl)benzoic acid (1.24 g, 6.61 mmol) following the experimental procedure described in step-8 of Example 8A. Yield: 1.48 g (crude).

LCMS (ESI+, m/z): 322.2 (M+H)$^+$.

Step-3: Synthesis of methyl (E)-6-(2-((4-(furan-2-yl)-N-methylbenzamido)methyl)-4-methylphenoxy)-4-methylhex-4-enoate (Compound 8n-iii)

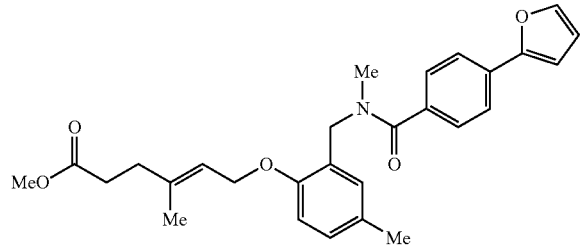 [SMILES: COC(=O)CC/C(C)=C/COc1ccc(C)cc1CN(C)C(=O)c1ccc(-c2ccco2)cc1]

The title compound was synthesized from 4-(furan-2-yl)-N-(2-hydroxy-5-methylbenzyl)-N-methylbenzamide (0.4 g, 1.24 mmol) and methyl (E)-6-bromo-4-methylhex-4-enoate (0.826 g, 3.73 mmol) following the experimental procedure described in step-9 of Example 8A. Yield: 0.357 g (crude).

LCMS (ESI+, m/z): 462.4 (M+H)$^+$ and 484.4 (M+Na)$^+$.

Step 4: Synthesis of (E)-6-(2-((4-(furan-2-yl)-N-methylbenzamido)methyl)-4-methylphenoxy)-4-methylhex-4-enoic acid (Compound 8n)

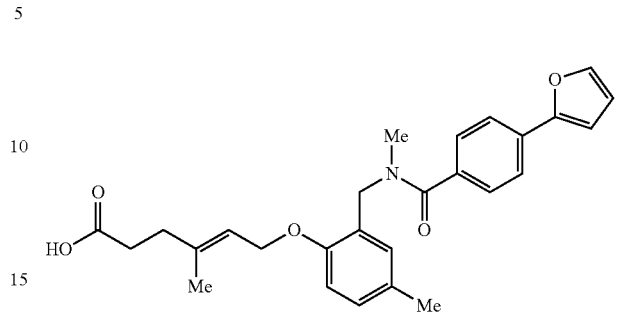

The title compound was synthesized from methyl (E)-methyl 6-(2-((4-(furan-2-yl)-N-methylbenzamido)methyl)-4-methylphenoxy)-4-methylhex-4-enoate (0.35 g, 0.76 mmol) following the experimental procedure described in step-10 of Example 8A. Yield: 0.098 g (28.0%).

$^1$H NMR (400 MHz, DMSO-d$_6$, 90° C.): δ 7.72-7.70 (m, 3H), 7.44 (d, J=8.4 Hz, 2H), 7.03 (d, J=8.0 Hz, 1H), 6.96-6.93 (m, 2H), 6.88 (d, J=8.4 Hz, 1H), 6.58-6.57 (m, 1H), 5.45 (brs, 1H), 4.52 (brs, 4H), 2.87 (s, 3H), 2.25 (s, 3H), 2.32-2.25 (m, 4H), 1.66 (s, 3H).

LCMS (API+, m/z): 448.4 (M+H)$^+$ and 470.1 (M+Na)$^+$.

HPLC: 94.50% (210 nm).

Example 8O

Synthesis of 6-(2-((4-(furan-2-yl)-N-methylbenzamido)methyl)phenoxy)-2-methylhexanoic acid (Compound 8o)

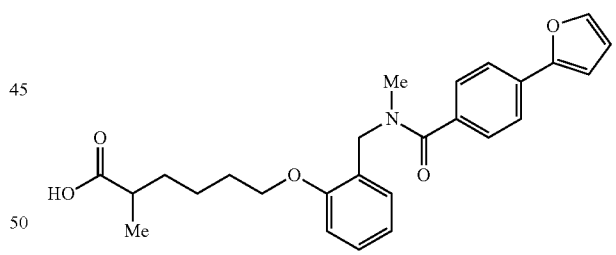

Synthetic Scheme-1:

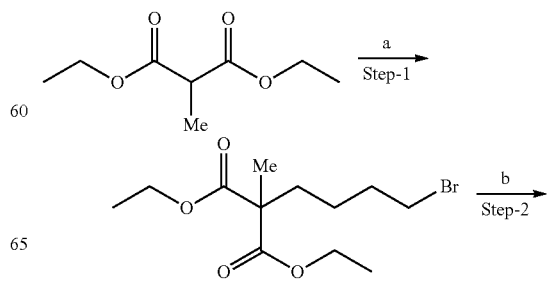

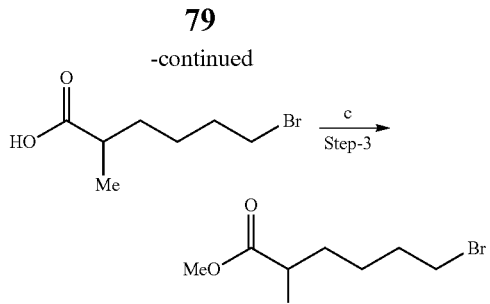

Reagents and Conditions: a) 1,4-Dibromobutane, NaH, THF, RT, 16 h; b) HBr (48% in H₂O), 110° C., 32 h; c) TMSCl, MeOH, RT, 24 h.

reaction mixture was stirred for 15 min at RT and treated with, 1,4-dibromobutane (13.6 g, 63.79 mmol) under nitrogen atmosphere.

The reaction mixture was stirred for 16 h at RT. Upon completion of reaction (TLC), the reaction mixture was quenched with 1 N NaOH (20 mL) and extracted with EtOAc (3×50 mL). The combined organic extract was washed with brine and dried over anhydrous Na₂SO₄. The solvent was removed under reduced pressure. The residue obtained was purified by silica gel column chromatography (gradient elutions, 0-10% EtOAc in hexanes) to get the title compound. Yield: 2.61 g (49.1%).

Synthetic Scheme-2:

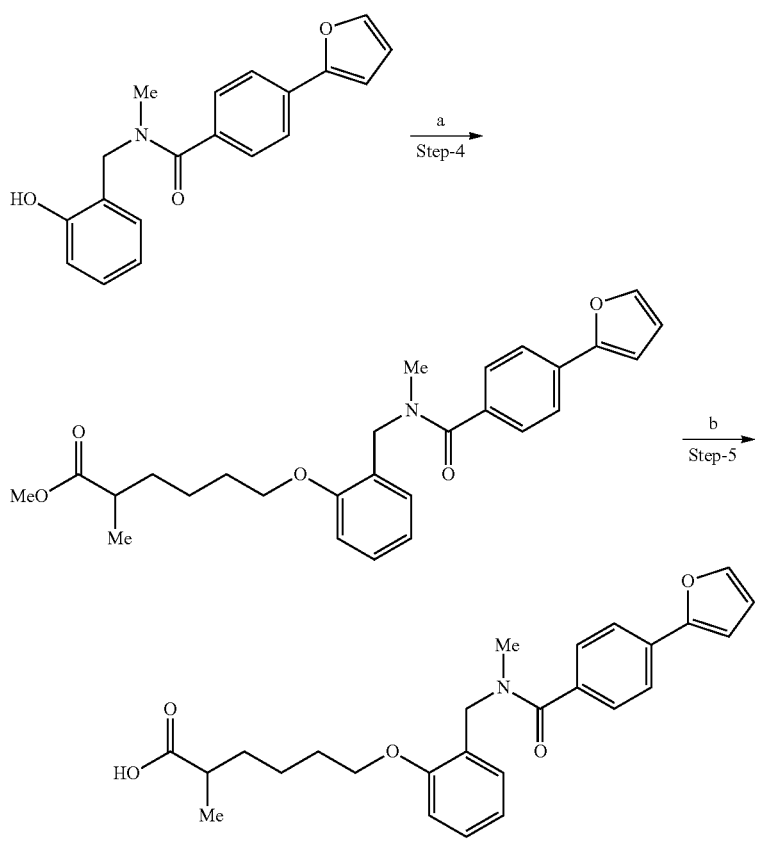

Reagents and Conditions: a) Methyl 6-bromo-2-methylhexanoate, K₂CO₃, DMF, 60° C.; c) LiOH·H₂O, THF, EtOH, H₂O, RT

Step-1: Synthesis of diethyl 2-(4-bromobutyl)-2-methylmalonate (Compound 8o-i)

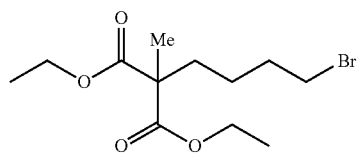 [SMILES: CCOC(=O)C(C)(CCCCBr)C(=O)OCC]

In a 100 mL round bottom flask, a suspension of NaH (60% dispersion, 0.690 g, 17.25 mmol) in anhydrous THF (15 mL) was treated with a solution of diethyl 2-methylmalonate (3.0 g, 17.24 mmol) dropwise at 0° C. The resulting $^1$H NMR (300 MHz, CDCl₃): δ 4.09 (q, J=6.9 Hz, 4H), 3.51 (t, J=6.6 Hz, 2H), 1.79-1.72 (m, 4H), 1.31-1.25 (m, 2H), 1.29 (s, 3H), 1.14 (t, J=7.2 Hz, 6H)

Step 2: Synthesis of 6-bromo-2-methylhexanoic acid (Compound 8o-ii)

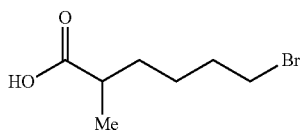

In a 100 mL round bottom flask, a solution of diethyl 2-(4-bromobutyl)-2-methylmalonate (2.5 g, 8.11 mmol) was treated with 48% HBr in H$_2$O (25 mL) at RT. The resulting reaction mixture was stirred at 110° C. for 7 h, later at RT for 15 h and again stirred at 110° C. for 9 h. Upon completion of reaction (TLC), the reaction mixture was washed with 15% NaOH and extracted with 5% MeOH in CHCl$_3$ (3×100 mL). The organic extracts were washed with brine, dried over anhydrous Na$_2$SO$_4$ and solvent was removed under reduced pressure to afford the title compound (1.6 g, crude) which was used in the next step without further purification.

Step 3: Synthesis of methyl 6-bromo-2-methylhexanoate (Compound 8o-iii)

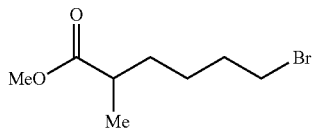 [SMILES: COC(=O)C(C)CCCCBr]

In a 50 mL round bottom flask, a stirred solution of hept-6-ynoic acid (1.5 g, 11.90 mmol) in MeOH (30 mL) was treated with TMSCl (0.5 mL, catalytic amount) at RT under nitrogen atmosphere. The reaction mixture was stirred at 60° C. for 12 h under nitrogen atmosphere. Upon completion of reaction (TLC), the reaction mixture was concentrated under reduced pressure, diluted with ice cold water and extracted with EtOAc (3×20 mL). The organic extract was washed with brine and dried over anhydrous Na$_2$SO$_4$. The solution was concentrated under reduced pressure to yield the title compound. Yield: 1.2 g.

$^1$H NMR (300 MHz, CDCl$_3$): δ 3.67 (s, 3H), 3.39 (t, J=6.6 Hz, 2H), 2.47-2.42 (m, 1H), 1.91-1.83 (m, 2H), 1.70-1.52 (m, 2H), 1.47-1.40 (m, 2H), 1.15 (d, J=7.2 Hz, 3H).

Step-4: Synthesis of methyl 6-(2-((4-(furan-2-yl)-N-methylbenzamido)methyl)phenoxy)-2-methylhexanoate (Compound 8o-iv)

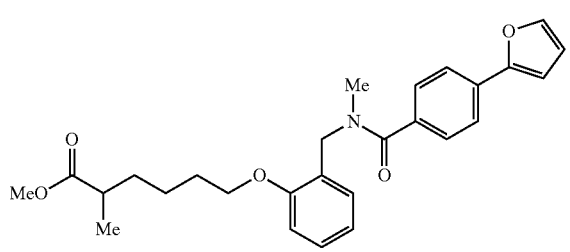 [SMILES: COC(=O)C(C)CCCCOc1ccccc1CN(C)C(=O)c1ccc(-c2ccco2)cc1]

The title compound was synthesized from 4-(furan-2-yl)-N-(2-hydroxybenzyl)-N-methylbenzamide (0.4 g, 1.30 mmol) and methyl 6-bromo-2-methylhexanoate (0.37 g, 1.56 mmol) following the experimental procedure described in step-9 of Example 8A. Yield: 0.33 g (56.0%).

LCMS (ESI+, m/z): 450.3 (M+H)$^+$ and 472.4 (M+Na)$^+$.

Step-5: Synthesis of 6-(2-((4-(furan-2-yl)-N-methylbenzamido)methyl)phenoxy)-2-methylhexanoic acid (Compound 8o)

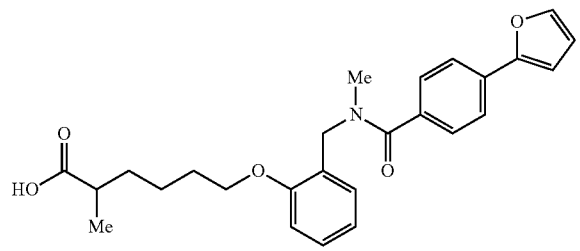 [SMILES: CC(CCCCOc1ccccc1CN(C)C(=O)c1ccc(-c2ccco2)cc1)C(=O)O]

The title compound was synthesized from methyl 6-(2-((4-(furan-2-yl)-N-methylbenzamido)methyl)phenoxy)-2-methylhexanoate (0.3 g, 0.66 mmol) following the experimental procedure described in step-10 of Example 8A. Yield: 0.188 g (64.8%).

$^1$H NMR (400 MHz, DMSO-d$_6$, 90° C.): δ 11.70 (brs, 1H), 7.73-7.71 (m, 3H), 7.47 (d, J=8.4 Hz, 2H), 7.25-7.19 (m, 2H), 7.0-6.94 (m, 3H), 6.60-6.58 (m, 1H), 4.59 (s, 2H), 3.94 (t, J=6.4 Hz, 2H), 2.91 (s, 3H), 2.33-2.31 (m, 1H), 1.72-1.69 (m, 3H), 1.41 (brs, 3H), 1.06 (d, J=6.8 Hz, 3H).

LCMS (ESI+, m/z): 436.2 (M+H)$^+$ and 458.1 (M+Na)$^+$.

HPLC: 95.0% (210 nm).

Example 8P

Synthesis of 3-(3-((2-((4-(furan-2-yl)-N-methylbenzamido)methyl)phenoxy) methyl)phenyl)propanoic acid (Compound 8p)

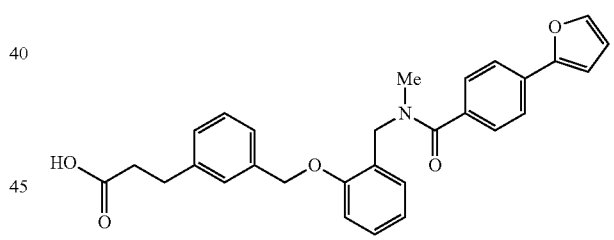

Synthetic Scheme-1:

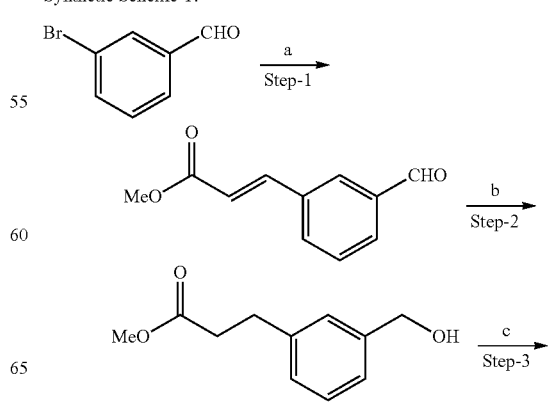

-continued

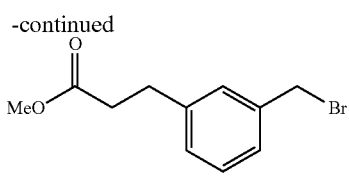

Reagents and conditions: a) Methyl acrylate, Pd(OAc)$_2$, PPh$_3$, Et$_3$N, DMF, 100° C.; b) NaBH$_4$, NiCl$_2$•6H$_2$O, MeOH, RT, 3 h; c) CBr$_4$, PPh$_3$, THF, RT, 3 h.

g, 14.05 mmol) under nitrogen atmosphere. The reaction mixture was stirred for 12 h at 100° C. Upon completion of reaction (TLC), the reaction mixture was poured into ice cold water and extracted with EtOAc (2×100 mL). The combined organic extract was dried over anhydrous Na$_2$SO$_4$. The solvent was removed under reduced pressure to get the crude residue. The residue obtained was purified by silica gel column chromatography (elution, 20% EtOAc in hexanes) to afford the title compound. Yield: 2.01 g (87.0%).

Synthetic Scheme-2:

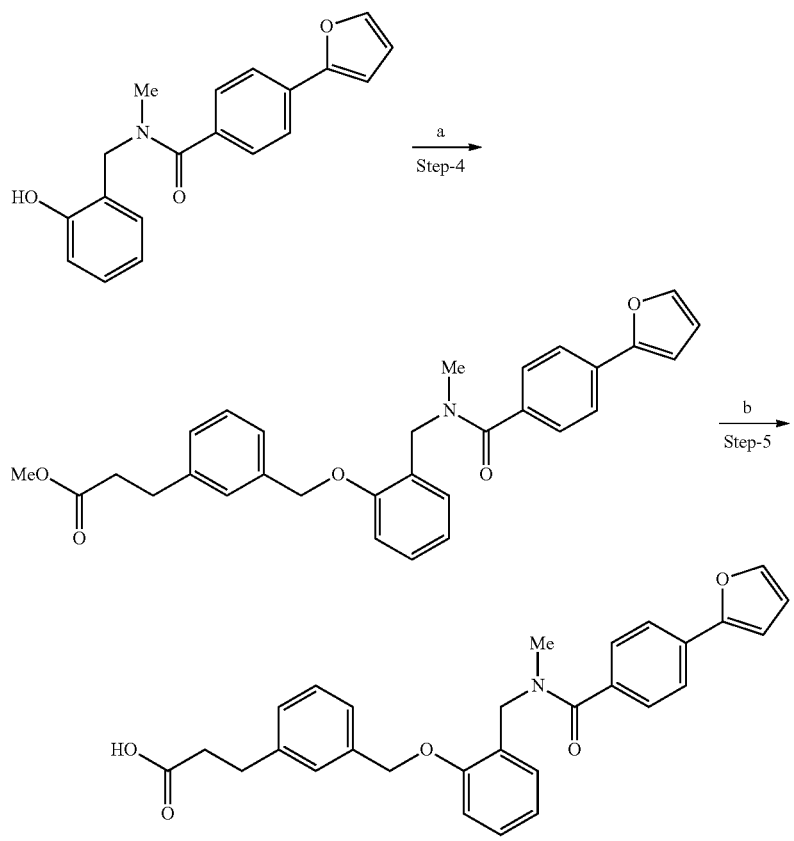

Reagents and conditions:
a) Methyl 3-(3-(bromomethyl)phenyl)propanoate, K$_2$CO$_3$, DMF, 80° C., 3 h;
b) LiOH•H$_2$O, THF, EtOH, H$_2$O, RT, 12 h.

Step-1: Synthesis of methyl (E)-3-(3-formylphenyl)acrylate (Compound 8p-i)

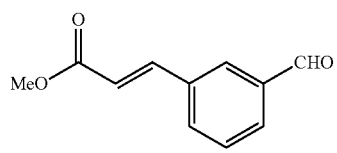 [SMILES: COC(=O)/C=C/c1cccc(C=O)c1]

In a 100 mL resealable reaction tube, a degassed solution of 3-bromobenzaldehyde (2.0 g, 10.81 mmoL) in DMF (20 mL) was treated with Pd(OAc)$_2$ (0.121 g, 0.54 mmol), PPh$_3$ (0.565 g, 2.16 mmol) and Et$_3$N (2.19 mL, 16.21 mmol) at RT under nitrogen atmosphere. The resulting reaction mixture was stirred for 10 min and treated with methyl acrylate (1.2

$^1$H NMR (300 MHz, DMSO-d$_6$): δ 10.02 (s, 1H), 8.24 (s, 1H), 8.05 (d, J=6.0 Hz, 1H), 7.92 (d, J=7.5 Hz, 1H), 7.74 (d, J=15.9 Hz, 1H), 7.66-7.61 (m, 1H), 6.76 (d, J=16.2 Hz, 1H), 3.72 (s, 3H).

Step-2: Synthesis of methyl 3-(3-(hydroxymethyl)phenyl)propanoate (Compound 8p-ii)

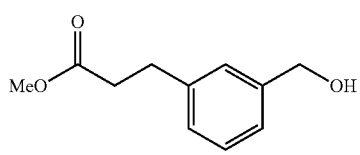 [SMILES: COC(=O)CCc1cccc(CO)c1]

In a 100 mL round bottom flask, a solution of methyl (E)-3-(3-formylphenyl)acrylate (1.0 g, 5.25 mmol) in MeOH (50 mL) was treated with NiCl$_2$.6H$_2$O (1.24 g, 5.25 mmol) and NaBH$_4$ (0.596 g, 15.77 mmol) at RT. The reaction mixture was stirred for 3 h at RT. Upon completion of reaction (TLC), the reaction mixture was quenched with ice cold water and extracted with EtOAc (2×100 mL). The organic extract was separated and dried over anhydrous Na$_2$SO$_4$. The organic solvent was removed under reduced pressure to get the residue. The residue obtained was purified by column chromatography (elution, 30% EtOAc in hexanes) to afford the title compound. Yield: 1.0 g (99.0%).

$^1$H NMR (300 MHz, CDCl$_3$): δ 7.31-7.08 (m, 4H), 4.95 (brs, 1H), 4.67 (s, 2H), 3.67 (s, 3H), 2.95 (t, J=8.0 Hz, 2H), 2.63 (t, J=7.6 Hz, 2H),

Step-3: Synthesis of methyl 3-(3-(bromomethyl)phenyl)propanoate (Compound 8p-iii)

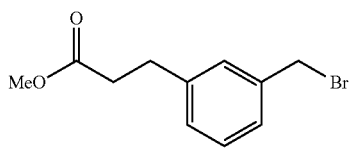 [SMILES: COC(=O)CCc1cccc(CBr)c1]

The title compound was synthesized from methyl 3-(3-(hydroxymethyl)phenyl)propanoate (0.2 g, 1.02 mmol) and CBr$_4$ (0.682 g, 2.06 mmol) following the experimental procedure described in step-5 of Example 8A. Yield: 0.111 g (43.0%).

$^1$H NMR (400 MHz, CDCl$_3$): δ 7.27-7.23 (m, 3H), 7.14 (d, J=7.2 Hz, 1H), 4.47 (s, 2H), 3.67 (s, 3H), 2.95 (t, J=8.0 Hz, 2H), 2.63 (t, J=7.6 Hz, 2H).

LCSM (ESI+, m/z): 257.1 (M+H)$^+$.

Step-4: Synthesis of methyl 3-(3-((2-((4-(furan-2-yl)-N-methylbenzamido)methyl) phenoxy)methyl) phenyl)propanoate (Compound 8p-iv)

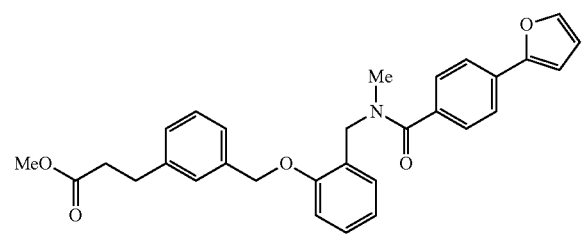 [SMILES: COC(=O)CCc1cccc(COc2ccccc2CN(C)C(=O)c2ccc(-c3ccco3)cc2)c1]

The title compound was synthesized from 4-(furan-2-yl)-N-(2-hydroxybenzyl)-N-methylbenzamide (0.5 g, 1.62 mmol) and methyl 3-(3-(bromomethyl)phenyl)propanoate (0.46 g, 4.86 mmol) following the experimental procedure described in step-9 of Example 8A. Yield: 0.513 g (65.0%).

LCMS (ESI+, m/z): 484.2 (M+H)$^+$ and 506.2 (M+Na)$^+$.

Step-5: Synthesis of 3-(3-((2-((4-(furan-2-yl)-N-methylbenzamido)methyl)phenoxy) methyl)phenyl) propanoic acid (Compound 8p)

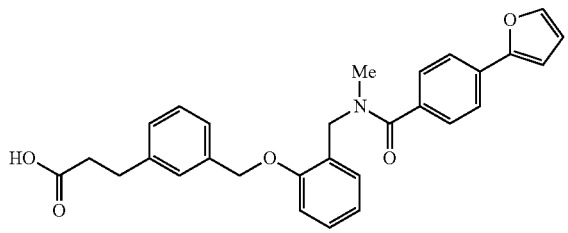

The title compound was synthesized methyl 3-(3-((2-((4-(furan-2-yl)-N-methylbenzamido)methyl)phenoxy)methyl) phenyl)propanoate (0.4 g, 0.83 mmol) following the experimental procedure described in step-10 of Example 8A. Yield: 0.35 g (90.0%).

$^1$H NMR (300 MHz, DMSO-d6, 60° C.): δ 11.95 (brs, 1H), 7.73-7.62 (m, 3H), 7.41 (d, J=8.1 Hz, 2H), 7.27-7.13 (m, 6H), 7.07 (d, J=7.8 Hz, 1H), 6.99-6.95 (m, 2H), 6.58-6.57 (m, 1H), 5.07 (brs, 2H), 4.59 (brs, 2H), 2.87 (s, 3H), 2.81 (t, J=7.5 Hz, 2H), 2.49 (t, J=7.5 Hz, 2H).

LCMS (ESI+, m/z): 470.0 (M+H)$^+$.

HPLC: 95.33% (210 nm).

Example 8Q

Synthesis of 2-(3-((2-((4-(furan-2-yl)-N-methylbenzamido)methyl)phenoxy) methyl) phenyl)acetic acid (Compound 8q)

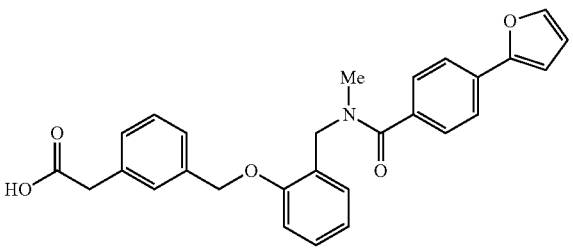 [SMILES: CN(Cc1ccccc1OCc1cccc(CC(=O)O)c1)C(=O)c1ccc(-c2ccco2)cc1]

Synthetic Scheme-1:

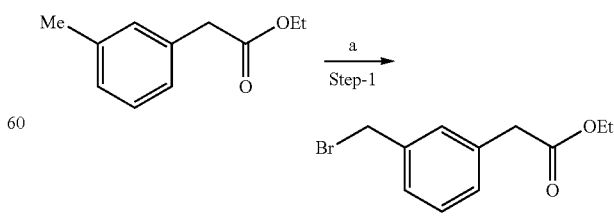

Reagents and conditions:
a) NBS, benzoylperoxide, CCl$_4$, 80° C., 12 h.

Synthetic Scheme-2:

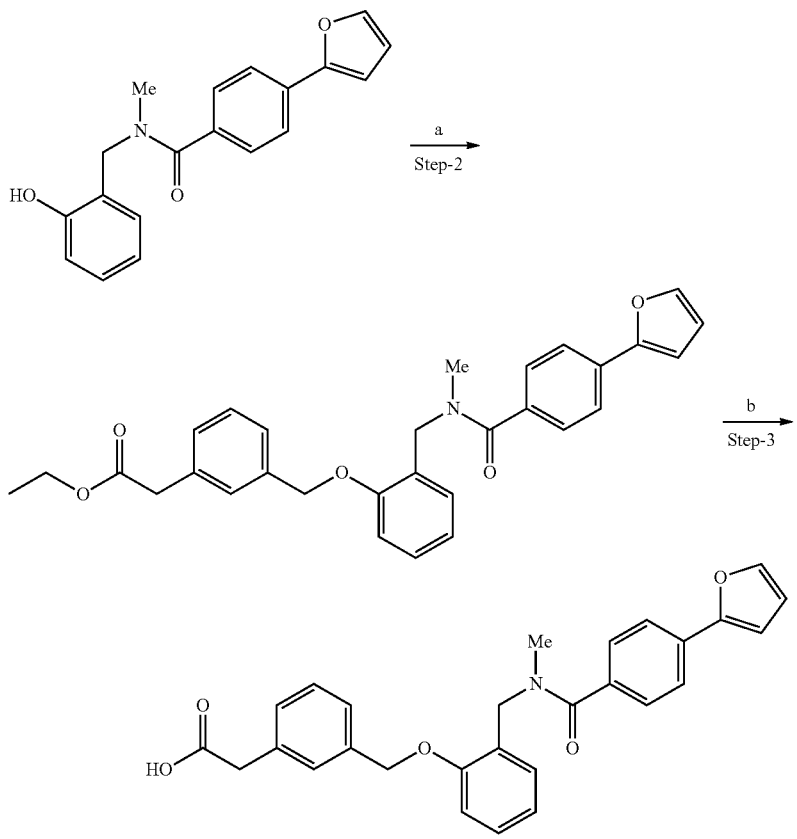

Reagents and conditions:
a) Ethyl 2-(3-(bromomethyl)phenyl)acetate, $K_2CO_3$, DMF, 80° C., 3 h;
b) LiOH·$H_2O$, THF, EtOH, $H_2O$, RT, 12 h.

Step-1: Synthesis of ethyl 2-(3-(bromomethyl)phenyl)acetate (Compound 8q-i)

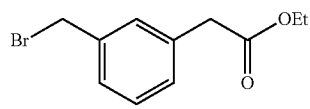 [SMILES: CCOC(=O)Cc1cccc(CBr)c1]

In a 100 mL round bottom flask, a solution of ethyl 2-(m-tolyl)acetate (2.0 g, 11.23 mmol) in $CCl_4$ (12 mL) was treated with N-bromosuccinimide (2.16 g, 12.35 mmol) and catalytic benzoyl peroxide (0.003 g) under nitrogen atmosphere. The resulting reaction mixture was stirred for 12 h at 80° C. Upon completion of reaction (TLC), the reaction mixture was quenched with ice cold water and extracted with EtOAc (2×100 mL). The organic extract was separated and dried over anhydrous $Na_2SO_4$. The solvent was removed under reduced pressure to get the crude residue. The residue obtained was purified by silica gel column chromatography (gradient elutions, 5-10% EtOAc in hexanes) to afford the title compound. Yield: 1.1 g (40.2%).

$^1$H NMR (300 MHz, $CDCl_3$): δ 7.32-7.25 (m, 4H), 4.48 (s, 2H), 4.15 (q, J=6.9 Hz, 2H), 3.61 (s, 2H), 1.26 (t, J=7.5 Hz, 3H).

LCMS (ESI+, m/z): 257.0, 259.0 (M+H)$^+$.

Step-2: Synthesis of ethyl 2-(3-((2-((4-(furan-2-yl)-N-methylbenzamido)methyl)phenoxy) methyl)phenyl)acetate (Compound 8q-ii)

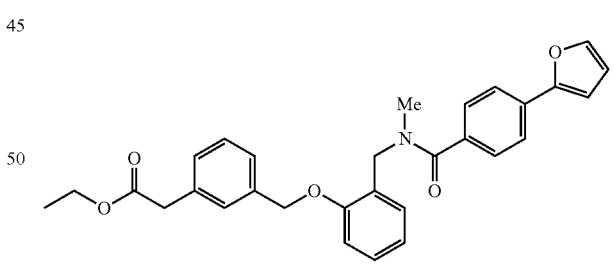

The title compound was synthesized from 4-(furan-2-yl)-N-(2-hydroxybenzyl)-N-methylbenzamide (0.5 g, 1.62 mmol) and ethyl 3-(3-(bromomethyl)phenyl)propanoate (0.46 g, 4.86 mmol) following the experimental procedure described in step-9 of example-1. Yield: 0.513 g (65.0%).

LCMS (ESI+, m/z): 484.2 (M+H)$^+$ and 506.2 (M+Na)$^+$.

Step-3: Synthesis of 2-(3-((2-((4-(furan-2-yl)-N-methylbenzamido)methyl)phenoxy) methyl)phenyl)acetic acid (Compound 8q)

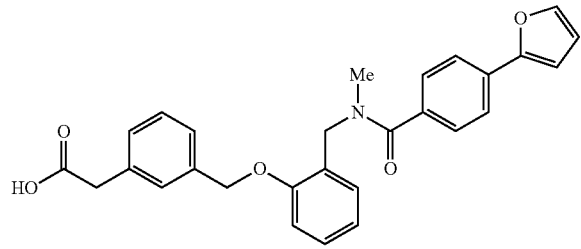 [SMILES: CN(Cc1ccccc1OCc1cccc(CC(=O)O)c1)C(=O)c1ccc(-c2ccco2)cc1]

The title compound was synthesized from ethyl 2-(3-((2-((4-(furan-2-yl)-N-methylbenzamido)methyl)phenoxy) methyl)phenyl)acetate (0.4 g, 0.92 mmol) following the experimental procedure described in step-10 of Example 8A. Yield: 0.14 g (33.4%).

$^1$H NMR (400 MHz, DMSO-d6, 90° C.): δ 12.80 (brs, 1H), 7.73 (s, 1H), 7.70 (d, J=8.0 Hz, 2H), 7.43 (d, J=8.0 Hz, 2H), 7.33-7.22 (m, 6H), 7.10 (d, J=8.0 Hz, 1H), 7.01-6.94 (m, 2H), 6.60 (brs, 1H), 5.12 (s, 2H), 4.63 (s, 2H), 3.56 (s, 2H), 2.90 (s, 3H).

LCMS (ESI+, m/z): 456.2 (M+H)$^+$ and 478.3 (M+Na)$^+$
HPLC: 96.23% (210 nm).

Example 8R

Synthesis of 2-(3-((2-((4-(furan-2-yl)-N-methylbenzamido)methyl)phenoxy) methyl) phenoxy)acetic acid (Compound 8r)

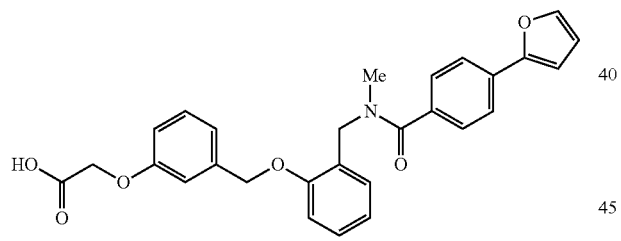

Synthetic Scheme-1:

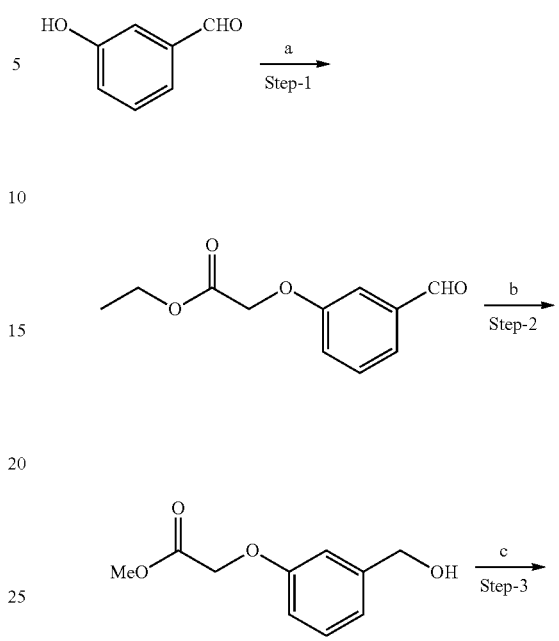

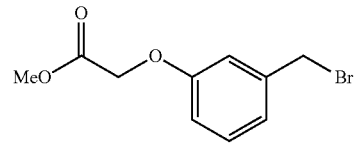

Reagents and conditions:
a) Ethyl chloroacetate, K$_2$CO$_3$, 60° C., 4 h;
b) NaBH$_4$, MeOH, RT, 1 h;
c) CBr$_4$, PPh$_3$, THF, RT, 12 h.

Synthetic Scheme-2:

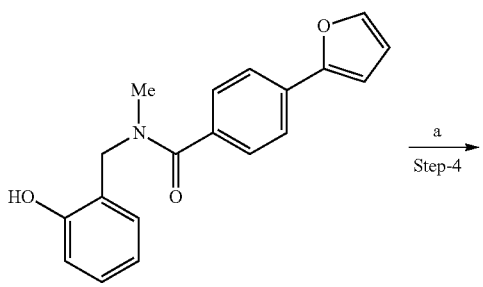

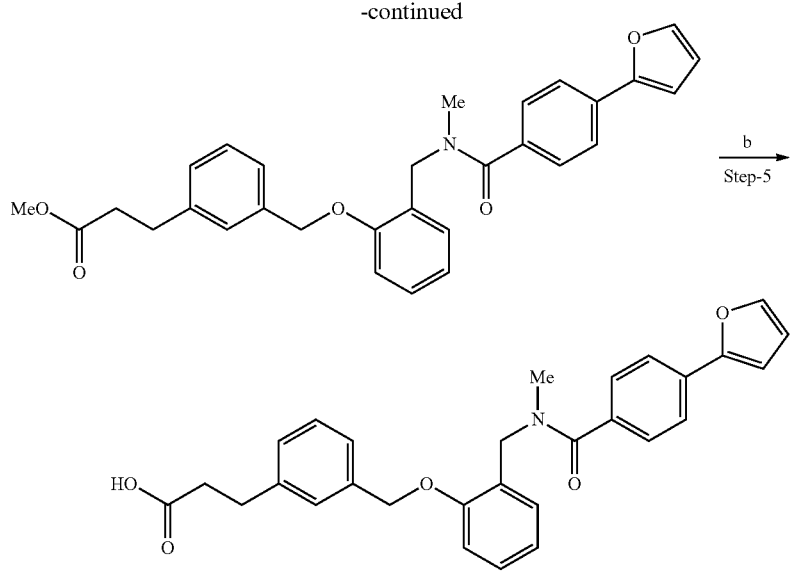

Reagents and conditions:
a) Ethyl 2-(3-(bromomethyl)phenoxy)acetate, K₂CO₃, DMF, 60° C., 4 h;
b) LiOH·H₂O, THF, EtOH, H₂O, 70° C., 2 h.

Step-1: Synthesis of ethyl 2-(3-formylphenoxy)acetate (Compound 8r-i)

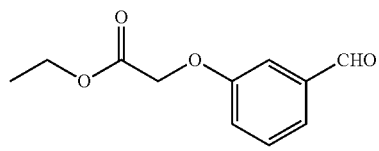

The title compound was synthesized from 3-hydroxybenzaldehyde (2.0 g, 16.39 mmol) and ethyl chloroacetate (2.00 g, 16.39 mmol) following the experimental procedure described in step-9 of example-1. Yield: 0.850 g (27.9%).

¹H NMR (400 MHz, DMSO-d₆): δ 9.95 (s, 1H), 7.53-7.52 (m, 2H), 7.39 (d, J=2.4 Hz, 1H), 7.30-7.25 (m, 1H), 4.88 (s, 2H), 4.15 (q, J=7.2 Hz, 2H), 1.19 (t, J=7.2 Hz, 3H).

LCMS (ESI+, m/z): 209.3 (M+H)⁺.

Step-2: Synthesis of methyl 2-(3-(hydroxymethyl)phenoxy)acetate (Compound 8r-ii)

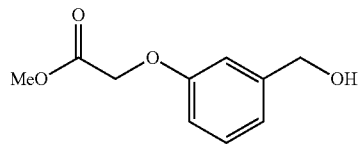 [SMILES: COC(=O)COc1cccc(CO)c1]

In a 100 mL round bottom flask, a solution of ethyl 2-(3-formylphenoxy)acetate (0.85 g, 4.08 mL) in MeOH (5 mL) was treated with NaBH₄ (0.185 g, 4.89 mmol) in portions at 0° C. The reaction mixture was stirred for 1 h at RT. Upon completion of reaction (TLC), the reaction mixture was quenched with ice cold water (10 mL) and extracted with EtOAc (2×100 mL). The combined organic extract was washed with brine, and dried over anhydrous Na₂SO₄. The solvent was removed under reduced pressure and residue obtained was purified by column silica gel (elution, 80% EtOAc in hexanes) to afford the title compound. Yield: 0.3 g (35.0%).

¹H NMR (300 MHz, DMSO-d₆): δ 7.23-7.18 (m, 1H), 6.90-6.85 (m, 2H), 6.77-6.73 (m, 1H), 5.17 (t, J=5.7 Hz, 1H), 4.75 (s, 2H), 4.43 (d, J=6.0 Hz, 2H), 3.67 (s, 3H).

Step-3: Synthesis of methyl 2-(3-(bromomethyl)phenoxy)acetate (Compound 8r-iii)

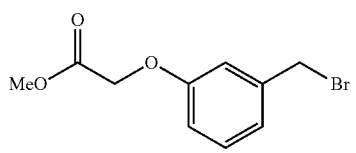 [SMILES: COC(=O)COc1cccc(CBr)c1]

The title compound was synthesized from methyl 2-(3-(hydroxymethyl)phenoxy)acetate (0.85 g, 3.79 mmol) and CBr₄ (3.8 g, 11.38 mmol) following the experimental procedure described in step-5 of Example 8A. Yield: 0.446 g (45.4%).

¹H NMR (300 MHz, DMSO-d₆): δ 7.53-7.52 (m, 2H), 7.39 (d, J=2.4 Hz, 1H), 7.30-7.25 (m, 1H), 4.78 (s, 2H), 4.64 (s, 2H), 3.68 (s, 3H).

LCMS (ESI+, m/z): 259.0, 261.0 (M+H)⁺.

Step-4: Synthesis of methyl 2-(3-((2-((4-(furan-2-yl)-N-methylbenzamido)methyl) phenoxy)methyl) phenoxy)acetate (Compound 8r-iv)

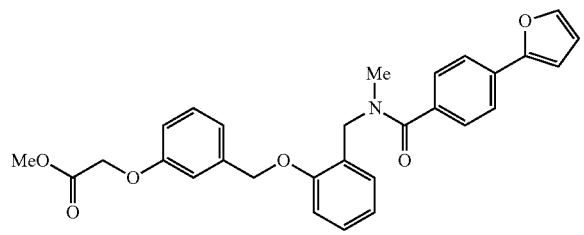

The title compound was synthesized from 4-(furan-2-yl)-N-(2-hydroxybenzyl)-N-methylbenzamide (0.5 g, 1.62 mmol) and methyl 2-(3-(bromomethyl)phenoxy)acetate (0.873 g, 3.96 mmol) following the experimental procedure described in step-9 of Example 8A. Yield: 0.310 g (50.4%).
LCMS (ESI+, m/z): 486.3 (M+H)+.

Step-5: Synthesis of 2-(3-((2-((4-(furan-2-yl)-N-methylbenzamido)methyl) phenoxy)methyl) phenoxy)acetic acid (Compound 8r)

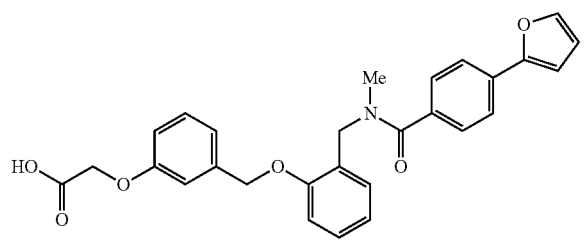 [SMILES: CN(Cc1ccccc1OCc1cccc(OCC(=O)O)c1)C(=O)c1ccc(-c2ccco2)cc1]

The title compound was synthesized from methyl 2-(3-((2-((4-(furan-2-yl)-N-methylbenzamido)methyl)phenoxy)methyl)phenoxy)acetate (0.3 g, 0.64 mmol) following the experimental procedure described in step-10 of Example 8A. Yield: 0.110 g (32.2%).

¹H NMR (400 MHz, DMSO-d₆, 60° C.): δ 7.75-7.70 (m, 3H), 7.45-7.42 (m, 2H), 7.28-7.21 (m, 3H), 7.09-7.07 (m, 1H), 7.01-6.98 (m, 4H), 6.85 (d, J=8.4 Hz, 1H), 6.60 (s, 1H), 5.10 (s, 2H), 4.62 (s, 4H), 2.90 (s, 3H),
LCMS (ESI+, m/z): 471.7 (M+H)+.
HPLC: 97.04% (210 nm).

Example 8S

Synthesis of 6-(2-((4-(furan-2-yl)-N-methylbenzamido)methyl)phenoxy)-2,2-dimethylhexanoic acid (Compound 8s)

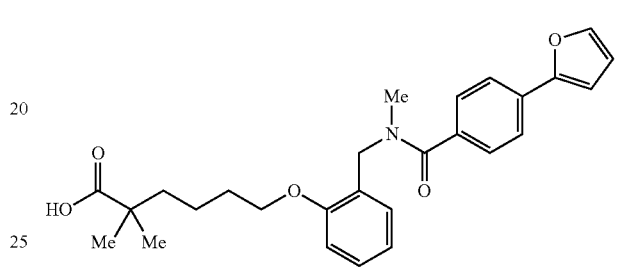

Synthetic Scheme-1:

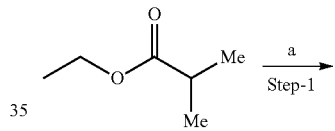

Reagents and conditions:
a) n-BuLi, diisopropyl amine, THF; 1,4-Dibromobutane, -78° C. to RT, 2 h.

Synthetic Scheme-2:

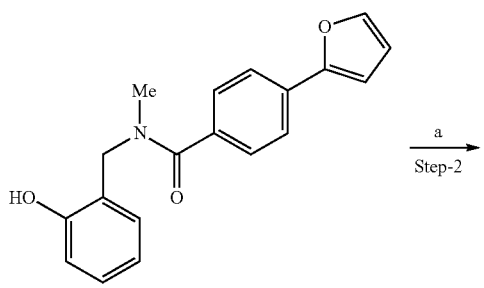

-continued

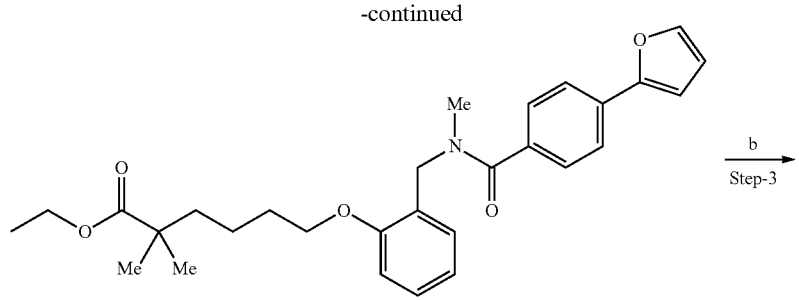

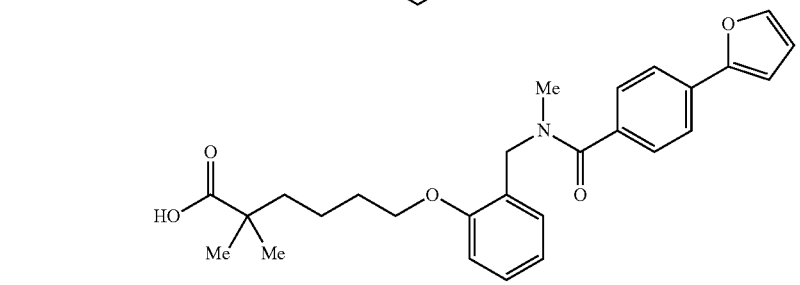

Reagents and conditions:
a) Ethyl 6-bromo-2,2-dimethylhexanoate, K₂CO₃, DMF, 70° C., 12 h;
b) LiOH·H₂O, THF, EtOH, H₂O, RT, 2 h.

Step-1: Synthesis of ethyl 6-bromo-2,2-dimethylhexanoate (Compound 8s-i)

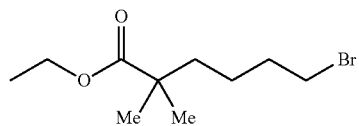

In a 100 mL round bottom flask, a solution of diisopropyl amine (1.43 mL, 14.13 mmol) in anhydrous THF was treated with 2 M solution of n-BuLi in hexane (6.8 mL, 14.3 mmol) at 0° C. under nitrogen atmosphere. The resulting reaction mixture was stirred for 30 min at 0° C. Ethyl isobutyrate (1.37 mL, 11.80 mmol) was added to the above reaction mixture at −78° C. The resulting reaction mixture was stirred for 1 h at −78° C. 1,4-Dibromobutane (1.05 mL, 9.44 mmol) was added to the reaction mixture at −78° C. The reaction mixture was stirred for 2 h at RT. Upon completion of reaction (TLC), the reaction mixture was quenched with aqueous NH₄Cl (50 mL) and extracted with EtOAc (3×50 mL). The organic extract was dried over anhydrous Na₂SO₄ and concentrated under reduced pressure. The residue obtained was purified by silica gel column chromatography (gradient elution, 0-5% EtOAc in hexanes) to get the title compound. Yield: 0.96 g (32.5%).

¹H NMR (300 MHz, CDCl₃): δ 4.12 (q, J=7.2 Hz, 2H), 3.39 (t, J=6.9 Hz, 2H), 1.91-1.78 (m, 2H), 1.55-1.50 (m, 2H), 1.42-1.33 (m, 2H), 1.25 (t, J=7.2 Hz, 3H), 1.65 (s, 6H).

Step-2: Synthesis of ethyl 6-(2-((4-(furan-2-yl)-N-methylbenzamido)methyl)phenoxy)-2,2-dimethyl-hexanoate (Compound 8s-ii)

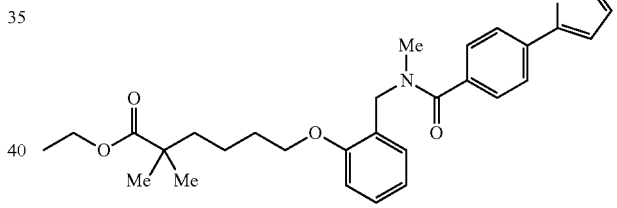

The title compound was synthesized from 4-(furan-2-yl)-N-(2-hydroxybenzyl)-N-methylbenzamide (0.5 g, 1.62 mmol) and ethyl 6-bromo-2,2-dimethylhexanoate (0.490 g, 1.95 mmol) following the experimental procedure described in step-9 of Example 8A. Yield: 0.57 g (73.4%).

LCMS (ESI+, m/z): 477.8 (M+H)⁺ and 499.7 (M+Na)⁺.

Step-3: Synthesis of 6-(2-((4-(furan-2-yl)-N-methyl-benzamido)methyl)phenoxy)-2,2-dimethylhexanoic acid (Compound 8s)

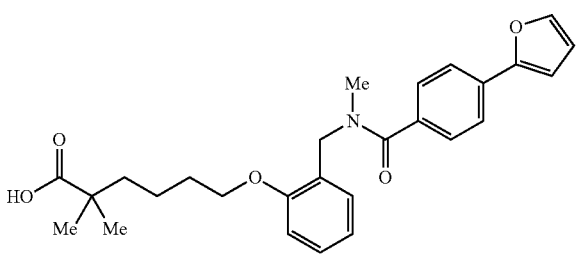 [SMILES: CN(Cc1ccccc1OCCCCC(C)(C)C(=O)O)C(=O)c1ccc(-c2ccco2)cc1]

The title compound was synthesized from ethyl 6-(2-((4-(furan-2-yl)-N-methylbenzamido)methyl)phenoxy)-2,2-dimethylhexanoate (0.5 g, 1.04 mmol) following the experimental procedure described in step-10 of Example 8A. Yield: 0.31 g, (66.0%).

¹H NMR (400 MHz, DMSO-d₆, 90° C.): δ 7.73-7.72 (m, 3H), 7.47 (d, J=8.0 Hz, 2H), 7.26-7.19 (m, 2H), 7.07-6.96 (m, 3H), 6.60 (s, 1H), 4.59 (s, 2H), 3.99 (t, J=6.0 Hz, 2H), 2.91 (s, 3H), 1.68-1.67 (m, 2H), 1.58-1.49 (m, 2H), 1.37 (brs, 2H), 1.08 (s, 6H).

LCMS (ESI+, m/z): 449.8 (M+H)⁺ and 471.8 (M+Na)⁺.
HPLC: 98.35% (210 nm).

Example 8T

Synthesis of 2-(3-(2-((4-(furan-2-yl)-N-methylbenzamido)methyl) phenoxy)propyl) cyclopropane-1-carboxylic acid (Compound 8t)

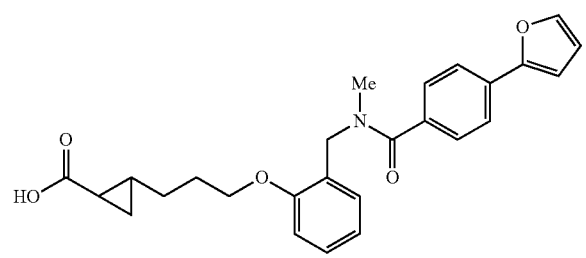 [SMILES: CN(Cc1ccccc1OCCCC1CC1C(=O)O)C(=O)c1ccc(-c2ccco2)cc1]

Synthetic Scheme-1:

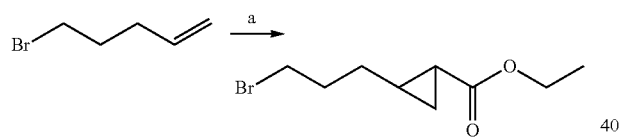

Reagents and conditions:
a) Ethyl diazoacetate, CuSO₄, cyclohexane, 80° C., 18 h.

Step-1: Synthesis of ethyl 2-(3-bromopropyl)cyclopropane-1-carboxylate (Compound 8t-i)

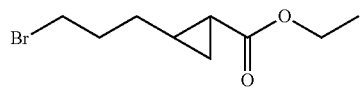

In a 100 mL round bottom flask, a solution of 5-bromopent-1-ene (5.0 g, 33.55 mmol) in cyclohexane (10 mL) was treated with CuSO₄ (0.53 g, 3.35 mmol) at RT. The reaction mixture was heated to 80° C. and treated with a solution of ethyl diazoacetate (1.912 g, 16.78 mmol) in cyclohexane (10 mL) at under nitrogen atmosphere. The reaction mixture was stirred at same temperature for 18 h. Upon completion of reaction (TLC), the reaction mixture was cooled to RT and filtered through a silica gel (60-120 mesh) pad and washed with 30% EtOAc in hexanes. The combined filtrate was concentrated under reduced pressure and residue obtained was further purified by silica gel column chromatography (gradient elution, 0-10% EtOAc in hexanes) to afford the title compound. Yield: 6.7 g (85.8%).

¹H NMR (400 MHz, CDCl₃): δ 4.11 (q, J=7.2 Hz, 2H), 3.44 (t, J=6.3 Hz, 2H), 2.02-1.92 (m, 2H), 1.54-1.30 (m, 4H), 1.25 (t, J=6.6 Hz, 3H), 1.20-1.14 (m, 1H), 0.76-0.70 (m, 1H).

Step-2: Synthesis of ethyl 2-(3-(2-((4-(furan-2-yl)-N-methylbenzamido)methyl)phenoxy) propyl)cyclopropane-1-carboxylate (Compound 8t-ii)

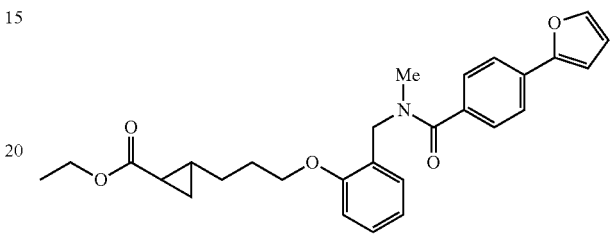

The title compound was synthesized N-(2-hydroxybenzyl)-N,2-dimethylbenzofuran-5-carboxamide (0.30 g, 1.01 mmol) and ethyl 2-(3-bromopropyl)cyclopropane-1-carboxylate (0.275 g, 2.03 mmol) following the experimental procedure described in step-3 of Example 8CC. Yield: 0.23 g (51.0%).

LCMS (ESI+, m/z): 462.2 (M+H)⁺ and 484.1 (M+Na)⁺.

Step-3: Synthesis of 2-(3-(2-((4-(furan-2-yl)-N-methylbenzamido)methyl)phenoxy) propyl)cyclopropane-1-carboxylic acid (Compound 8t)

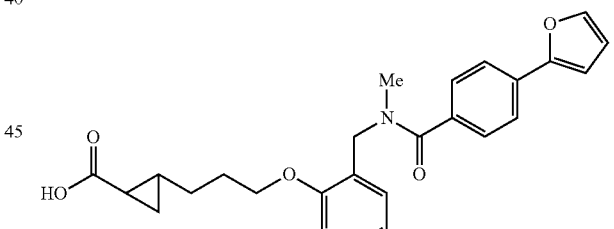

The title compound was synthesized from ethyl 2-(3-(2-((4-(furan-2-yl)-N-methylbenzamido)methyl)phenoxy)propyl)cyclopropane-1-carboxylate (0.2 g, 0.21 mmol) following the experimental procedure described in step-10 of Example 8A. Yield: 0.085 g, (45.5%).

¹H NMR (400 MHz, DMSO-d₆): δ 11.80 (brs, 1H), 7.75-7.72 (m, 3H), 7.47 (d, J=8.0 Hz, 2H), 7.28-7.24 (m, 1H), 7.20 (d, J=6.8 Hz, 1H), 7.00-6.95 (m, 3H), 6.60 (brs, 1H), 4.58 (brs, 2H), 4.00 (brs, 2H), 2.89 (s, 3H), 1.77 (m, 2H), 1.59 (m, 1H), 1.40 (brs, 1H), 1.26 (brs, 2H), 0.96-0.95 (m, 1H), 0.76-0.55 (m, 1H).

LCMS (ESI+, m/z): 434.2 (M+H)⁺.

HPLC: % (210 nm).

Example 8U & 8V (1R*,2S*)-2-(3-(2-((4-(furan-2-yl)-N-methylbenzamido)methyl)phenoxy)propyl) cyclopropane-1-carboxylic acid (Compound 8u), and (1R*,2R*)-2-(3-(2-((4-(furan-2-yl)-N-methylbenzamido)methyl)phenoxy)propyl) cyclopropane-1-carboxylic acid (Compound 8v)

Examples 8W and 8X (1R,2S)-2-(3-(2-((4-(furan-2-yl)-N-methylbenzamido)methyl)phenoxy)propyl) cyclopropane-1-carboxylic acid (Compound 8w), and (1S,2R)-2-(3-(2-((4-(furan-2-yl)-N-methylbenzamido)methyl)phenoxy)propyl) cyclopropane-1-carboxylic acid (Compound 8w)*

*Note: absolute configuration of compounds 8w and 8z is arbitrary

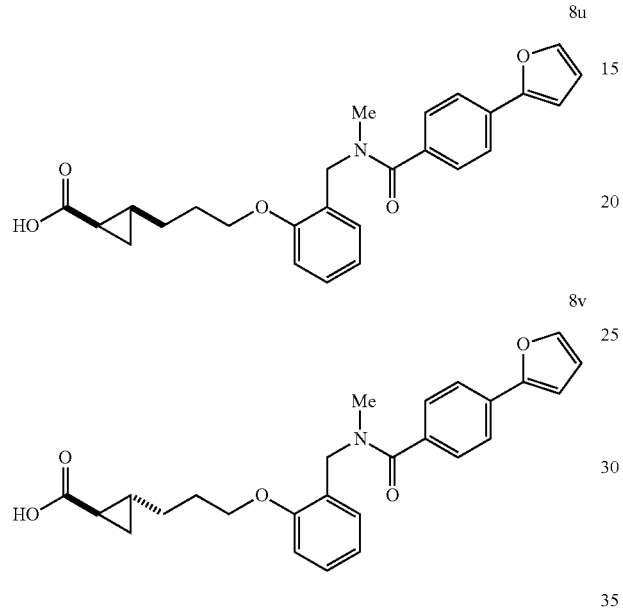

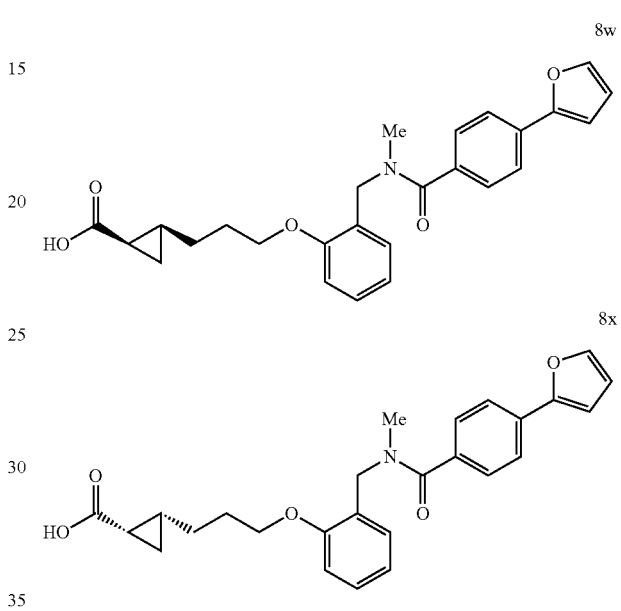

The title compound was obtained from separation of diastereomers from 2-(3-(2-((4-(furan-2-yl)-N-methylbenzamido)methyl)phenoxy)propyl)cyclopropane-1-carboxylic acid (1.4 g) by preparative HPLC (Column: Gemini Luna C18 (250 mm×21.5 mm×5 m); Flow: 20 mL/min; Mobile phase: 10 mM NH$_4$OAc in H$_2$O (A)/MeCN (B); T/% B: 0/30, 2/40, 3/80) to afford ((1R*,2S*)-2-(3-(2-((4-(furan-2-yl)-N-methylbenzamido)methyl) phenoxy)propyl)cyclopropane-1-carboxylic acid and (0.7 g) and (1R*,2R*)-2-(3-(2-((4-(furan-2-yl)-N-methyl benzamido)methyl)phenoxy) propyl)cyclopropane-1-carboxylic acid (0.3 g).

Compound 8u $^1$H NMR (400 MHz, DMSO-d$_6$, 90° C.): δ 11.60 (brs, 1H), 7.74-7.72 (m, 3H), 7.47 (d, J=8.4 Hz, 2H), 7.28-7.24 (m, 1H), 7.20 (d, J=7.2 Hz, 1H), 7.00-6.95 (m, 3H), 6.60 (brs, 1H), 4.59 (brs, 2H), 4.02 (t, J=6.4 Hz, 2H), 2.90 (s, 3H), 1.80-1.77 (m, 2H), 1.44-1.40 (m, 2H), 1.32-1.25 (m, 2H), 0.99-0.95 (m, 1H), 0.69-0.64 (m, 1H).

LCMS (ESI+, m/z): 434.2 (M+H)$^+$.

HPLC: 96.44% (210 nm). (R$_t$: 5.29 min).

Compound 8v $^1$H NMR (400 MHz, DMSO-d$_6$, 90° C.): δ 11.65 (brs, 1H), 7.74-7.72 (m, 3H), 7.47 (d, J=8.4 Hz, 2H), 7.28-7.24 (m, 1H), 7.20 (d, J=7.2 Hz, 1H), 7.00-6.95 (m, 3H), 6.60 (brs, 1H), 4.60 (brs, 2H), 4.03-3.99 (m, 2H), 2.92 (s, 3H), 1.80-1.75 (m, 2H), 1.68-1.60 (m, 3H), 1.28-1.22 (m, 1H), 0.99-0.94 (m, 1H), 0.75-0.71 (m, 1H).

LCMS (ESI+, m/z): 434.2 (M+H)$^+$.

HPLC: 94.07% (210 nm). (RT: 5.38 min).

The title compound was obtained separation of enantiomers of 2-(3-(2-((4-(furan-2-yl)-N-methylbenzamido)methyl) phenoxy)propyl)cyclopropane-1-carboxylic acid (0.65 g) by chiral preparative HPLC (Column: Phenomenex Lux Amylose-2 (250 mm×21.20 mm), 5.0μ; Flow: 20.0 mL/min; Isocratic: 77:23; mobile phase: Hexane (A)/0.1% TFA in EtOH (B)) to afford (1R,2S)-2-(3-(2-((4-(furan-2-yl)-N-methylbenzamido)methyl)phenoxy)propyl) cyclopropane-1-carboxylic acid (0.088 g, >99% ee) and (1S,2R)-2-(3-(2-((4-(furan-2-yl)-N-methylbenzamido)methyl)phenoxy) propyl)cyclopropane-1-carboxylic acid (0.17 g, 98% ee).

Compound 8w $^1$H NMR (400 MHz, DMSO-d$_6$, 90° C.): δ 7.74-7.72 (m, 3H), 7.47 (d, J=8.4 Hz, 2H), 7.28-7.24 (m, 1H), 7.20 (d, J=7.2 Hz, 1H), 7.00-6.95 (m, 3H), 6.60 (m, 1H), 4.60 (brs, 2H), 4.03 (t, J=6.4 Hz, 2H), 2.90 (s, 3H), 1.82-1.79 (m, 2H), 1.42-1.40 (m, 2H), 1.32-1.26 (m, 2H), 1.00-0.99 (m, 1H), 0.69-0.65 (m, 1H).

LCMS (ESI+, m/z): 434.3 (M+H)$^+$.

HPLC: 98.72% (210 nm).

Compound 8x $^1$H NMR (400 MHz, DMSO-d$_6$, 90° C.): δ 7.72-7.70 (m, 3H), 7.45 (d, J=8.4 Hz, 2H), 7.27-7.23 (m, 1H), 7.19 (d, J=7.2 Hz, 1H), 6.99-6.93 (m, 3H), 6.58-6.57 (m, 1H), 4.60 (brs, 2H), 4.03 (t, J=6.4 Hz, 2H), 2.89 (s, 3H), 1.80-1.75 (m, 2H), 1.42-1.40 (m, 2H), 1.32-1.26 (m, 2H), 0.98-0.94 (m, 1H), 0.67-0.63 (m, 1H).

LCMS (ESI+, m/z): 434.3 (M+H)$^+$.

HPLC: 97.61% (210 nm).

Example 8Y

Synthesis of 2-((3-(2-((4-(furan-2-yl)-N-methylbenzamido)methyl)phenoxy) propyl)thio)acetic acid (Compound 8y)

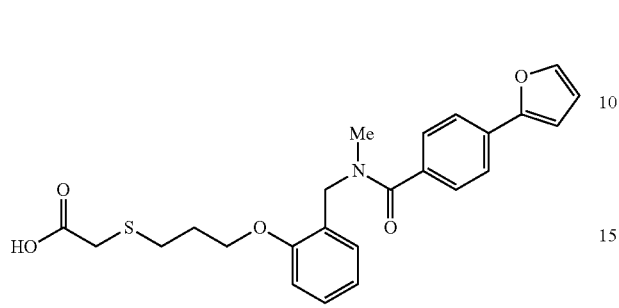

Synthetic Scheme:

Step-1: Synthesis of N-(2-(3-bromopropoxy)benzyl)-4-(furan-2-yl)-N-methylbenzamide (Compound 8y-i)

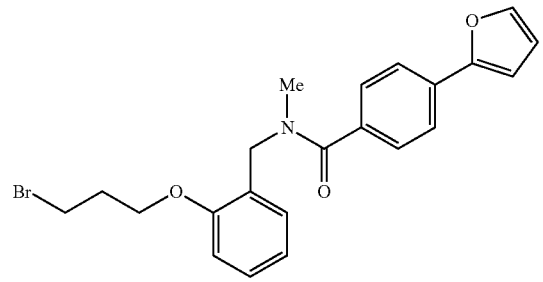 [SMILES: CN(Cc1ccccc1OCCCBr)C(=O)c1ccc(-c2ccco2)cc1]

In a 100 mL round bottom flask, a solution of 4-(furan-2-yl)-N-(2-hydroxybenzyl)-N-methylbenzamide (0.5 g,

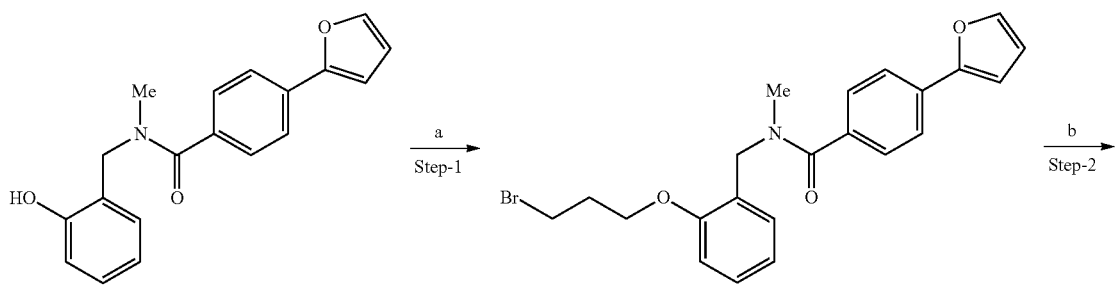

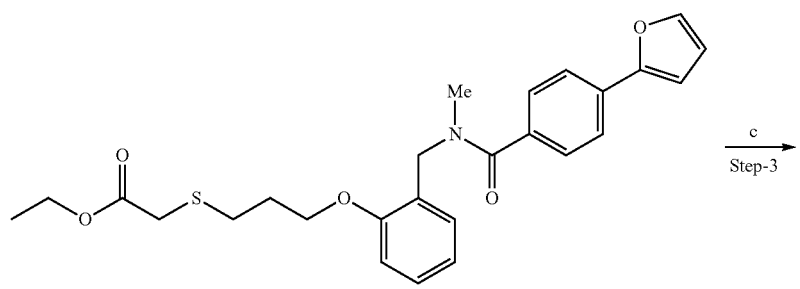

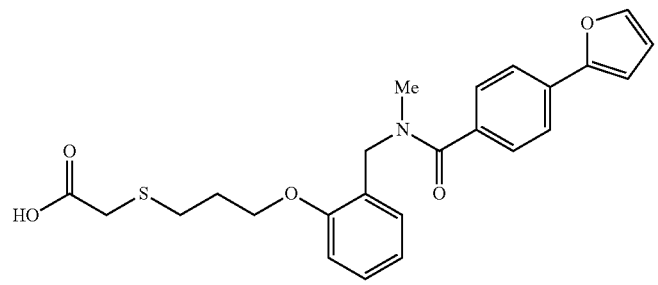

Reagents and conditions:
a) 1.3-Dibromopropane, K₂CO₃, DMF, 110° C., 3 days;
b) Ethyl 2-mercaptoacetate, K₂CO₃, acetone, reflux, 3 h;
c) LiOH·H₂O, THF, EtOH, H₂O, RT, 70° C., 2 h.

1.62 mmol) in DMF (50 mL) was treated with K₂CO₃ (0.337 g, 2.44 mmol) and 1,3-dibromopropane (0.651 g, 3.24 mmol) at RT under nitrogen atmosphere. The resulting reaction mixture was stirred at 110° C. for 3 days. The reaction mixture was cooled to RT, filtered and washed with ethyl acetate. The combined filtrate was concentrated under reduced pressure and residue obtained was diluted with cold water (50 mL), before extracting with ethyl acetate (200 mL). The organic extract was washed with brine, dried over anhydrous Na₂SO₄ and concentrated under reduced pressure. The residue obtained was purified by silica gel column chromatography (elution, 20% EtOAc-hexanes) to afford the title compound. Yield: 0.351 g (53.2%).

LCMS (ESI+, m/z): 427.7, 429.7 (M+H)⁺.

Step-2: Synthesis of ethyl 2-((3-(2-((4-(furan-2-yl)-N-methylbenzamido)methyl)phenoxy) propyl)thio) acetate (Compound 8y-ii)

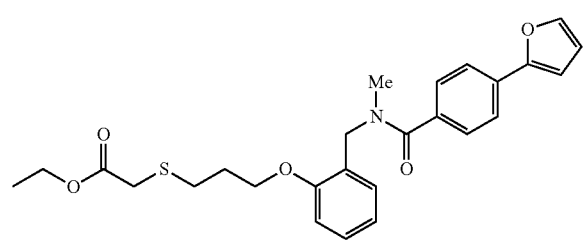 [SMILES: CCOC(=O)CSCCCOc1ccccc1CN(C)C(=O)c1ccc(-c2ccco2)cc1]

In a 50 mL round bottom flask, a solution of N-(2-(3-bromopropoxy)benzyl)-4-(furan-2-yl)-N-methylbenzamide (0.3 g, 0.70 mmol) in acetone (10 mL) was treated with K₂CO₃ (0.289 g, 2.10 mmol) and ethyl 2-mercaptoacetate (0.14 g, 1.05 mmol) at RT under nitrogen atmosphere. The resulting reaction mixture was stirred at reflux temperature for 3 h. The reaction mixture was cooled to RT, filtered and washed with ethyl acetate. The combined filtrate was concentrated under reduced pressure and residue obtained was diluted with cold water (50 mL), before extracting with ethyl acetate (100 mL). The organic extract was washed with brine, dried over anhydrous Na₂SO₄ and concentrated under reduced pressure. The residue obtained was purified by silica gel column chromatography (elution, 50% EtOAc-hexanes) to afford the title compound. Yield: 0.291 g (89.1%).

LCMS (ESI+, m/z): 467.8 (M+H)⁺.

Step-3: Synthesis of 2-((3-(2-((4-(furan-2-yl)-N-methylbenzamido)methyl)phenoxy) propyl)thio) acetic acid (Compound 8y)

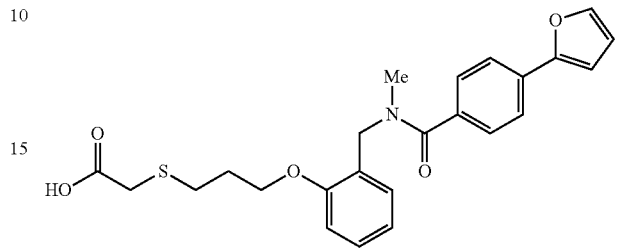

The title compound was synthesized from ethyl 2-((3-(2-((4-(furan-2-yl)-N-methylbenzamido)methyl)phenoxy)propyl)thio)acetate (0.2 g, 0.428 mmol) following the experimental procedure described in step-10 of Example 8A. Yield: 0.16 g (85.1%).

¹H NMR (400 MHz, DMSO-d₆, 60° C.): δ 12.30 (brs, 1H), 7.75-7.73 (m, 3H), 7.48 (d, J=8.0 Hz, 2H), 7.29-7.25 (m, 1H), 7.21-7.19 (m, 1H), 7.02-6.96 (m, 3H), 6.61 (brs, 1H), 4.60 (brs, 2H), 4.06 (brs, 2H), 3.23 (s, 2H), 2.89 (s, 3H), 2.73 (brs, 2H), 1.99 (brs, 2H).

LCMS (ESI+, m/z): 440.4 (M+H)⁺ and 462.1 (M+Na)⁺. HPLC: 93.66% (210 nm).

Example 8Z

Synthesis of 6-(2-((N,2-dimethylbenzofuran-5-carboxamido)methyl)phenoxy)-2,2-dimethylhexanoic acid (Compound 8z)

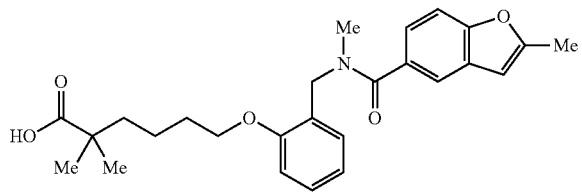 [SMILES: Cc1cc2cc(C(=O)N(C)Cc3ccccc3OCCCCC(C)(C)C(=O)O)ccc2o1]

Synthetic Scheme:

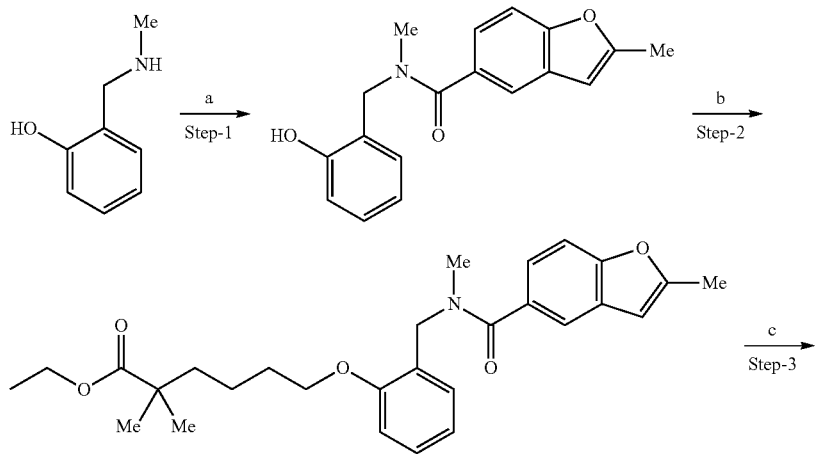

-continued

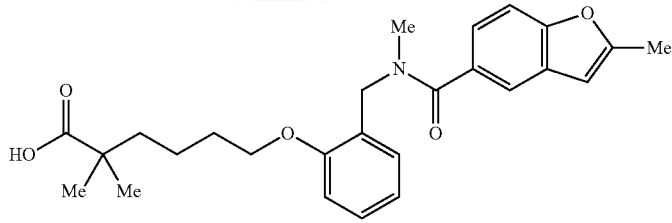

Reagents and conditions:
a) 2-Methylbenzofuran-5-carboxylic acid, EDCI•HCl, HOBt, Et₃N, DMF, RT;
b) Ethyl 6-bromo-2,2-dimethylhexanoate, K₂CO₃, DMF, RT;
c) LiOH•H₂O, THF, EtOH, H₂O, RT.

Step-1: Synthesis of N-(2-hydroxybenzyl)-N,2-dimethylbenzofuran-5-carboxamide (Compound 8z-i)

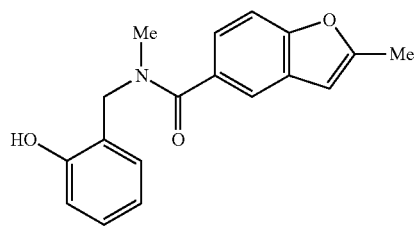 [SMILES: Cc1cc2cc(C(=O)N(C)Cc3ccccc3O)ccc2o1]

The title compound was synthesized from 2-((methylamino)methyl)phenol (0.389 g, 2.84 mmol) and 2-methylbenzofuran-5-carboxylic acid (0.5 g, 2.84 mmol) following the experimental procedure described in step-8 of Example 8A. Yield: 0.591 g (70.6%)

$^1$H NMR (300 MHz, DMSO-d$_6$): 9.70 (s, 1H), 7.62-7.50 (m, 2H), 7.27-7.09 (m, 3H), 6.80 (t, J=6.9 Hz, 2H), 6.60 (br, 1H), 4.59-4.40 (m, 2H), 2.87 (s, 3H), 2.43 (s, 3H).

LCMS (ESI+, m/z): 295.8 (M+H)$^+$

Step-2: Synthesis of ethyl 6-(2-((N,2-dimethylbenzofuran-5-carboxamido)methyl) phenoxy)-2,2-dimethylhexanoate (Compound 8z-ii)

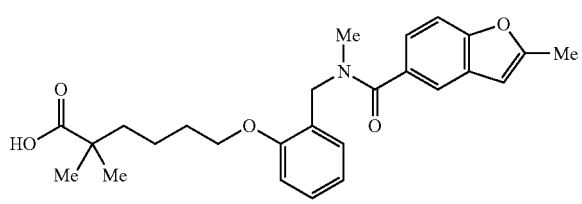 [SMILES: Cc1cc2cc(C(=O)N(C)Cc3ccccc3OCCCCC(C)(C)C(=O)O)ccc2o1]

The title compound was synthesized from N-(2-hydroxybenzyl)-N,2-dimethylbenzofuran-5-carboxamide (0.2 g, 0.68 mmol) and ethyl 6-bromo-2,2-dimethylhexanoate (0.169 g, 0.68 mmol) following the experimental procedure described in step-9 of Example 8A. Yield: 0.301 g (96%)

LCMS (ESI+, m/z): 466.3 (M+H)$^+$

Step-3: Synthesis of 6-(2-((N,2-dimethylbenzofuran-5-carboxamido)methyl)phenoxy)-2, 2-dimethylhexanoic acid (Compound 8z)

The title compound was synthesized from ethyl 6-(2-((N, 2-dimethylbenzofuran-5-carboxamido)methyl)phenoxy)-2, 2-dimethylhexanoate (0.35 g, 0.75 mmol) following the experimental procedure described in step-10 of Example 8A. Yield: 0.211 (64.5%)

$^1$H NMR (400 MHz, DMSO-d$_6$, 90° C.): 11.90 (br, 1H), 7.58 (s, 1H), 7.49 (d, J=8.0 Hz, 1H), 7.28-7.23 (m, 2H), 7.19 (d, J=6.8 Hz, 1H), 6.99-6.94 (m, 2H), 6.59 (s, 1H), 4.58 (br s, 2H), 3.96 (br s, 2H), 2.89 (s, 3H), 2.45 (s, 3H), 1.65 (br, 2H), 1.55-1.46 (m, 2H), 1.34 (br, 2H), 1.06 (s, 6H).

LCMS (ESI+, m/z): 437.8 (M+H)$^+$ and 459.8 (M+Na)$^+$.

HPLC: 99.45%. (210 nm).

Example 8AA

Synthesis of (E)-6-(2-((4-(furan-2-yl)-N-methylbenzamido)methyl)-4-(trifluoromethyl) phenoxy)-4-methylhex-4-enoic acid (Compound 8aa)

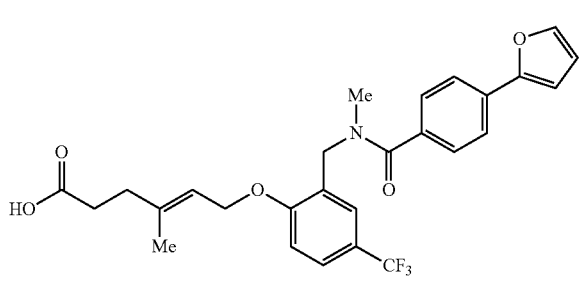 [SMILES: C/C(=C\COc1ccc(C(F)(F)F)cc1CN(C)C(=O)c1ccc(-c2ccco2)cc1)CCC(=O)O]

Synthetic Scheme:
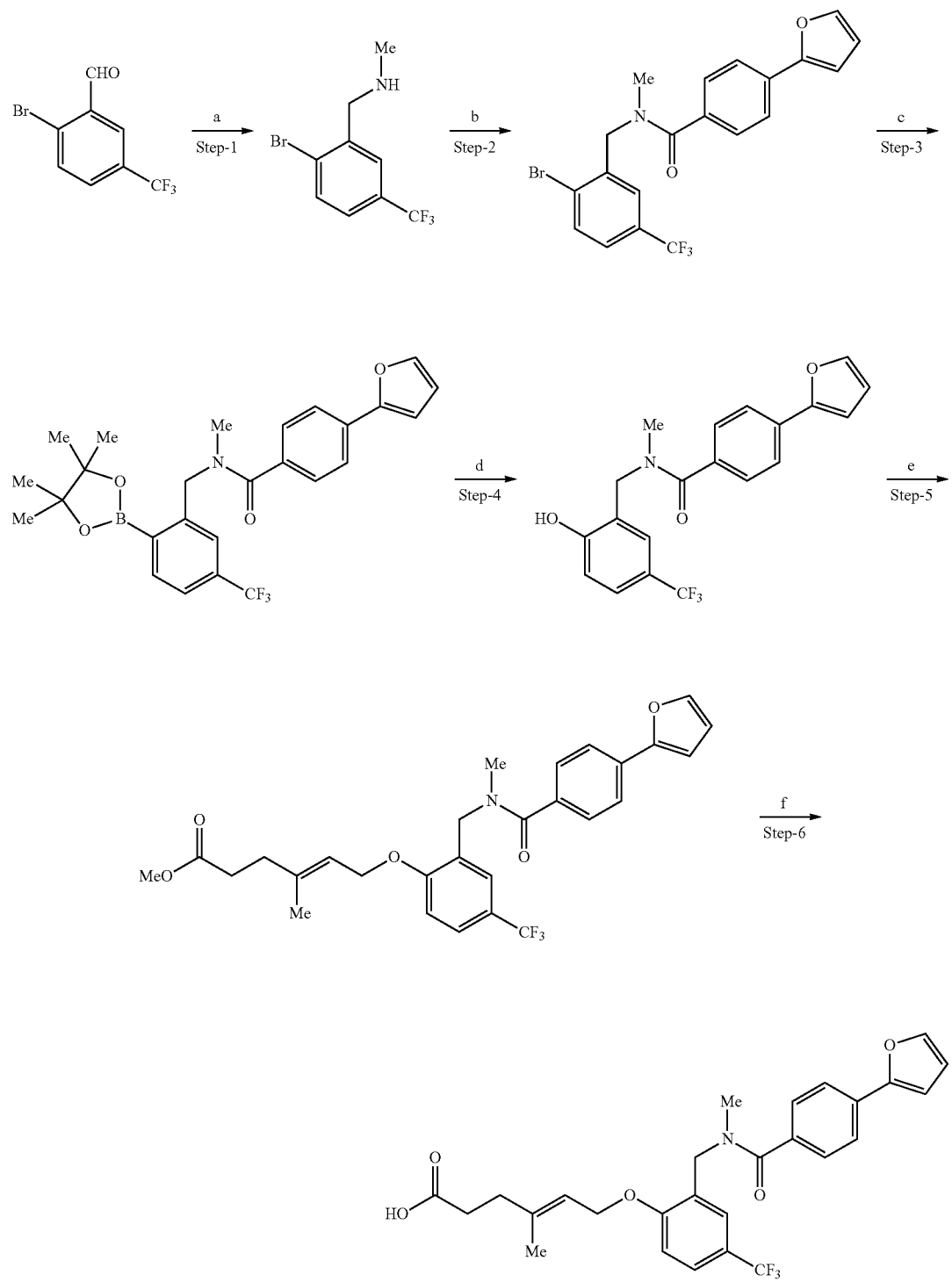
Reagents and conditions:
a) MeNH₂·HCl, Et₃N, NaBH₄, MeOH, RT, 2 h;
b) 4-(Furan-2-yl)benzoic acid, EDCl·HCl, HOBt, Et₃N, DMF, RT, 3 h;
c) Bis(pinacolato)diboron, PdCl₂(dppf)·CH₂Cl₂, 1,4-dioxane, KOAc, 90° C., 12 h:
d) NaBO₃·4H₂O, THF, H₂O, RT, 15 h;
e) Methyl (E)-6-bromo-4-methylhex-4-enoate, K₂CO₃, DMF, RT, 12 h;
f) LiOH·H₂O, THF, MeOH, H₂O, RT, 1 h.

Step-1: Synthesis of 1-(2-bromo-5-(trifluoromethyl)phenyl)-N-methylmethanamine (Compound 8aa-i)

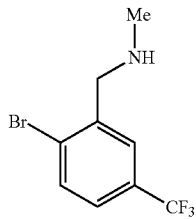

The title compound was synthesized from 2-bromo-5-(trifluoromethyl)benzaldehyde (5.0 g, 19.76 mmol) and MeNH$_2$.HCl (6.7 g, 98.91 mmol) following the experimental procedure described in step-6 of example-1. Yield: 3.12 g (59.2%).
$^1$H NMR (300 MHz, CDCl$_3$): δ 7.68-7.65 (m, 2H), 7.39-7.36 (m, 1H), 3.87 (s, 2H), 2.48 (s, 3H).
LCMS (ESI+, m/z): 267.8, 270.0 (M+H)$^+$.

Step-2: Synthesis of N-(2-bromo-5-(trifluoromethyl)benzyl)-4-(furan-2-yl)-N-methylbenzamide (Compound 8aa-ii)

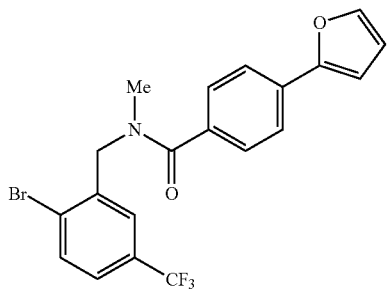 [SMILES: CN(Cc1cc(C(F)(F)F)ccc1Br)C(=O)c1ccc(-c2ccco2)cc1]

The title compound was synthesized from 1-(2-bromo-5-(trifluoromethyl)phenyl)-N-methylmethanamine (2.1 g, 7.86 mmol) and 4-(furan-2-yl)benzoic acid (1.46 g, 7.86 mmol) following the experimental procedure described in step-8 of Example 8A. Yield: 3.12 g (59.2%).
LCMS (ESI+, m/z): 438.0, 440.1 (M+H)$^+$.

Step-3: Synthesis of 4-(furan-2-yl)-N-methyl-N-(2-(4,4,5,5-tetramethyl-1,3,2-dioxaborolan-2-yl)-5-(trifluoromethyl)benzyl)benzamide (Compound 8aa-iii)

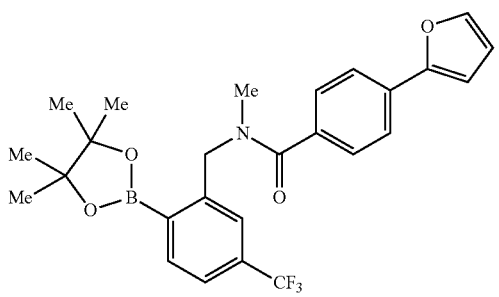 [SMILES: CN(Cc1cc(C(F)(F)F)ccc1B1OC(C)(C)C(C)(C)O1)C(=O)c1ccc(-c2ccco2)cc1]

In a 20 mL resealable reaction tube, N-(2-bromo-5-(trifluoromethyl)benzyl)-4-(furan-2-yl)-N-methylbenzamide (0.25 g, 0.57 mmol) and bis(pinacolato)diboron (0.725 g, 2.85 mmol) were dissolved in degassed 1,4-dioxane (10 mL) at RT under nitrogen atmosphere. PdCl$_2$(dppf).CH$_2$Cl$_2$ (0.093 g, 0.11 mmol) and KOAc (0.28 g, 2.85 mmol) were sequentially added to the above solution under nitrogen atmosphere. The resulting mixture was degassed by purging with argon gas for 15 min and reaction mixture was heated at 90° C. for 12 h. Upon completion of the reaction (TLC), the reaction mixture was cooled to RT, diluted with cold water and extracted with ethyl acetate (3×50 mL). The combined organic extract was washed with brine, dried over anhydrous Na$_2$SO$_4$ and concentrated under reduced pressure to get the title compound. Yield: 0.20 g (72.2%).
LCMS (ESI+, m/z): 486.3 (M+H)$^+$.

Step-4: Synthesis of 4-(furan-2-yl)-N-(2-hydroxy-5-(trifluoromethyl)benzyl)-N-methylbenzamide (Compound 8aa-iv)

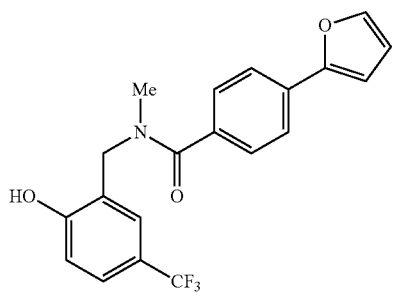

In 100 mL round bottom flask, a solution of 4-(furan-2-yl)-N-methyl-N-(2-(4,4,5,5-tetramethyl-1,3,2-dioxaborolan-2-yl)-5-(trifluoromethyl)benzyl)benzamide (1.5 g, 3.09 mmol) in THF (15 mL) and H$_2$O (15 mL) was treated with NaBO$_3$.4H$_2$O (1.4 g, 9.27 mmol) at RT. The resulting reaction mixture was stirred at RT for 15 h. Upon completion of reaction (TLC), the reaction mixture was diluted with water (30 mL) and extracted with EtOAc (3×50 mL). The combined organic extract was washed with brine and dried over anhydrous Na$_2$SO$_4$. The solvent was removed under reduced pressure. The residue obtained was purified by silica gel column chromatography (elution, 40% EtOAc in hexanes) to yield the title compound. Yield: 0.51 g (43.9%).
$^1$H NMR (300 MHz, CDCl$_3$): δ 10.60 (s, 1H), 7.72 (d, J=8.1 Hz, 2H), 7.55-7.50 (m, 4H), 7.42-7.41 (m, 1H), 7.06 (d, J=8.7 Hz, 1H), 6.75 (d, J=4.2 Hz, 1H), 6.50 (dd, J=3.3, 1.8 Hz, 1H), 4.64 (s, 2H), 3.09 (s, 3H).
LCMS (ESI, m/z): 376.0 (M+H)$^+$.

Step-5: Synthesis of methyl (E)-6-(2-((4-(furan-2-yl)-N-methylbenzamido)methyl)-4-(trifluoromethyl)phenoxy)-4-methylhex-4-enoate (Compound 8aa-v)

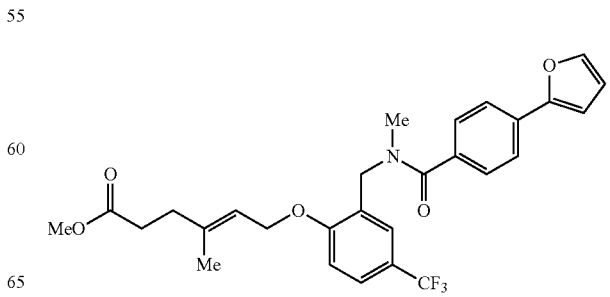

The title compound was synthesized from 4-(furan-2-yl)-N-(2-hydroxy-5-(trifluoromethyl)benzyl)-N-methylbenzamide (0.3 g, 0.80 mmol) and methyl (E)-6-bromo-4-methylhex-4-enoate (0.521 g, 2.40 mmol) following the experimental procedure described in step-9 of Example 8A. Yield: 0.25 g (60.7%).

LCMS (ESI, m/z): 516.3 (M+H)+ and 538.3 (M+Na)+.

Step-6: Synthesis of (E)-6-(2-((4-(furan-2-yl)-N-methylbenzamido)methyl)-4-(trifluoromethyl) phenoxy)-4-methylhex-4-enoic acid (Compound 8aa)

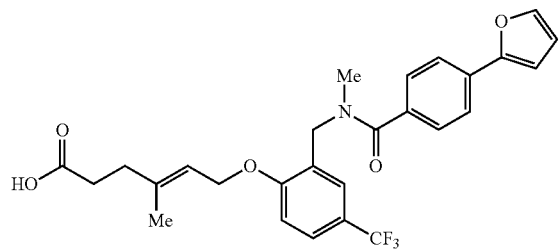 [SMILES: C/C(=C\COc1ccc(C(F)(F)F)cc1CN(C)C(=O)c1ccc(-c2ccco2)cc1)CCC(=O)O]

The title compound was synthesized from methyl (E)-6-(2-((4-(furan-2-yl)-N-methylbenzamido)methyl)-4-(trifluoromethyl)phenoxy)-4-methylhex-4-enoate (0.25 g, 0.48 mmol) following the experimental procedure described in step-10 of Example 8A. Yield: 0.14 g (57.6%).

$^1$H NMR (300 MHz, DMSO-$d_6$, 60° C.): δ 11.90 (brs, 1H), 7.74-7.71 (m, 3H), 7.61 (d, J=6.9 Hz, 1H), 7.43-7.41 (m, 3H), 7.20 (d, J=8.1 Hz, 1H), 6.98 (d, J=3.3 Hz, 1H), 6.59-6.58 (m, 1H), 5.42 (brs, 1H), 4.46 (d, J=5.4 Hz, 2H), 4.59 (brs, 2H), 2.72 (s, 3H), 2.31-2.25 (m, 4H), 1.69 (s, 3H).

LCMS (ESI+, m/z): 502.3 (M+H)+

HPLC: 97.2% (210 nm).

Example 8BB

Synthesis of (E)-6-(4-cyclopropyl-2-((4-(furan-2-yl)-N-methylbenzamido) methyl)phenoxy)-4-methylhex-4-enoic acid (Compound 8bb)

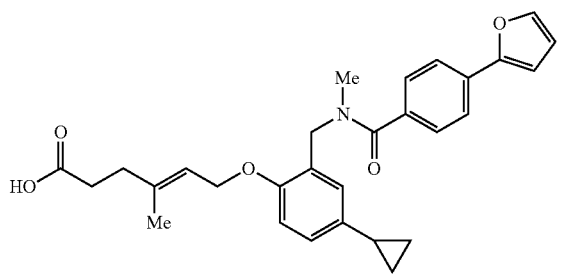 [SMILES: C/C(=C\COc1ccc(C2CC2)cc1CN(C)C(=O)c1ccc(-c2ccco2)cc1)CCC(=O)O]

Synthetic Scheme:

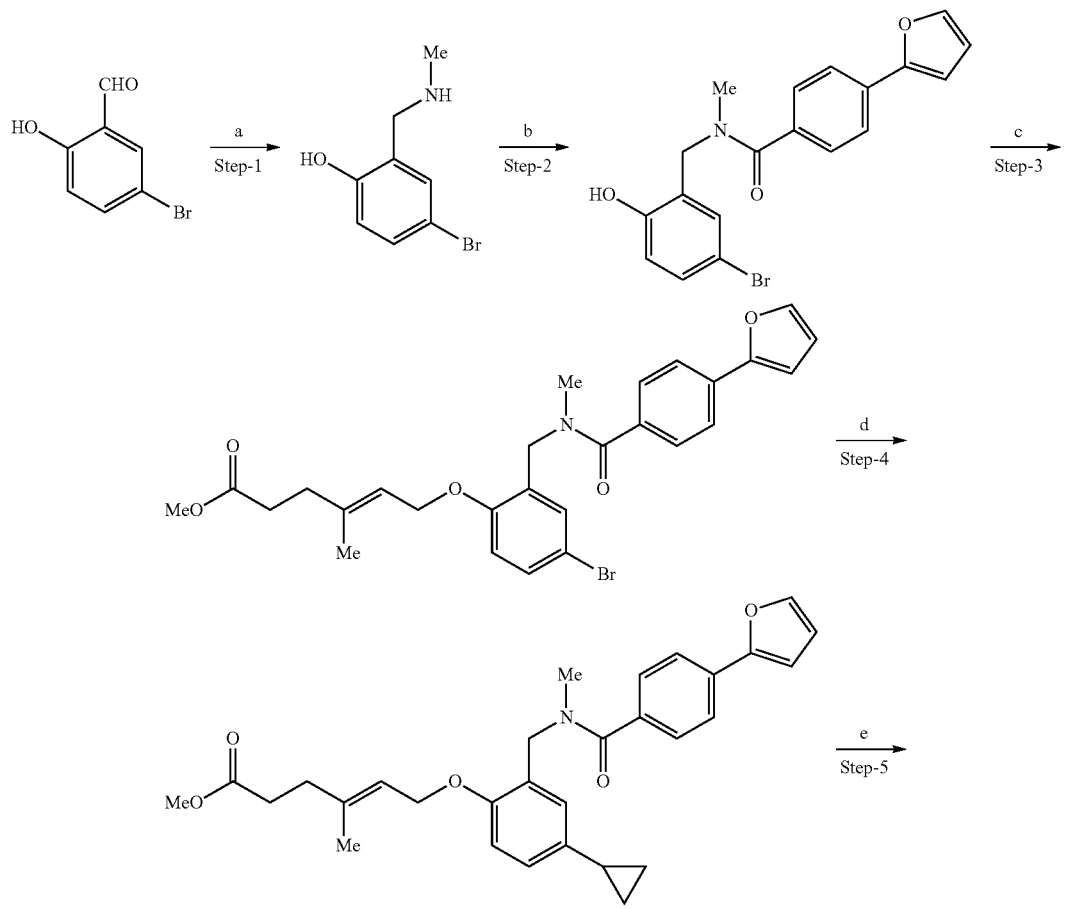

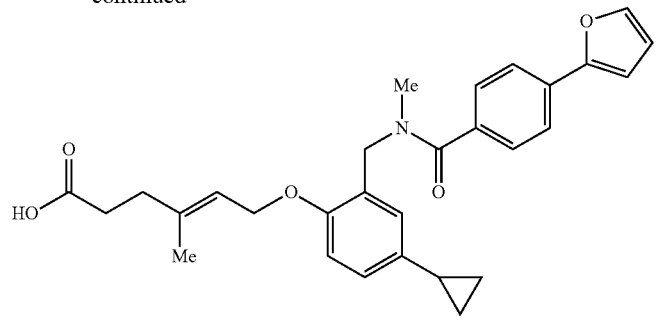

Reagents and conditions:
a) MeNH₂•HCl, Et₃N, NaBH₄, MeOH, RT, 2 h;
b) 4-(Furan-2-yl)benzoic acid, EDCl•HCl, HOBt, Et₃N, DMF, RT, 3 h;
c) Methyl (E)-6-bromo-4-methylhex-4-enoate, K₂CO₃, DMF, RT, 12 h;
d) Cyclopropylboronic acid, Pd(OAc)₂, PCy₃, K₃PO₄, toluene, H₂O, 100° C., 12 h;
e) LiOH•H₂O, THF, MeOH, H₂O, RT, 1 h.

Step-1: Synthesis of 4-bromo-2-((methylamino) methyl)phenol (Compound 8bb-i)

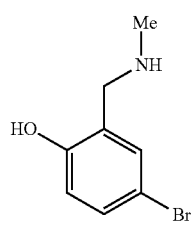

The title compound was synthesized from 5-bromo-2-hydroxybenzaldehyde (5.0 g, 24.87 mmol) and MeNH₂.HCl (8.4 g, 124.37 mmol) following the experimental procedure described in step-6 of Example 8A. Yield: 3.99 (74.7%).
$^1$H NMR (300 MHz, DMSO-d$_6$): δ 7.23-7.17 (m, 2H), 6.64 (d, J=8.7 Hz, 1H), 5.26 (br, 2H), 3.72 (s, 2H), 2.24 (s, 3H).
LCMS (ESI+, m/z): 216.1, 218.1 (M+H)⁺.

Step-2: Synthesis of N-(5-bromo-2-hydroxybenzyl)-4-(furan-2-yl)-N-methylbenzamide (Compound 8bb-ii)

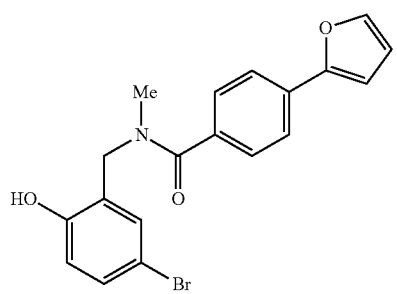

The title compound was synthesized from 4-bromo-2-((methylamino)methyl)phenol (2.2 g, 10.18 mmol) and 4-(furan-2-yl)benzoic acid (2.0 g, 10.18 mmol) following the experimental procedure described in step-8 of Example 8A. Yield: 2.2 g (56.1%).

$^1$H NMR (400 MHz, CDCl$_3$): δ 10.10 (s, 1H), 7.72 (d, J=8.0 Hz, 2H), 7.52 (d, J=8.4 Hz, 2H), 7.51 (s, 1H), 7.37-7.35 (m, 1H), 7.29-7.28 (m, 1H), 6.89 (d, J=8.4 Hz, 1H), 6.76-6.75 (m, 1H), 6.51-6.50 (m, 1H), 4.57 (s, 2H), 3.09 (s, 3H).
LCMS (ESI+, m/z): 386.0, 388.0 (M+H)⁺.

Step-3: Synthesis of methyl (E)-6-(4-bromo-2-((4-(furan-2-yl)-N-methylbenzamido) methyl)phenoxy)-4-methylhex-4-enoate (Compound 8bb-iii)

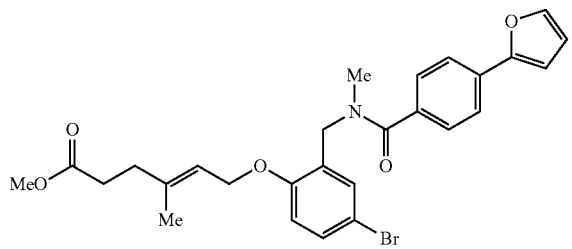 [SMILES: COC(=O)CC/C(C)=C/COc1ccc(Br)cc1CN(C)C(=O)c1ccc(-c2ccco2)cc1]

The title compound was synthesized from N-(5-bromo-2-hydroxybenzyl)-4-(furan-2-yl)-N-methylbenzamide (0.1 g, 2.59 mmol) and methyl (E)-6-bromo-4-methylhex-4-enoate (0.7 g, 3.36 mmol) following the experimental procedure described in step-9 of Example 8A. Yield: 1.0 g (73.5%).
LCMS (ESI+, m/z): 526.0, 527.9 (M+H)⁺.

Step-4: Synthesis of methyl (E)-6-(4-cyclopropyl-2-((4-(furan-2-yl)-N-methylbenzamido) methyl)phenoxy)-4-methylhex-4-enoate (Compound 8bb-iv)

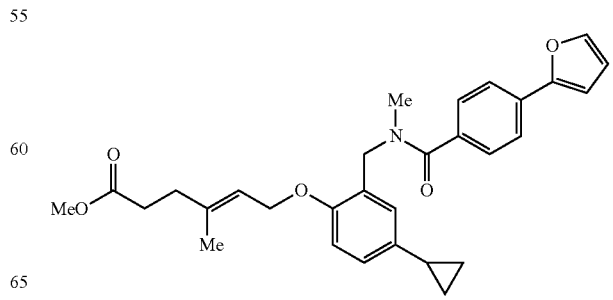

In a 100 mL resealable reaction tube, methyl (E)-6-(4-bromo-2-((4-(furan-2-yl)-N-methylbenzamido)methyl)phenoxy)-4-methylhex-4-enoate (0.4 g, 0.76 mmol) and cyclopropylboronic acid (0.134 g, 1.52 mmol) were dissolved in degassed mixture of toluene (10 mL) and water (4 mL) at RT under nitrogen atmosphere. Pd(OAc)$_2$ (0.034 g, 0.15 mmol), PCy$_3$ (0.43 g, 0.15 mmol) and K$_3$PO$_4$ (0.484 g, 2.28 mmol) were sequentially added to the above mixture under nitrogen atmosphere. The resulting mixture was degassed by purging argon gas for 15 min, and reaction mixture was heated to 110° C. for 12 h. Upon completion of reaction (TLC), the reaction mixture was cooled to RT, diluted with cold water and extracted with EtOAc (3×30 mL). The combined organic extract was washed with brine, dried over anhydrous Na$_2$SO$_4$ and concentrated under reduced pressure to get the title compound (0.3 g, 81.1%).

LCMS (ESI+, m/z): 488.4 (M+H)$^+$ and 510.4 (M+Na)$^+$

Step-5: Synthesis of (E)-6-(4-cyclopropyl-2-((4-(furan-2-yl)-N-methylbenzamido)methyl) phenoxy)-4-methylhex-4-enoic acid (Compound 8bb)

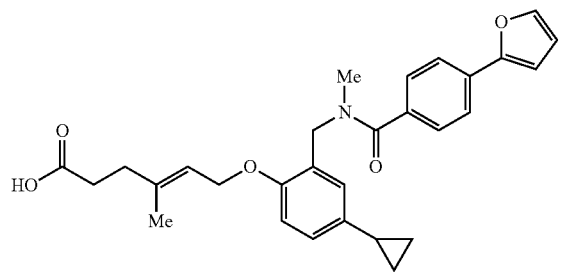 [SMILES: C/C(=C\COc1ccc(C2CC2)cc1CN(C)C(=O)c1ccc(-c2ccco2)cc1)CCC(=O)O]

The title compound was synthesized from methyl (E)-6-(4-cyclopropyl-2-((4-(furan-2-yl)-N-methylbenzamido)methyl)phenoxy)-4-methylhex-4-enoate (0.3 g, 0.62 mmol) following the experimental procedure described in step-10 of Example 8A. Yield: 0.11 g (37.8%).

$^1$H NMR (300 MHz, DMSO-d$_6$, 60° C.): δ 7.73-7.70 (m, 3H), 7.43 (d, J=8.4 Hz, 2H), 6.97-6.85 (m, 4H), 6.58 (dd, J=3.3, 1.8 Hz 1H), 5.38 (brs, 1H), 4.49 (brs, 4H), 2.85 (s, 3H), 2.30-2.24 (m, 5H), 1.65 (s, 3H), 0.90-0.84 (m, 2H), 0.57-0.52 (m, 2H).

LCMS (ESI+, m/z): 496.1 (M+Na)$^+$

HPLC: 98.5% (210 nm).

Example 8CC

Synthesis of (E)-6-(2-((4-(furan-2-yl)-N-methylbenzamido)methyl)phenoxy)hex-2-enoic acid (Compound 8cc)

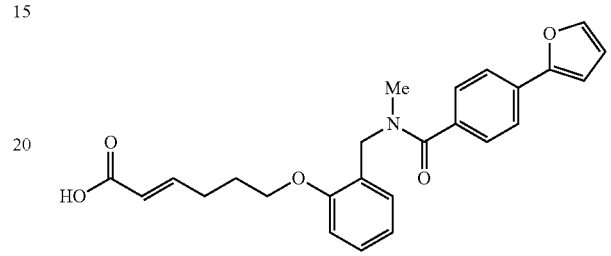

Synthetic Scheme-1:

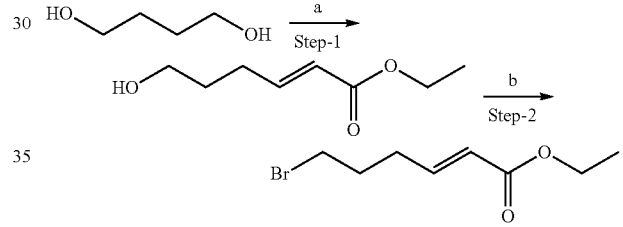

Reagents and conditions:
a) (Ethoxycarbonylmethylene)triphenylphophorane, MnO$_2$, DCM, 24 h;
b) CBr$_4$, PPh$_3$, THF, RT, 12 h.

Synthetic Scheme-2:

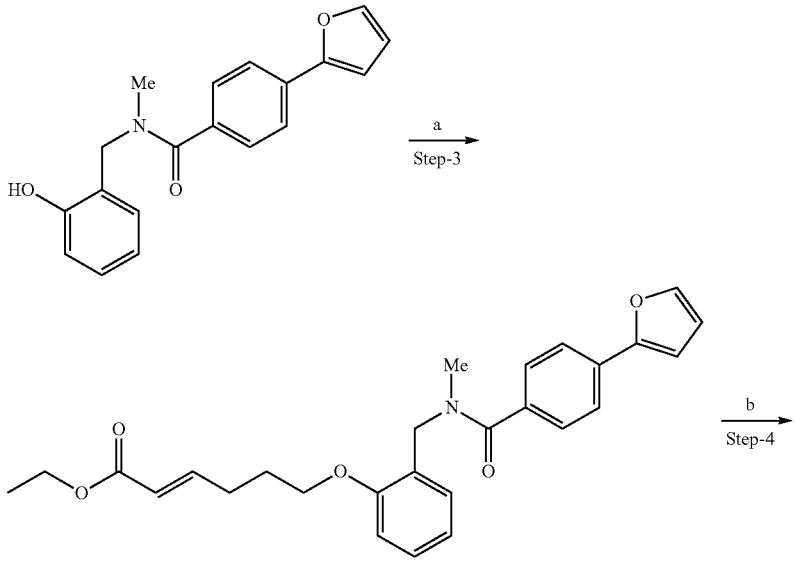

-continued

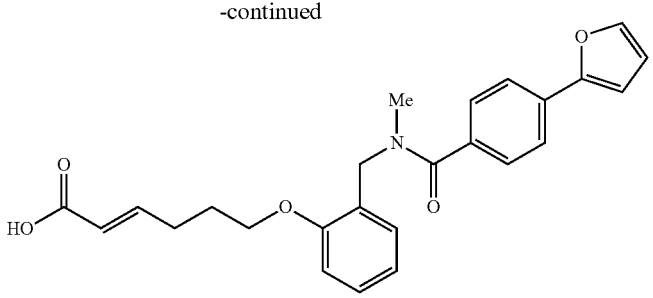

Reagents and conditions:
a) Ethyl (E)-6-bromohex-2-enoate, K₂CO₃, DMF, 80° C.;
b) LiOH•H₂O, THF, H₂O, RT, 12 h.

Step-1: Synthesis of ethyl
(E)-6-hydroxyhex-2-enoate (Compound 8cc-i)

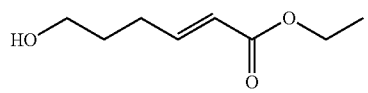

In a 500 mL round bottom flask, a solution of butane-1,4-diol (9.0 g, 99.86 mmol) and (ethoxycarbonylmethylene)triphenylphosphorane (83.40 g, 239.68 mmol) in DCM (90 mL) was treated with manganese dioxide (172.14 g, 1997.20 mmol) at RT. The resulting reaction mixture was stirred at RT for 24 h. Upon completion of reaction (TLC), the solid was filtered through a Celite® pad. The filtrate was washed with water and dried over anhydrous Na₂SO₄. The solvent was removed under reduced pressure to get the title compound. Yield: 2.15 g (13.6%).

¹H NMR (400 MHz, CDCl₃): δ 7.00-6.85 (m, 1H), 5.85 (d, J=16.8 Hz, 1H), 4.18 (q, J=7.2 Hz, 2H), 3.70-3.66 (m, 2H), 2.31 (q, J=7.6 Hz, 2H), 1.76-1.63 (m, 2H), 1.39 (brs, 1H), 1.28 (t, J=7.2 Hz, 3H).

LCMS (ESI+, m/z): 159.0 (M+H)⁺.

Step-2: Synthesis of ethyl (E)-6-bromohex-2-enoate
(Compound 8cc-ii)

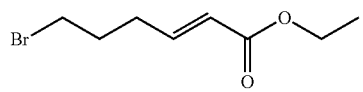

In a 100 mL round bottom flask, a solution of ethyl (E)-6-hydroxyhex-2-enoate (1.5 g, 9.40 mmol) in THF (10 mL) was treated with CBr₄ (4.68 g, 14.13 mmol) and PPh₃ (3.70 g, 14.13 mmol) at 0° C. The resulting reaction mixture was stirred at RT for 12 h. Upon completion of reaction (TLC), the reaction mixture was quenched with ice cold water and extracted with EtOAc (2×200 mL). The organic extract was separated, dried over anhydrous Na₂SO₄ and concentrated under reduced pressure. The residue obtained was purified by silica gel column chromatography (elution, 15% EtOAc in hexanes) to get the title compound. 0.98 g (46.9%).

¹H NMR (400 MHz, CDCl₃): δ 6.95-6.85 (m, 1H), 5.87 (d, J=15.6 Hz, 1H), 4.18 (q, J=7.2 Hz, 2H), 3.42 (t, J=6.8 Hz, 2H), 2.42-2.35 (m, 2H), 2.05-2.00 (m, 2H), 1.28 (t, J=7.2 Hz, 3H).

LCMS (ESI+, m/z): 221.1, 223.1 (M+H)⁺.

Step-3: Synthesis of ethyl (E)-6-(2-((4-(furan-2-yl)-N-methylbenzamido)methyl) phenoxy)hex-2-enoate
(Compound 8cc-ii)

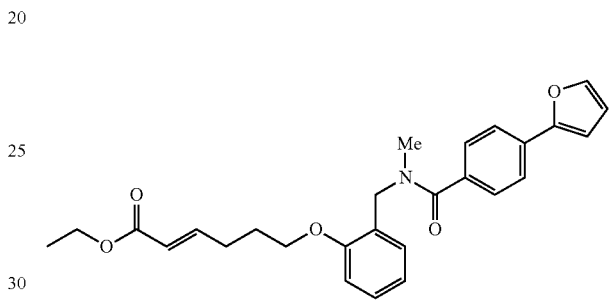

In a 250 mL round bottom flask, a solution of 4-(furan-2-yl)-N-(2-hydroxybenzyl)-N-methylbenzamide (0.4 g, 1.30 mmol) in DMF (15 mL) was treated with K₂CO₃ (0.539 g, 3.90 mmol) and ethyl (E)-6-bromohex-2-enoate (0.57 g, 2.60 mmol) at RT under nitrogen atmosphere. The resulting reaction mixture was heated at 80° C. with constant stirring for 5 h. The reaction mixture was cooled to RT, solid was filtered and washed with ethyl acetate. The combined filtrate was concentrated under reduced pressure and residue obtained was diluted with cold water (100 mL), before extracting with ethyl acetate (100 mL). The organic layer was washed with brine, dried over anhydrous Na₂SO₄ and concentrated under reduced pressure. The residue obtained was purified by silica gel column chromatography (elution, 20% EtOAc in hexanes) to afford the title compound (0.258 g, 44.2%).

LCMS (ESI+, m/z): 447.8 (M+H)⁺.

Step-4: Synthesis of (E)-6-(2-((4-(furan-2-yl)-N-methylbenzamido)methyl)phenoxy)hex-2-enoic acid
(Compound 8cc)

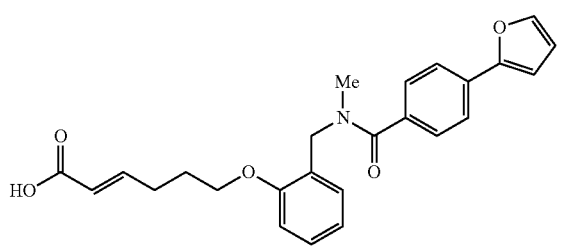 [SMILES: CN(Cc1ccccc1OCCC/C=C/C(=O)O)C(=O)c1ccc(-c2ccco2)cc1]

In a 100 mL round bottom flask, a stirred solution of ethyl (E)-6-(2-((4-(furan-2-yl)-N-methylbenzamido)methyl)phenoxy)hex-2-enoate (0.25 g, 0.55 mmol) in THF (15 mL) and water (5 mL), was treated with lithium hydroxide monohydrate (0.234 g, 5.59 mmol) at RT. The reaction mixture was stirred at RT for 12 h. Upon completion of reaction (TLC), the reaction mixture was concentrated under reduced pressure. The residue obtained was washed with EtOAc, diluted with cold water and acidified with 1 N HCl. The aqueous layer was extracted with EtOAc (3×25 mL). The combined organic extract was washed with brine and dried over anhydrous $Na_2SO_4$. The solution was concentrated under reduced pressure. The residue obtained was purified by silica gel preparative TLC (elution, 50% EtOAc in hexanes) to afford the title compound. Yield: 0.178 g (76.07%).

$^1$H NMR (400 MHz, DMSO-$d_6$, 60° C.): δ 11.98 (brs, 1H), 7.75 (s, 1H), 7.74 (d, J=8.4 Hz, 2H), 7.74 (d, J=8.4 Hz, 2H), 7.26 (m, 1H), 7.23-7.20 (m, 1H), 6.99-6.96 (m, 3H), 6.89-6.84 (m, 1H), 6.60 (brs, 1H), 5.77 (d, J=15.6 Hz, 1H), 4.59 (br s, 2H), 4.00 (brs, 2H), 2.90 (s, 3H), 2.33 (brs, 2H), 1.86 (brs, 2H).

LCMS (ESI+, m/z): 420.1 (M+H)$^+$ and 442.1 (M+Na)$^+$.
HPLC: 95.34% (210 nm).

We claim:

1. A compound of Formula (II):

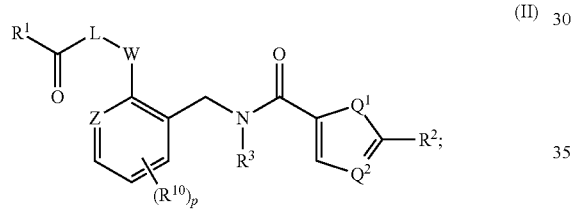

(II)

or a pharmaceutically acceptable salt thereof, wherein:
Z is CH, N, or

$R^1$ is —$OR^{1A}$ or —$NR^{1A}R^{1B}$;
$R^{1A}$, $R^{1B}$ are each independently hydrogen or $C_1$-$C_4$-alkyl;
W is O, $CH_2$, CH=CH, or C≡C;
L is selected from the group consisting of:

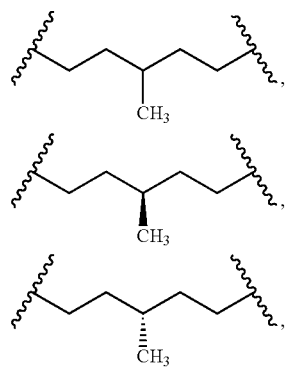

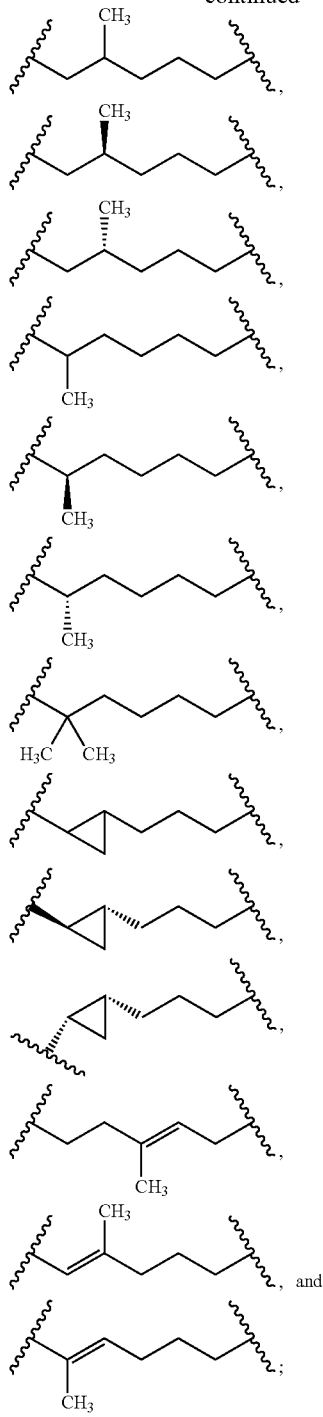

$Q^1$ is $CR^{20}$=$CR^{20}$, N=CH, CH=N, $\overset{\ominus}{O}$—$\overset{\oplus}{N}$=CH, HC=$\overset{\oplus}{N}$—$\overset{\ominus}{O}$, or S;
$Q^2$ is $CR^{20}$ or N;
each $R^{20}$ is independently hydrogen, halogen, $C_1$-$C_4$-alkyl, CN, or $C_1$-$C_4$-alkoxy;

each $R^{10}$ is independently hydrogen, halogen, $C_1$-$C_4$-alkyl, $C_1$-$C_4$-haloalkyl, $C_1$-$C_4$-alkoxy, $C_1$-$C_4$-haloalkoxy, or $C_3$-$C_6$-cycloalkyl;

p is an integer having a value of 1 or 2; and $R^2$ is halogen, $C_1$-$C_4$-alkyl, $C_3$-$C_6$-cycloalkyl, CN, $C_1$-$C_4$-alkoxy, $C_1$-$C_4$-haloalkoxy, $SO_2(C_1$-$C_4$-alkyl), 5- or 6-membered heterocycloalkyl, -=-$R^{2A}$, —O(CH$_2$)$_m$-$R^{2B}$, NH($C_1$-$C_4$-alkyl), N($C_1$-$C_4$-alkyl)$_2$, C(O)($C_1$-$C_4$-alkyl), optionally substituted aryl, or optionally substituted 5-membered heteroaryl;

m is an integer having an a value of 0, 1, 2, or 3;

$R^{2A}$ and $R^{2B}$ are each independently $C_1$-$C_4$-alkyl, $C_3$-$C_6$-cycloalkyl, or $C_1$-$C_4$ haloalkyl;

$R^3$ is $C_1$-$C_4$-alkyl,

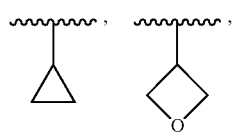

or $C_1$-$C_4$-haloalkyl; and with the proviso that the compound is not selected from the group consisting of:

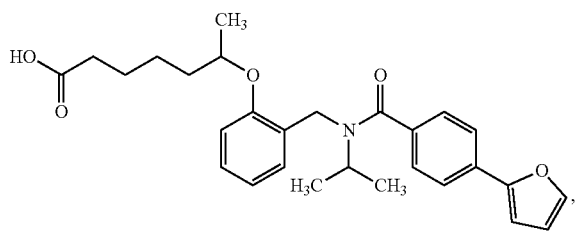

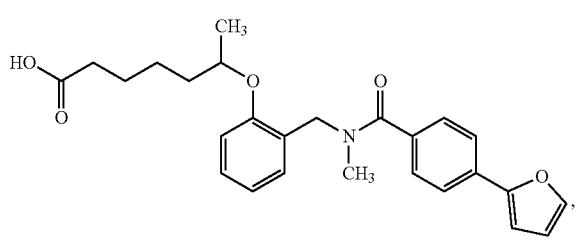

and

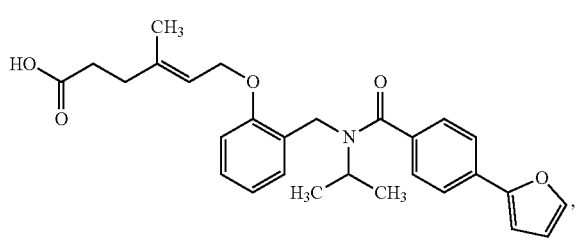

or a pharmaceutically acceptable salt thereof.

2. The compound of claim 1, wherein the compound has the structure of Formula (III):

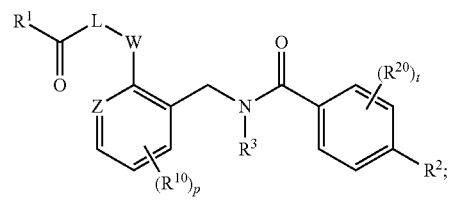

or a pharmaceutically acceptable salt thereof, wherein:

t is an integer having a value of 1 or 2.

3. The compound of claim 1, wherein the compound has the structure of Formula (VI) or (VII):

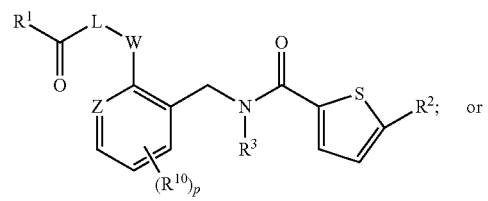

or

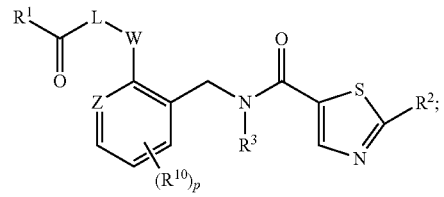

or a pharmaceutically acceptable salt thereof.

4. The compound of claim 1, wherein the compound has the structure of Formula (VIII):

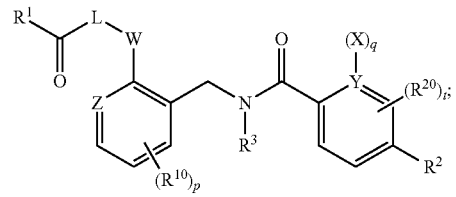

or a pharmaceutically acceptable salt thereof, wherein:

q is an integer having a value of 0 or 1;

X is $O^\ominus$; and

Y is $N^\oplus$ when q is 1; or

Y is N when q is 0; and t is an integer having a value of 1 or 2.

5. The compound of claim 1, wherein the compound has the structure of Formula (IX):

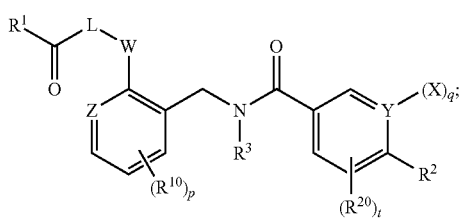

(IX)

or a pharmaceutically acceptable salt thereof, wherein:
q is an integer having a value of 0 or 1;
X is $O^{\ominus}$; and
Y is $N^{\oplus}$ when q is 1; or
Y is N when q is 0; and
t is an integer having a value of 1 or 2.

6. A compound of Formula (X):

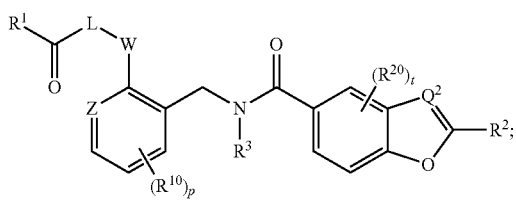

(X)

or a pharmaceutically acceptable salt thereof, wherein:
Z is CH, N, or

$R_1$ is $-OR^{1A}$ or $-NR^{1A}R^{1B}$;
$R^{1A}$, $R^{1B}$ are each independently hydrogen or $C_1$-$C_4$-alkyl;
W is O, $CH_2$, CH=CH, or C≡C;
L is selected from the group consisting of:

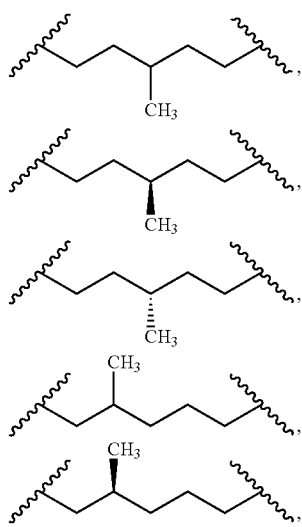

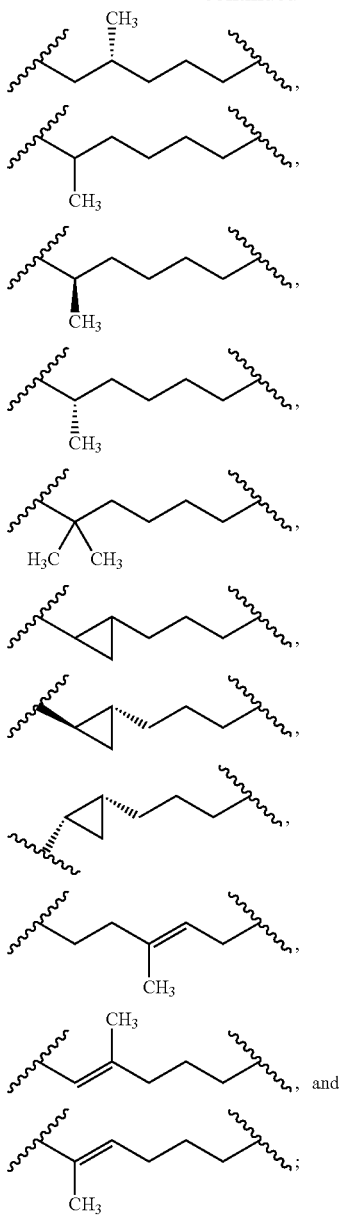

$R^2$ is halogen, $C_1$-$C_4$-alkyl, $C_3$-$C_6$-cycloalkyl, CN, $C_1$-$C_4$-alkoxy, $C_1$-$C_4$-haloalkoxy, $SO_2(C_1$-$C_4$-alkyl), 5- or 6-membered heterocycloalkyl, -≡-$R^{2A}$, $-O(CH_2)_mR^{2B}$, $NH(C_1$-$C_4$-alkyl), $N(C_1$-$C_4$-alkyl)$_2$, $C(O)(C_1$-$C_4$-alkyl), optionally substituted aryl, or optionally substituted 5-membered heteroaryl;

$Q^2$ is $CR^{20}$ or N;

p and t are integers each independently having a value of 1 or 2;

each $R^{10}$ is independently hydrogen, halogen, $C_1$-$C_4$-alkyl, $C_1$-$C_4$-haloalkoxy, $C_1$-$C_4$-alkoxy, $C_1$-$C_4$-haloalkoxy, or $C_3$-$C_6$-cycloalkyl; and each $R^{20}$ is independently hydrogen, halogen, $C_1$-$C_4$-alkyl, CN, or $C_1$-$C_4$-alkoxy.

7. The compound of claim 6, wherein the compound has the structure of Formula (XI):

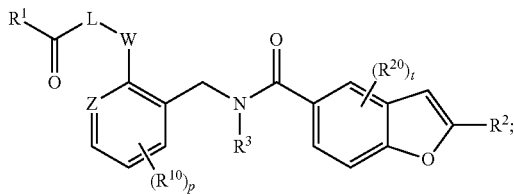

or a pharmaceutically acceptable salt thereof.

8. The compound of claim 2, wherein Z is CH.
9. The compound of claim 8, wherein W is O.
10. The compound of claim 9, wherein $R^3$ is methyl.
11. The compound of claim 10, wherein $R^2$ is phenyl, furanyl, thienyl, -≡-$CF_3$, $OCF_3$, or $OCHF_2$, wherein the phenyl can be optionally substituted with halogen, CN, $C_1$-$C_4$-alkyl, OH, $C_1$-$C_4$ alkoxy, formyl, acetyl, acetoxy, or carboxyl, and wherein the furanyl and the thienyl each can be optionally substituted with $C_1$-$C_4$-alkyl.
12. The compound of claim 11, wherein L is selected from the group consisting of:

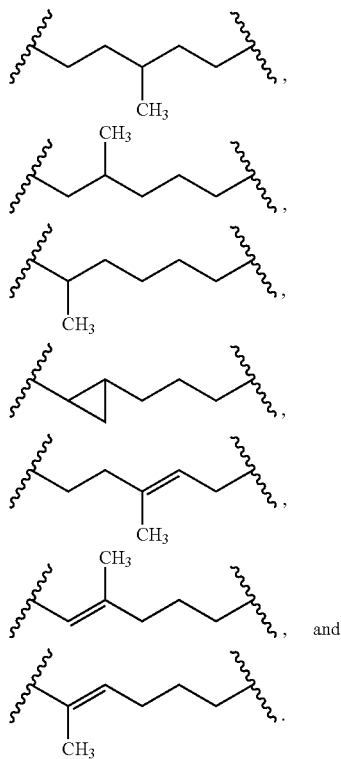

13. The compound of claim 12, wherein L is

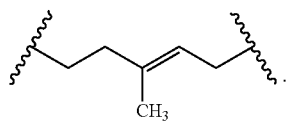 [SMILES: *C/C=C(\C)CC*]

14. The compound of claim 12, wherein $R^{10}$ is hydrogen, halogen, methyl, $OCH_3$, $CF_3$, $OCF_3$, $OCHF_2$, or cyclopropyl.

15. The compound of claim 14, wherein $R^{20}$ is hydrogen or halogen.
16. The compound of claim 2, wherein:
$R^1$ is OH;
W is O;
Z is CH;
L is

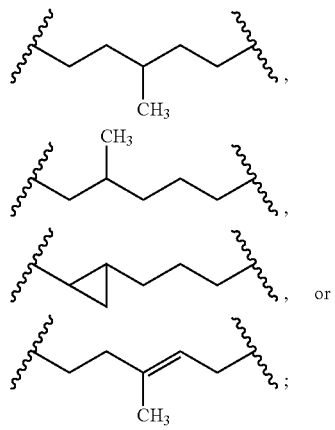

$R^2$ is unsubstituted furanyl or 5-methyl-2-furanyl;
$R^3$ is methyl;
p and t are 1;
$R^{10}$ is hydrogen, fluorine, bromine, methyl, or $OCH_3$; and
$R^{20}$ is hydrogen, fluorine, or chlorine.

17. A pharmaceutical composition comprising a pharmaceutically acceptable excipient and the compound of claim 1, or a pharmaceutically acceptable salt thereof.

18. A method of treating a PPARε related disease or condition in a subject, comprising administering to the subject in need thereof a therapeutically effective amount of one or more compounds of claim 1, or a pharmaceutically acceptable salt thereof, wherein the disease or condition is Duchenne muscular dystrophy (DMD), MELAS-Mitochondrial myopathy, Friedreich's Ataxia (FA), Adrenoleukodystrophy (ALD), nonalcoholic steatohepatitis (NASH), amyotrophic lateral sclerosis (ALS), or Kearns-Sayra Syndrome (KSS).

19. A method of increasing or maintaining muscle mass or muscle tone in a subject, comprising administering to the subject a therapeutically effective amount of one or more compounds of claim 1, or a pharmaceutically acceptable salt thereof.

20. A pharmaceutical composition comprising a pharmaceutically acceptable excipient and the compound of claim 6, or a pharmaceutically acceptable salt thereof.

21. A method of treating a PPARδ related disease or condition in a subject, comprising administering to the subject in need thereof a therapeutically effective amount of one or more compounds of claim 6, or a pharmaceutically acceptable salt thereof, wherein the disease or condition is Duchenne muscular dystrophy (DMD), MELAS-Mitochondrial myopathy, Friedreich's Ataxia (FA), Adrenoleukodystrophy (ALD), nonalcoholic steatohepatitis (NASH), amyotrophic lateral sclerosis (ALS), or Kearns-Sayra Syndrome (KSS).

22. A method of increasing or maintaining muscle mass or muscle tone in a subject, comprising administering to the subject a therapeutically effective amount of one or more compounds of claim 6, or a pharmaceutically acceptable salt thereof.

23. A method of treating a disease or condition in a subject, comprising administering to the subject in need thereof a therapeutically effective amount of one or more compounds of claim 1, or a pharmaceutically acceptable salt thereof, wherein the disease or condition is muscular dystrophy.

24. A method of treating a disease or condition in a subject, comprising administering to the subject in need thereof a therapeutically effective amount of one or more compounds of claim 6, or a pharmaceutically acceptable salt thereof, wherein the disease or condition is muscular dystrophy.

25. A method of treating a PPARδ related disease or condition in a subject, comprising administering to the subject in need thereof a therapeutically effective amount of a pharmaceutical composition comprising the compound of claim 1 and a pharmaceutically acceptable excipient, wherein the disease or condition is Duchenne muscular dystrophy (DMD), MELAS-Mitochondrial myopathy, Friedreich's Ataxia (FA), Adrenoleukodystrophy (ALD), nonalcoholic steatohepatitis (NASH), amyotrophic lateral sclerosis (ALS), or Kearns-Sayra Syndrome (KSS).

26. A method of increasing or maintaining muscle mass or muscle tone in a subject, comprising administering to the subject a therapeutically effective amount of a pharmaceutical composition comprising the compound of claim 1 and a pharmaceutically acceptable excipient.

27. A method of treating a PPARδ related disease or condition in a subject, comprising administering to the subject in need thereof a therapeutically effective amount of a pharmaceutical composition comprising the compound of claim 6 and a pharmaceutically acceptable excipient, wherein the disease or condition is Duchenne muscular dystrophy (DMD), MELAS-Mitochondrial myopathy, Friedreich's Ataxia (FA), Adrenoleukodystrophy (ALD), nonalcoholic steatohepatitis (NASH), amyotrophic lateral sclerosis (ALS), or Kearns-Sayra Syndrome (KSS).

28. A method of increasing or maintaining muscle mass or muscle tone in a subject, comprising administering to the subject a therapeutically effective amount of a pharmaceutical composition comprising the compound of claim 6 and a pharmaceutically acceptable excipient.

* * * * *

UNITED STATES PATENT AND TRADEMARK OFFICE
CERTIFICATE OF CORRECTION

PATENT NO. : 10,188,627 B2
APPLICATION NO. : 15/517893
DATED : January 29, 2019
INVENTOR(S) : Michael Downes et al.

Page 1 of 1

It is certified that error appears in the above-identified patent and that said Letters Patent is hereby corrected as shown below:

In the Claims

At Column 121, Claim 1, Lines 7-8, replace "–O(CH$_2$)$_m$·R$^{2B}$," with -- –O(CH$_2$)$_m$R$^{2B}$, --.

At Column 126, Claim 18, Line 35, replace "PPARε" with -- PPARδ --.

Signed and Sealed this
Twenty-sixth Day of March, 2019

Andrei Iancu
*Director of the United States Patent and Trademark Office*